US010927369B2

(12) United States Patent
Jacobson et al.

(10) Patent No.: US 10,927,369 B2
(45) Date of Patent: *Feb. 23, 2021

(54) METHODS FOR SORTING NUCLEIC ACIDS AND MULTIPLEXED PREPARATIVE IN VITRO CLONING

(71) Applicant: Gen9, Inc., Boston, MA (US)

(72) Inventors: Joseph Jacobson, Newton, MA (US); Martin J. Goldberg, Saratoga, CA (US); Li-Yun A. Kung, Arlington, MA (US); Daniel Schindler, Newton Upper Falls, MA (US); Michael E. Hudson, Framingham, MA (US)

(73) Assignee: Gen9, Inc., Boston, MA (US)

( * ) Notice: Subject to any disclaimer, the term of this patent is extended or adjusted under 35 U.S.C. 154(b) by 176 days.

This patent is subject to a terminal disclaimer.

(21) Appl. No.: 16/039,288

(22) Filed: Jul. 18, 2018

(65) Prior Publication Data
US 2019/0100751 A1    Apr. 4, 2019

Related U.S. Application Data

(63) Continuation of application No. 13/986,366, filed on Apr. 24, 2013, now Pat. No. 10,081,807.

(60) Provisional application No. 61/851,774, filed on Mar. 13, 2013, provisional application No. 61/848,961, filed on Jan. 16, 2013, provisional application No. 61/638,187, filed on Apr. 25, 2012, provisional application No. 61/377,750, filed on Apr. 24, 2012.

(51) Int. Cl.
*C12N 15/10* (2006.01)

(52) U.S. Cl.
CPC ..... *C12N 15/1065* (2013.01); *C12N 15/1034* (2013.01); *C12N 15/1093* (2013.01)

(58) Field of Classification Search
CPC ............ C12N 15/1093; C12N 15/1065; C12N 15/1034
See application file for complete search history.

(56) References Cited

U.S. PATENT DOCUMENTS

| | | |
|---|---|---|
| 4,500,707 A | 2/1985 | Caruthers et al. |
| 4,610,544 A | 9/1986 | Riley |
| 4,683,195 A | 7/1987 | Mullis et al. |
| 4,683,202 A | 7/1987 | Mullis |
| 4,689,405 A | 8/1987 | Frank et al. |
| 4,725,677 A | 2/1988 | Koester et al. |
| 4,800,159 A | 1/1989 | Mullis et al. |
| 4,888,286 A | 12/1989 | Crea |
| 4,959,317 A | 9/1990 | Sauer |
| 4,965,188 A | 10/1990 | Mullis et al. |
| 4,999,294 A | 3/1991 | Looney et al. |
| 5,047,524 A | 9/1991 | Andrus et al. |
| 5,093,251 A | 3/1992 | Richards et al. |
| 5,096,825 A | 3/1992 | Barr et al. |
| 5,104,789 A | 4/1992 | Permar et al. |
| 5,104,792 A | 4/1992 | Silver et al. |
| 5,132,215 A | 7/1992 | Jayaraman et al. |
| 5,143,854 A | 9/1992 | Pirrung et al. |
| 5,288,514 A | 2/1994 | Ellman |
| 5,356,802 A | 10/1994 | Chandrasegaran |
| 5,384,261 A | 1/1995 | Winkler et al. |
| 5,395,750 A | 3/1995 | Dillon et al. |
| 5,405,783 A | 4/1995 | Pirrung et al. |
| 5,424,186 A | 6/1995 | Fodor et al. |
| 5,436,150 A | 7/1995 | Chandrasegaran |
| 5,436,327 A | 7/1995 | Southern et al. |
| 5,445,934 A | 8/1995 | Fodor et al. |
| 5,459,039 A | 10/1995 | Modrich et al. |
| 5,474,796 A | 12/1995 | Brennan |
| 5,498,531 A | 3/1996 | Jarrell |
| 5,508,169 A | 4/1996 | Deugau et al. |
| 5,510,270 A | 4/1996 | Fodor et al. |
| 5,512,463 A | 4/1996 | Stemmer |
| 5,514,789 A | 5/1996 | Kempe |
| 5,527,681 A | 6/1996 | Holmes |
| 5,541,061 A | 7/1996 | Fodor et al. |
| 5,556,750 A | 9/1996 | Modrich et al. |
| 5,604,097 A | 2/1997 | Brenner |
| 5,605,793 A | 2/1997 | Stemmer |
| 5,624,711 A | 4/1997 | Sundberg et al. |
| 5,639,603 A | 6/1997 | Dower et al. |
| 5,641,658 A | 6/1997 | Adams et al. |
| 5,653,939 A | 8/1997 | Hollis et al. |
| 5,674,742 A | 10/1997 | Northrup et al. |
| 5,679,522 A | 10/1997 | Modrich et al. |
| 5,695,940 A | 12/1997 | Drmanac et al. |
| 5,700,637 A | 12/1997 | Southern |
| 5,700,642 A | 12/1997 | Monforte et al. |
| 5,702,894 A | 12/1997 | Modrich et al. |
| 5,738,829 A | 4/1998 | Kempe |
| 5,739,386 A | 4/1998 | Holmes |
| 5,750,335 A | 5/1998 | Gifford |
| 5,766,550 A | 6/1998 | Kaplan et al. |
| 5,770,358 A | 6/1998 | Dower et al. |
| 5,780,272 A | 7/1998 | Jarrell |
| 5,795,714 A | 8/1998 | Cantor et al. |

(Continued)

FOREIGN PATENT DOCUMENTS

| | | |
|---|---|---|
| CN | 1145641 A | 3/1997 |
| CN | 1468313 A | 1/2004 |

(Continued)

OTHER PUBLICATIONS

[No Author Listed], TnT ® coupled reticulocyte lysate system, Technical Bulletin (Promega, Madison, Wis), 2013.

(Continued)

*Primary Examiner* — David C Thomas

(74) *Attorney, Agent, or Firm* — Wolf, Greenfield & Sacks, P.C.

(57) ABSTRACT

Methods and compositions relate to the sorting and cloning of high fidelity nucleic acids using high throughput sequencing. Specifically, nucleic acid molecules having the desired predetermined sequence can be sorted from a pool comprising a plurality of nucleic acids having correct and incorrect sequences.

20 Claims, 24 Drawing Sheets

Specification includes a Sequence Listing.

(56) References Cited

U.S. PATENT DOCUMENTS

| | | |
|---|---|---|
| 5,830,655 A | 11/1998 | Monforte et al. |
| 5,830,721 A | 11/1998 | Stemmer et al. |
| 5,834,252 A | 11/1998 | Stemmer et al. |
| 5,858,754 A | 1/1999 | Modrich et al. |
| 5,861,482 A | 1/1999 | Modrich et al. |
| 5,871,902 A | 2/1999 | Weininger et al. |
| 5,876,604 A | 3/1999 | Nemser et al. |
| 5,877,280 A | 3/1999 | Wetmur |
| 5,912,129 A | 6/1999 | Vinayagamoorthy et al. |
| 5,916,794 A | 6/1999 | Chandrasegaran |
| 5,922,539 A | 7/1999 | Modrich et al. |
| 5,928,905 A | 7/1999 | Stemmer et al. |
| 5,929,208 A | 7/1999 | Heller et al. |
| 5,942,609 A | 8/1999 | Hunkapiller et al. |
| 5,953,469 A | 9/1999 | Zhou |
| 6,008,031 A | 12/1999 | Modrich et al. |
| 6,013,440 A | 1/2000 | Lipshutz et al. |
| 6,017,696 A | 1/2000 | Heller |
| 6,027,877 A | 2/2000 | Wagner, Jr. |
| 6,042,211 A | 3/2000 | Hudson et al. |
| 6,093,302 A | 7/2000 | Montgomery |
| 6,103,463 A | 8/2000 | Chetverin et al. |
| 6,110,668 A | 8/2000 | Strizhov et al. |
| 6,136,568 A | 10/2000 | Hiatt et al. |
| 6,143,527 A | 11/2000 | Pachuk et al. |
| 6,150,102 A | 11/2000 | Mills, Jr. et al. |
| 6,150,141 A | 11/2000 | Jarrell |
| 6,165,793 A | 12/2000 | Stemmer |
| 6,177,558 B1 | 1/2001 | Brennan et al. |
| 6,242,211 B1 | 6/2001 | Peterson et al. |
| 6,248,521 B1 | 6/2001 | Van Ness et al. |
| 6,261,797 B1 | 7/2001 | Sorge et al. |
| 6,271,957 B1 | 8/2001 | Quate et al. |
| 6,277,632 B1 | 8/2001 | Harney |
| 6,280,595 B1 | 8/2001 | Montgomery |
| 6,284,463 B1 | 9/2001 | Hasebe et al. |
| 6,287,825 B1 | 9/2001 | Weissman et al. |
| 6,287,861 B1 | 9/2001 | Stemmer et al. |
| 6,291,242 B1 | 9/2001 | Stemmer |
| 6,315,958 B1 | 11/2001 | Singh-Gasson et al. |
| 6,322,971 B1 | 11/2001 | Chetverin et al. |
| 6,326,489 B1 | 12/2001 | Church et al. |
| 6,333,153 B1 | 12/2001 | Fishel et al. |
| 6,346,399 B1 | 2/2002 | Weissman et al. |
| 6,355,412 B1 | 3/2002 | Stewart et al. |
| 6,355,423 B1 | 3/2002 | Rothberg et al. |
| 6,358,712 B1 | 3/2002 | Jarrell et al. |
| 6,365,355 B1 | 4/2002 | McCutchen-Maloney |
| 6,372,429 B1 | 4/2002 | Sharon |
| 6,372,434 B1 | 4/2002 | Weissman |
| 6,372,484 B1 | 4/2002 | Ronchi et al. |
| 6,375,903 B1 | 4/2002 | Cerrina et al. |
| 6,376,246 B1 | 4/2002 | Crameri et al. |
| 6,406,847 B1 | 6/2002 | Cox et al. |
| 6,410,220 B1 | 6/2002 | Hodgson |
| 6,416,164 B1 | 7/2002 | Stearns et al. |
| 6,426,184 B1 | 7/2002 | Gao et al. |
| 6,432,360 B1 | 8/2002 | Church |
| 6,444,111 B1 | 9/2002 | Montgomery |
| 6,444,175 B1 | 9/2002 | Singh-Gasson et al. |
| 6,444,650 B1 | 9/2002 | Cech et al. |
| 6,444,661 B1 | 9/2002 | Barton et al. |
| 6,472,184 B1 | 10/2002 | Hegemann et al. |
| 6,479,652 B1 | 11/2002 | Crameri et al. |
| 6,480,324 B2 | 11/2002 | Quate et al. |
| 6,489,146 B2 | 12/2002 | Stemmer |
| 6,495,318 B2 | 12/2002 | Harney |
| 6,506,603 B1 | 1/2003 | Stemmer |
| 6,509,156 B1 | 1/2003 | Stewart |
| 6,511,849 B1 | 1/2003 | Wang |
| 6,514,704 B2 | 2/2003 | Bruce et al. |
| 6,521,427 B1 | 2/2003 | Evans |
| 6,534,271 B2 | 3/2003 | Furste |
| 6,537,776 B1 | 3/2003 | Short |
| 6,565,727 B1 | 5/2003 | Shenderov |
| 6,586,211 B1 | 7/2003 | Stahler et al. |
| 6,593,111 B2 | 7/2003 | Baric et al. |
| 6,596,239 B2 | 7/2003 | Williams et al. |
| 6,605,451 B1 | 8/2003 | Marmaro et al. |
| 6,610,499 B1 | 8/2003 | Fulwyler et al. |
| 6,613,581 B1 | 9/2003 | Wada et al. |
| 6,632,641 B1 | 10/2003 | Brennan |
| 6,650,822 B1 | 11/2003 | Zhou |
| 6,658,802 B2 | 12/2003 | Lucas, Jr. et al. |
| 6,660,475 B2 | 12/2003 | Jack et al. |
| 6,664,112 B2 | 12/2003 | Mulligan et al. |
| 6,664,388 B2 | 12/2003 | Nelson |
| 6,670,127 B2 | 12/2003 | Evans |
| 6,670,605 B1 | 12/2003 | Storm, Jr. et al. |
| 6,800,439 B1 | 10/2004 | McGall et al. |
| 6,802,593 B2 | 10/2004 | Ellson et al. |
| 6,824,866 B1 | 11/2004 | Glazer et al. |
| 6,830,890 B2 | 12/2004 | Lockhart et al. |
| 6,833,450 B1 | 12/2004 | McGall et al. |
| 6,846,655 B1 | 1/2005 | Wagner et al. |
| 6,897,025 B2 | 5/2005 | Cox et al. |
| 6,911,132 B2 | 6/2005 | Pamula et al. |
| 6,921,818 B2 | 7/2005 | Sproat |
| 6,932,097 B2 | 8/2005 | Ellson et al. |
| 6,946,296 B2 | 9/2005 | Patten et al. |
| 6,955,901 B2 | 10/2005 | Schouten |
| 6,969,587 B2 | 11/2005 | Taylor |
| 6,969,847 B2 | 11/2005 | Davis et al. |
| 7,090,333 B2 | 8/2006 | Mutz et al. |
| 7,133,782 B2 | 11/2006 | Odedra |
| 7,144,734 B2 | 12/2006 | Court et al. |
| 7,169,560 B2 | 1/2007 | Lapidus et al. |
| 7,179,423 B2 | 2/2007 | Bohm et al. |
| 7,183,406 B2 | 2/2007 | Belshaw |
| 7,199,233 B1 | 4/2007 | Jensen et al. |
| 7,262,031 B2 | 8/2007 | Lathrop |
| 7,273,730 B2 | 9/2007 | Du Breuil Lastrucci |
| 7,285,835 B2 | 10/2007 | Rizzo et al. |
| 7,303,320 B1 | 12/2007 | Ashley |
| 7,303,872 B2 | 12/2007 | Sussman |
| 7,323,320 B2 | 1/2008 | Oleinikov |
| 7,399,590 B2 | 7/2008 | Piepenburg et al. |
| 7,432,055 B2 | 10/2008 | Pemov et al. |
| 7,498,176 B2 | 3/2009 | McCormick et al. |
| 7,537,897 B2 | 5/2009 | Brenner et al. |
| 7,563,600 B2 | 7/2009 | Oleinikov |
| 7,699,979 B2 | 4/2010 | Li et al. |
| 7,723,077 B2 | 5/2010 | Young et al. |
| 7,820,412 B2 | 10/2010 | Belshaw et al. |
| 7,879,580 B2 | 2/2011 | Carr et al. |
| 7,932,025 B2 | 4/2011 | Carr et al. |
| 8,053,191 B2 | 11/2011 | Blake |
| 8,058,004 B2 | 11/2011 | Oleinikov |
| 8,137,906 B2 | 3/2012 | Schatz |
| 8,173,368 B2 | 5/2012 | Staehler et al. |
| 8,338,091 B2 | 12/2012 | Chesnut et al. |
| 8,476,018 B2 | 7/2013 | Brenner |
| 8,716,467 B2 | 5/2014 | Jacobson |
| 8,808,986 B2 | 8/2014 | Jacobson et al. |
| 9,023,601 B2 | 5/2015 | Oleinikov |
| 9,023,649 B2 | 5/2015 | Mali et al. |
| 9,051,666 B2 | 6/2015 | Oleinikov |
| 9,085,798 B2 | 7/2015 | Chee |
| 9,150,853 B2 | 10/2015 | Hudson et al. |
| 9,295,965 B2 | 3/2016 | Jacobson et al. |
| 9,322,037 B2 | 4/2016 | Liu et al. |
| 9,752,176 B2 | 9/2017 | Kung et al. |
| 10,081,807 B2 | 9/2018 | Jacobson et al. |
| 2001/0012537 A1 | 8/2001 | Anderson et al. |
| 2001/0031483 A1 | 10/2001 | Sorge et al. |
| 2001/0049125 A1 | 12/2001 | Stemmer et al. |
| 2001/0053519 A1 | 12/2001 | Fodor et al. |
| 2002/0012616 A1 | 1/2002 | Zhou et al. |
| 2002/0025561 A1 | 2/2002 | Hodgson |
| 2002/0037579 A1 | 3/2002 | Ellson et al. |
| 2002/0058275 A1 | 5/2002 | Fishel et al. |
| 2002/0081582 A1 | 6/2002 | Gao et al. |
| 2002/0127552 A1 | 9/2002 | Church et al. |
| 2002/0132259 A1 | 9/2002 | Wagner et al. |

(56) References Cited

U.S. PATENT DOCUMENTS

| | | |
|---|---|---|
| 2002/0132308 A1 | 9/2002 | Liu et al. |
| 2002/0133359 A1 | 9/2002 | Brown |
| 2003/0017552 A1 | 1/2003 | Jarrell et al. |
| 2003/0044980 A1 | 3/2003 | Mancebo et al. |
| 2003/0047688 A1 | 3/2003 | Faris et al. |
| 2003/0050437 A1 | 3/2003 | Montgomery |
| 2003/0050438 A1 | 3/2003 | Montgomery |
| 2003/0054390 A1 | 3/2003 | Crameri et al. |
| 2003/0068633 A1 | 4/2003 | Belshaw et al. |
| 2003/0068643 A1 | 4/2003 | Brennan et al. |
| 2003/0082630 A1 | 5/2003 | Kolkman et al. |
| 2003/0087298 A1 | 5/2003 | Green et al. |
| 2003/0091476 A1 | 5/2003 | Zhou et al. |
| 2003/0099952 A1 | 5/2003 | Green et al. |
| 2003/0118485 A1 | 6/2003 | Singh-Gasson et al. |
| 2003/0118486 A1 | 6/2003 | Zhou et al. |
| 2003/0120035 A1 | 6/2003 | Gao et al. |
| 2003/0134807 A1 | 7/2003 | Hardin et al. |
| 2003/0143550 A1 | 7/2003 | Green et al. |
| 2003/0143724 A1 | 7/2003 | Cerrina et al. |
| 2003/0165841 A1 | 9/2003 | Burgin et al. |
| 2003/0170616 A1 | 9/2003 | Wang et al. |
| 2003/0171325 A1 | 9/2003 | Gascoyne et al. |
| 2003/0175907 A1 | 9/2003 | Frazer et al. |
| 2003/0186226 A1 | 10/2003 | Brennan et al. |
| 2003/0198948 A1 | 10/2003 | Stahler et al. |
| 2003/0215837 A1 | 11/2003 | Frey et al. |
| 2003/0215855 A1 | 11/2003 | Dubrow et al. |
| 2003/0215856 A1 | 11/2003 | Church et al. |
| 2003/0219781 A1 | 11/2003 | Frey |
| 2003/0224521 A1 | 12/2003 | Court et al. |
| 2004/0002103 A1 | 1/2004 | Short |
| 2004/0005673 A1 | 1/2004 | Jarrell et al. |
| 2004/0009479 A1 | 1/2004 | Wohlgemuth et al. |
| 2004/0009520 A1 | 1/2004 | Albert et al. |
| 2004/0014083 A1 | 1/2004 | Yuan et al. |
| 2004/0053362 A1 | 3/2004 | De Luca et al. |
| 2004/0096891 A1 | 5/2004 | Bennett |
| 2004/0101444 A1 | 5/2004 | Sommers et al. |
| 2004/0101894 A1 | 5/2004 | Albert et al. |
| 2004/0101949 A1 | 5/2004 | Green et al. |
| 2004/0106728 A1 | 6/2004 | McGall et al. |
| 2004/0110211 A1 | 6/2004 | McCormick et al. |
| 2004/0110212 A1 | 6/2004 | McCormick et al. |
| 2004/0126757 A1 | 7/2004 | Cerrina |
| 2004/0132029 A1 | 7/2004 | Sussman et al. |
| 2004/0166567 A1 | 8/2004 | Santi et al. |
| 2004/0171047 A1 | 9/2004 | Dahl et al. |
| 2004/0185484 A1 | 9/2004 | Costa et al. |
| 2004/0229359 A1 | 11/2004 | Mead et al. |
| 2004/0241655 A1 | 12/2004 | Hwang et al. |
| 2004/0259146 A1 | 12/2004 | Friend et al. |
| 2005/0053997 A1 | 3/2005 | Evans |
| 2005/0069928 A1 | 3/2005 | Nelson et al. |
| 2005/0079510 A1 | 4/2005 | Berka et al. |
| 2005/0089889 A1 | 4/2005 | Ramsing et al. |
| 2005/0106606 A1 | 5/2005 | Parker et al. |
| 2005/0112574 A1 | 5/2005 | Gamble et al. |
| 2005/0118628 A1 | 6/2005 | Evans |
| 2005/0202429 A1 | 9/2005 | Trau et al. |
| 2005/0208503 A1 | 9/2005 | Yowanto et al. |
| 2005/0221340 A1 | 10/2005 | Evans |
| 2005/0227235 A1 | 10/2005 | Carr et al. |
| 2005/0227316 A1 | 10/2005 | Santi et al. |
| 2005/0255477 A1 | 11/2005 | Carr et al. |
| 2005/0287585 A1 | 12/2005 | Oleinikov |
| 2006/0003347 A1 | 1/2006 | Griffiths et al. |
| 2006/0008833 A1 | 1/2006 | Jacobson |
| 2006/0014146 A1 | 1/2006 | Sucaille et al. |
| 2006/0035218 A1 | 2/2006 | Oleinikov |
| 2006/0040297 A1 | 2/2006 | Leamon et al. |
| 2006/0054503 A1 | 3/2006 | Pamula et al. |
| 2006/0127920 A1 | 6/2006 | Church et al. |
| 2006/0127926 A1 | 6/2006 | Belshaw et al. |
| 2006/0134638 A1 | 6/2006 | Mulligan et al. |
| 2006/0160138 A1 | 7/2006 | Church et al. |
| 2006/0194214 A1 | 8/2006 | Church et al. |
| 2006/0281113 A1 | 12/2006 | Church et al. |
| 2006/0286678 A1 | 12/2006 | Dual et al. |
| 2007/0004041 A1 | 1/2007 | Church et al. |
| 2007/0122817 A1 | 5/2007 | Church et al. |
| 2007/0169227 A1 | 7/2007 | Cigan et al. |
| 2007/0231805 A1 | 10/2007 | Baynes et al. |
| 2007/0269870 A1 | 11/2007 | Church et al. |
| 2007/0281309 A1 | 12/2007 | Kong et al. |
| 2008/0003571 A1 | 1/2008 | McKernan et al. |
| 2008/0009420 A1 | 1/2008 | Schroth et al. |
| 2008/0044862 A1 | 2/2008 | Schatz et al. |
| 2008/0064610 A1 | 3/2008 | Lipovsek et al. |
| 2008/0105829 A1 | 5/2008 | Faris et al. |
| 2008/0214408 A1 | 9/2008 | Chatterjee et al. |
| 2008/0261300 A1 | 10/2008 | Santi et al. |
| 2008/0274510 A1 | 11/2008 | Santi et al. |
| 2008/0274513 A1 | 11/2008 | Shenderov et al. |
| 2008/0287320 A1 | 11/2008 | Baynes et al. |
| 2008/0300842 A1 | 12/2008 | Govindarajan et al. |
| 2009/0016932 A1 | 1/2009 | Curcio et al. |
| 2009/0036323 A1 | 2/2009 | van Eijk et al. |
| 2009/0087840 A1 | 4/2009 | Baynes et al. |
| 2009/0093378 A1 | 4/2009 | Bignell et al. |
| 2009/0137408 A1 | 5/2009 | Jacobson |
| 2009/0155858 A1 | 6/2009 | Blake |
| 2009/0280497 A1 | 11/2009 | Woudenberg et al. |
| 2009/0280697 A1 | 11/2009 | Li et al. |
| 2009/0305233 A1 | 12/2009 | Borovkov et al. |
| 2010/0015614 A1 | 1/2010 | Beer et al. |
| 2010/0015668 A1 | 1/2010 | Staehler et al. |
| 2010/0016178 A1 | 1/2010 | Sussman et al. |
| 2010/0028873 A1 | 2/2010 | Belouchi et al. |
| 2010/0028885 A1 | 2/2010 | Balasubramanian et al. |
| 2010/0124767 A1 | 5/2010 | Oleinikov |
| 2010/0261158 A1 | 10/2010 | Nordman et al. |
| 2010/0273219 A1 | 10/2010 | May et al. |
| 2010/0311058 A1 | 12/2010 | Kim et al. |
| 2011/0052446 A1 | 3/2011 | Hirano et al. |
| 2011/0117625 A1 | 5/2011 | Lippow et al. |
| 2011/0160078 A1 | 6/2011 | Fodor et al. |
| 2011/0172127 A1 | 7/2011 | Jacobson et al. |
| 2011/0217738 A1 | 9/2011 | Jacobson |
| 2011/0283110 A1 | 11/2011 | Dapkus et al. |
| 2011/0287490 A1 | 11/2011 | Coope et al. |
| 2012/0028843 A1 | 2/2012 | Ramu et al. |
| 2012/0115756 A1 | 5/2012 | Williams et al. |
| 2012/0185965 A1 | 7/2012 | Senger et al. |
| 2012/0220497 A1 | 8/2012 | Jacobson et al. |
| 2012/0270750 A1 | 10/2012 | Oleinikov |
| 2012/0270754 A1 | 10/2012 | Blake |
| 2012/0283110 A1 | 11/2012 | Shendure et al. |
| 2012/0283140 A1 | 11/2012 | Chu |
| 2012/0315670 A1 | 12/2012 | Jacobson et al. |
| 2012/0322681 A1 | 12/2012 | Kung et al. |
| 2013/0005582 A1 | 1/2013 | Lower |
| 2013/0017977 A1 | 1/2013 | Oleinikov |
| 2013/0059296 A1 | 3/2013 | Jacobson et al. |
| 2013/0059344 A1 | 3/2013 | Striedner et al. |
| 2013/0059761 A1 | 3/2013 | Jacobson et al. |
| 2013/0085083 A1 | 4/2013 | Kamberov et al. |
| 2013/0130347 A1 | 5/2013 | Delisa et al. |
| 2013/0196373 A1 | 8/2013 | Gregory et al. |
| 2013/0224729 A1 | 8/2013 | Church et al. |
| 2013/0225421 A1 | 8/2013 | Li et al. |
| 2013/0244884 A1 | 9/2013 | Jacobson et al. |
| 2013/0252849 A1 | 9/2013 | Hudson et al. |
| 2013/0163263 A1 | 10/2013 | Jacobson et al. |
| 2013/0274135 A1 | 10/2013 | Zhang et al. |
| 2013/0281308 A1 | 10/2013 | Kung et al. |
| 2013/0296192 A1 | 11/2013 | Jacobson |
| 2013/0296194 A1 | 11/2013 | Jacobson |
| 2013/0309725 A1 | 11/2013 | Jacobson |
| 2014/0141982 A1 | 5/2014 | Jacobson et al. |
| 2014/0295556 A1 | 10/2014 | Joung et al. |
| 2014/0309119 A1 | 10/2014 | Jacobson et al. |
| 2015/0031089 A1 | 1/2015 | Lindstrom |
| 2015/0045234 A1 | 2/2015 | Stone et al. |

(56) References Cited

U.S. PATENT DOCUMENTS

| | | |
|---|---|---|
| 2015/0065393 A1 | 3/2015 | Jacobson |
| 2015/0191719 A1 | 7/2015 | Hudson et al. |
| 2015/0203839 A1 | 7/2015 | Jacobson et al. |
| 2015/0315547 A1 | 11/2015 | Oberg |
| 2015/0361420 A1 | 12/2015 | Hudson et al. |
| 2015/0368687 A1 | 12/2015 | Saaem et al. |
| 2015/0376602 A1 | 12/2015 | Jacobson et al. |
| 2016/0001247 A1 | 1/2016 | Oleinikov |
| 2016/0097051 A1 | 4/2016 | Jacobson et al. |
| 2016/0122755 A1 | 5/2016 | Hall et al. |
| 2016/0144332 A1 | 5/2016 | Chu |
| 2016/0144333 A1 | 5/2016 | Jacobson et al. |
| 2016/0168564 A1 | 6/2016 | Jacobson et al. |
| 2016/0215381 A1 | 7/2016 | Levine et al. |
| 2016/0250613 A1 | 9/2016 | Jacobson et al. |
| 2016/0326520 A1 | 11/2016 | Ramu et al. |
| 2017/0067805 A1 | 3/2017 | Horiba et al. |
| 2017/0137858 A1 | 5/2017 | Carr et al. |
| 2017/0144155 A1 | 5/2017 | Bohm et al. |
| 2017/0175110 A1 | 6/2017 | Jacobson et al. |
| 2017/0198268 A1 | 7/2017 | Jacobson et al. |
| 2017/0349925 A1 | 12/2017 | Jacobson et al. |
| 2018/0023120 A1 | 1/2018 | Kung et al. |
| 2018/0355353 A1 | 12/2018 | Saaem |
| 2019/0010530 A1 | 1/2019 | Saaem |

FOREIGN PATENT DOCUMENTS

| | | |
|---|---|---|
| CN | 101921840 | 12/2010 |
| DE | 4343591 | 6/1995 |
| EP | 0259160 | 3/1988 |
| EP | 1015576 | 7/2000 |
| EP | 1159285 | 12/2001 |
| EP | 1205548 | 5/2002 |
| EP | 1314783 | 5/2003 |
| EP | 1411122 | 4/2004 |
| EP | 2017356 | 1/2009 |
| EP | 2175021 | 4/2010 |
| JP | 2005-538725 A | 12/2005 |
| JP | 2005-538725 A | 12/2005 |
| JP | 2007-533308 A | 11/2007 |
| KR | 100491810 B1 | 11/2005 |
| WO | WO 1990/000626 | 1/1990 |
| WO | WO 1992/015694 A1 | 9/1992 |
| WO | WO 1993/017126 | 9/1993 |
| WO | WO 1993/020092 | 10/1993 |
| WO | WO 1994/018226 | 8/1994 |
| WO | WO 1995/017413 | 6/1995 |
| WO | WO 1996/033207 | 10/1996 |
| WO | WO 1996/034112 | 10/1996 |
| WO | WO 1997/035957 | 10/1997 |
| WO | WO 1998/005765 | 2/1998 |
| WO | WO 1998/020020 | 5/1998 |
| WO | WO 1998/038299 | 9/1998 |
| WO | WO 1998/038326 | 9/1998 |
| WO | WO 1999/014318 | 3/1999 |
| WO | WO 1999/019341 | 4/1999 |
| WO | WO 1999/025724 | 5/1999 |
| WO | WO 1999/042813 | 8/1999 |
| WO | WO 1999/047536 | 9/1999 |
| WO | WO 2000/029616 | 5/2000 |
| WO | WO 2000/040715 | 7/2000 |
| WO | WO 2000/046386 | 8/2000 |
| WO | WO 2000/049142 | 8/2000 |
| WO | WO 2000/053617 A1 | 9/2000 |
| WO | WO 2000/075368 | 12/2000 |
| WO | WO 2001/081568 | 11/2001 |
| WO | WO 2001/085075 | 11/2001 |
| WO | WO 2001/088173 A2 | 11/2001 |
| WO | WO 2002/004597 A2 | 1/2002 |
| WO | WO-2002/024597 A2 | 3/2002 |
| WO | WO 2002/081490 A2 | 10/2002 |
| WO | WO 2002/095073 A1 | 11/2002 |
| WO | WO 2002/101004 A2 | 12/2002 |
| WO | WO 2003/010311 A2 | 2/2003 |
| WO | WO 2003/033718 | 4/2003 |
| WO | WO 2003/040410 | 5/2003 |
| WO | WO 2003/044193 | 5/2003 |
| WO | WO 2003/046223 | 6/2003 |
| WO | WO 2003/054232 | 7/2003 |
| WO | WO 2003/060084 | 7/2003 |
| WO | WO 2003/064026 | 8/2003 |
| WO | WO 2003/064027 | 8/2003 |
| WO | WO 2003/064611 | 8/2003 |
| WO | WO 2003/064699 | 8/2003 |
| WO | WO 2003/065038 | 8/2003 |
| WO | WO 2003/066212 | 8/2003 |
| WO | WO 2003/083604 A2 | 10/2003 |
| WO | WO 2003/085094 | 10/2003 |
| WO | WO 2003/089605 A2 | 10/2003 |
| WO | WO 2003/100012 | 12/2003 |
| WO | WO 2004/002627 A2 | 1/2004 |
| WO | WO 2004/024886 | 3/2004 |
| WO | WO 2004/029586 | 4/2004 |
| WO | WO 2004/031351 | 4/2004 |
| WO | WO 2004/031399 | 4/2004 |
| WO | WO 2004/034028 A2 | 4/2004 |
| WO | WO 2004/090170 | 10/2004 |
| WO | WO 2005/059096 | 6/2005 |
| WO | WO 2005/071077 | 8/2005 |
| WO | WO 2005/089110 | 9/2005 |
| WO | WO 2005/103279 | 11/2005 |
| WO | WO 2005/107939 | 11/2005 |
| WO | WO 2005/123956 | 12/2005 |
| WO | WO 2006/031745 | 3/2006 |
| WO | WO 2006/044956 | 4/2006 |
| WO | WO 2006/049843 | 5/2006 |
| WO | WO 2006/076679 | 7/2006 |
| WO | WO 2006/086209 | 8/2006 |
| WO | WO 2006/127423 | 11/2006 |
| WO | WO 2007/008951 | 1/2007 |
| WO | WO 2007/009082 | 1/2007 |
| WO | WO 2007/010252 | 1/2007 |
| WO | WO 2007/075438 | 7/2007 |
| WO | WO 2007/087347 | 8/2007 |
| WO | WO 2007/113688 A2 | 10/2007 |
| WO | WO 2007/117396 | 10/2007 |
| WO | WO 2007/120624 | 10/2007 |
| WO | WO 2007/123742 | 11/2007 |
| WO | WO 2007/136736 | 11/2007 |
| WO | WO 2007/136833 A2 | 11/2007 |
| WO | WO 2007/136834 | 11/2007 |
| WO | WO 2007/136835 | 11/2007 |
| WO | WO 2007/136840 | 11/2007 |
| WO | WO 2008/024319 | 2/2008 |
| WO | WO 2008/027558 | 3/2008 |
| WO | WO 2008/041002 | 4/2008 |
| WO | WO 2008/045380 | 4/2008 |
| WO | WO 2008/054543 | 5/2008 |
| WO | WO 2008/076368 | 6/2008 |
| WO | WO 2008/109176 | 9/2008 |
| WO | WO 2008/130629 | 10/2008 |
| WO | WO 2009/032167 | 3/2009 |
| WO | WO 2010/025310 A2 | 3/2010 |
| WO | WO 2010/070295 | 6/2010 |
| WO | WO 2010/115100 | 10/2010 |
| WO | WO 2010/115154 A1 | 10/2010 |
| WO | WO 2011/056872 | 5/2011 |
| WO | WO 2011/066185 | 6/2011 |
| WO | WO 2011/066186 | 6/2011 |
| WO | WO 2011/085075 | 7/2011 |
| WO | WO 2011/143556 | 11/2011 |
| WO | WO 2011/150168 | 12/2011 |
| WO | WO 2011/161413 | 12/2011 |
| WO | WO 2012/064975 | 5/2012 |
| WO | WO 2012/078312 | 6/2012 |
| WO | WO 2012/084923 | 6/2012 |
| WO | WO 2012/174337 | 12/2012 |
| WO | WO 2013/017950 A1 | 2/2013 |
| WO | WO 2013/032850 | 3/2013 |
| WO | WO 2013/163263 | 10/2013 |
| WO | WO 2014/004393 | 1/2014 |
| WO | WO 2014/089290 A1 | 6/2014 |
| WO | WO 2014/093694 | 6/2014 |

(56) References Cited

FOREIGN PATENT DOCUMENTS

| | | |
|---|---|---|
| WO | WO 2014/144288 A1 | 9/2014 |
| WO | WO 2014/151696 | 9/2014 |
| WO | WO 2014/160004 | 10/2014 |
| WO | WO 2014/160059 | 10/2014 |
| WO | WO 2014/191518 A1 | 12/2014 |
| WO | WO 2015/017527 | 2/2015 |
| WO | WO 2015/035162 A1 | 3/2015 |
| WO | WO 2015/081114 | 6/2015 |

OTHER PUBLICATIONS

Abremski et al. Bacteriophage Pl site-specific recombination. Purification and properties of the Cre recombinase protein (1984) J. Mol. Biol. 259: 1509-1514.

Abremski et al. Studies on the properties of P 1 site-specific recombination: evidence for topologically unlinked products following recombination. Cell 32:1301-1311 (1983).

Adessi et al., Solid phase DNA amplification: characterisation of primer attachment and amplification mechanisms, Nucleic Acids Research, 28(20):E87, (Oct. 15, 2000).

Afshari et al. Application of Complementary DNA Microarray Technology to Carcinogen Identification, Toxicology, and Drug Safety. Cancer Research, 59, 4759-4760, Oct. 1, 1999.

Aihara et al. A Conformational Switch Controls the DNA Cleavage Activity of .lamda. Integrase, Molecular Cell, 12:187-198, (Jul. 2003).

Akhundova et al. RNA synthesis on immobilized DNA templates in vitro. Biochemistry—Moscow, 43(5):626-628 (1978).

Altschul et al. Basic local alignment search tool, J Mol Biol., 215(3):403-10, (1990).

Altschul et al., Iterated profile searches with PSI-BLAST—a tool for discovery in protein databases, Trends Biochem. Sci., 23:444-447, (Nov. 1998).

Andersen et al. New Unstable Variants of Green Fluorescent Protein for Studies of Transient Gene Expression in Bacteria, Applied and Environmental Microbiology, 64(6):2240-2246 (Jun. 1998).

Ashkin A., Applications of laser radiation pressure Science, 210(4474): 1081-1088, (Dec. 5, 1980).

Aslanzadeh, Brief Review: Preventing PCR Amplification Carry-over Contamination in a Clinical Laboratory. Annals of Clinical & Laboratory Science 34(4) :389 (2004).

Au et al. Gene Synthesis by a LCR-Based Approach: High Level Production of Leptin-L54 Using Synthetic Gene in Escherichia coli, Biochemical and Biophysical Research Communications, 248:200-203 (1998).

Babineau et al. The FLP Protein of the 2 micron Plasmid of Yeast (1985) J. Biol. Chem. 260: 12313-12319.

Bar et al., Dendrimer-modified silicon oxide surfaces as platforms for the deposition of gold and silver colloid monolayers: preparation method, characterization, and correlation between microstructure and optical properties, Langmuir, 12(5): 1172-1179, (Mar. 6, 1996).

Bartsevich et al. Engineered Zinc Finger Proteins for Controlling Stem Cell Fate, Stem Cells, 21:632-637 (2003).

Beer et al., On-chip, real time single-copy polymerase chain reaction in picoliter droplets, Analytical Chemistry, 79(22):8471-8475, (Nov. 15, 2007).

Beier et al., Analysis of DNA-microarray produced by inverse in situ oligonucleotide synthesis. J. Biotechnology, 94:15-22 (2002).

Bennett, Solexa Ltd., Pharmacogenomics, 5(4):433-8, (Jun. 2004).

Berlin Y. A. DNA splicing by directed ligation (SDL), Current Issues Molec. Biol. 1:21-30, 1999.

Bethell et al. From monolayers to nanostructured materials: an organic chemist's view of self-assembly, J. Electroanal. Chem., 409:137-143, (1996).

Binkowski et al. Correcting erros in synthetic DNA through consensus shuffling Nucl. Acids Res., vol. 33, No. 6, e55, 2005.

Blanchard, Synthetic DNA Arrays, Genetic Engineering, 20:111-123, Plenum Press, (1998).

Boal et al. Cleavage of oligodeoxyribonucleotides from controlled-pore glass supports and their rapid deprotection by gaseous amines, NAR, 24(15):3115-3117, (1996).

Boltner et al. R391: A Conjugative Integrating Mosaic Comprised of Phage, Plasmid, and Transposon Elements, J. of Bacteriology, 184(18):5158-5169 (Sep. 2002).

Booth et al. Assembly and cloning of coding sequences for neurotrophic factors directly from genomic DNA using polymerase chain reaction and uracil DNA glycosylase, Gene, 146(2):303-308 (1994).

Braatsch et al., Escherichia coli strains with promoter libraries constructed by Red/ET recombination pave the way for transcriptional fine-tuning, Biotechniques. 2008;45(3):335-337.

Brown, C. BioBricks to help reverse-engineer life, URL: http://eetimes.com/news/latest/showArticle.ihtml?articleID=21700333, (Jun. 11, 2004).

Burge et al., Prediction of complete gene structures in human genomic DNA, J Mol Biol., 268(1):78-94, (1997).

Cai et al. Immunogenicity of Polyepitope Libraries Assembled by Epitope Shuffling: An Approach to the Development of Chimeric Gene Vaccination Against Malaria, Vaccine, 23:267-277, (2004).

Carr, P., et al. Protein-mediated error-correction for de novo DNA synthesis, Nucleic Acids Research, 32(20), e162 (9 pages), (2004).

Caruthers, et al. CXV. Total synthesis of the structural gene for an alanine transfer RNA from yeast. Enzymic joining to form the total DNA duplex, J Mol Biol., 72(2):475-92, (Dec. 28, 1972).

Cassell et al., Mechanism of Inhibition of Site-specific Recombination by the Holliday Junction-trapping Peptide WKHYNY: Insights into Phage I integrase-mediated Strand Exchange, J. Mol. Biol., 327:413-429, (2003).

Chakrabarti et al., Novel Sulfoxides facilitate GC-rich template amplification., 2002, BioTechniques 32(4):866-873.

Chalmers et al., Scaling up the ligase chain reaction-based approach to gene synthesis, BioTechniques, 30(2):249-252, (Feb. 2001).

Chan et al. Refactoring bacteriophage T7, Molecular Systems Biol., doi: 10.1038/msb4100025, (Published online Sep. 13, 2005).

Chandrasegara et al. Chimeric Restriction Enzymes: What is Next?, Biol. Chem., 380:841-848 (1999).

Chang et al. Evolution of a cytokine using DNA family shuffling, NatureBiotechnology, 17: 793-797(1999).

Che, A. BioBricks++: Simplifying Assembly of Standard DNA Components, [Online] XP002412778, URL: http://austinche.name/docs/bbpp.pdf, (Jun. 9, 2004).

Chen et al. A new method for the synthesis of a structural gene, Nucleic Acids Research, 18(4):871-878 (Feb. 1990).

Cherepanov et al. Joining of short DNA oligonucleotides with base pair mismatches by T4 DNA ligase, J Biochem., 129(1):61-68, (Jan. 2001).

Chetverin et al., Sequencing pool of Nucleic Acids on Oligonucleotide arrays, Biosystems, 30:215-231, (1993).

Chevalier et al. Design, Activity, and Structure of a Highly Specific Artificial Endonuclease, Molecular Cell, 10:895-905 (Oct. 2002).

Chevalier et al., Homing endonucleases: structural and functional insight into the catalysts of intron/intein mobility, Nucl. Acids Res., 29(18):3757-3774 (2001).

Cho et al. Creating, transporting, cutting and merging liquid droplets by electrowetting-based actuation for digital microfluidic circuits, J. of Microelectromechanical Systems, 12(1):70-80, (Feb. 2003).

Christians et al. Directed evolution of thymidine kinase for AZT phosphorylation using DNA family shuffling, Nature Biotechnology, 17:259-264(1999).

Coco et al. Growth Factor Engineering by Degenerate Homoduplex Gene Family Recombination, Nature Biotechnology, 20:1246-1250, (Dec. 2002).

Colvin et al. Semiconductor nanocrystals covalently bound to metal surfaces with self-assembled monolayers, J. Am. Chem. Soc., 114(13):5221-5230, 1992.

Crameri et al. DNA shuffling of a family of genes from diverse species accelerates directed evolution, Nature, 391:288-291(1998).

Crameri et al. Molecular evolution of an arsenate detoxification pathway by DNA shuffling, Nature Biotechnology, 15:436-438 (1997).

(56) References Cited

OTHER PUBLICATIONS

Crameri, A., et al. Improved Green Fluorescent Protein by Molecular Evolution Using DNA Shuffling, Nature Biotechnology, 14:315-319, (Mar. 1996).
Cui T. et al. Sepharose-supported DNA as template for RNA synthesis J. Biotechnology, 66: 225-228 (1998).
Dafhnis-Calas, F., et al. Iterative in vivo assembly of large and complex transgenes by combining the activities of <DC31 integrase and Cre recombinase, Nucleic AcidsResearch, 33(22): 1-14 (2005).
Datsenko K.A. et al. One-step inactivation of chromosomal genes in Escherichia coli K-12 using PCR products PNAS (2000) 97: 6640-6645.
Dedkova, L. et al. Enhanced D-Amino Acid Incorporation into Protein by modified Ribosomes, J. Am. Chem. Soc., 125:6616-6617, (2003).
Demeler et al. Neural network optimization for E.coli promoter prediction, Nucl. Acids. Res. 19:1593-1599 (1991).
Dillon, P.J. et al., A Rapid Method for the Construction of Synthetic Genes Using the Polymerase Chain Reaction, Biotechniques, vol. 9, No. 3, pp. 298-300, 1990.
Doyon et al., Enhancing zinc-finger-nuclease activity with improved obligate heterodimeric architectures. Nat Methods. Jan. 2011;8(1):74-9. doi:10.1038/nmeth.1539. Epub Dec. 5, 2010.
Duggan et al., Expression Profiling Using cDNA Microarrays, Nat. Genet. S21:10-14 (1999).
Ellson, Picoliter: Ennabling Precise Transfer of Nanoliter and Picoliter Volumes. Drug Discovery Today 7(5 Suppl.) :s32 (2002).
Elowitz et al., A synthetic oscillatory network of transcriptional regulators. Nature. 2000;403;335-338.
Engler C. et al. A one pot, one step, precision cloning method with high throughput capability PLoS One, 3: e36471.
Engler C. et al. Golden Gate Shuffling: a one-pot DNA shuffling method based on type IIS restriction enzymes PLoS One, 4:e5553, 2009.
Evans et al., Roles for Mismatch Repair Factors in Regulating Genetic Recombination, Molecular & Cellular Biology, 20(21):7839-7844 (Nov. 2000).
Ferretti, L. et al. Total synthesis of a gene for bovine rhodopsin, PNAS, 83:599-603 (Feb. 1986).
Ferrin, L.J., et al. Sequence-specific ligation of DNA using RecA protein, Proc. Natl. Acad. Sci. USA, 95: 2152-2157 (1998).
Fidalgo et al., Surface induced droplet fusion in microfluidic devices, Lab on Chip, 7(8)984-986, (2007).
Fisch, I. et al. A Strategy of Exon Shuffling for Making Large Peptide Repertoires Displayed on Filamentous Bacteriophage, Proceedings of the National Academy of Sciences of USA, 93:7761-7766, (Jul. 1996).
Flanagan et al. Analysis of inhibitors of the site-specific recombination reaction mediated by Tn3 resolvase (1989) J. Mol. Biol. 206: 295-304.
Fleck et al., DNA Repair, J. Cell Science, 117(4):515-517 (2004).
Fodor et al., Light-directed, spatially addressable parallel chemical synthesis, Science, 251(4995):767-773, (Feb. 15, 1991).
Fujita et al., Surprising liability of biotin-streptavidin bond during transcription of biotinylated DNA bound to paramagnetic streptavidin beads. Bio Techniques, 14:608-617 (1993).
Fullwood et al., Next-generation DNA sequencing of paired-end tags (PET) for transcriptome and genome analyses. Genome Res. Apr. 2009;19(4):521-32. doi: 10.1101/gr.074906.107.
Gabsalilow et al., Site- and strand-specific nicking of DNA by fusion proteins derived from MutH and I-SceI or TALE repeats. Nucleic Acids Res. Apr. 2013;41(7):e83. doi: 10.1093/nar/gkt080. Epub Feb. 13, 2013.
Gao, X. et al. Thermodynamically balanced inside-out (TBIO) PCR-based gene synthesis: a novel method of primer design for high fidelity assembly of longer gene sequences, Nucleic Acids Research, 31(22):e143 (11 pages) (2003).
Gardner, T., et al. Construction of a genetic toggle switch in Escherichia coli, Nature, 403(20):339-342 (Jan. 2000).
Gasiunas et al., Cas9-crRNA ribonucleoprotein complex mediates specific DNA cleavage for adaptive immunity in bacteria. Proc Natl Acad Sci U S A. Sep. 25, 2012;109(39):E2579-86. Epub Sep. 4, 2012.
Gibbs, W. Synthetic Life, Scientific American, [Online] URL: htto://www.sciam.com/orintversion.cfm?articleID=0009FCA4, (Apr. 26, 2004).
Glasgow A.C. et al. DNA-binding properties of the Hin recombinase (1989) J. Biol. Chem. 264: 10072-10082.
Goler, J. BioJADE: A Design and Simulation Tool for Synthetic Biological Systems, MIT Computer Science and Artificial Intelligence Laboratory, AI Technical Report, [Online] URL:http://dspace.mit.edu/bitstream/1721.1/30475/2/MIT-CSAIL-TR-2004-036.pdf, (May 2004).
Grabar, K., et al., Preparation and Characterization Monolayers, Anal. Chem., 67:735-743, (1995).
Greenberg et al., Cleavage of oligonucleotides from solid-phase support using o-nitrobenzyl photochemistry, J. of Org. Chem., 59(4):746-753, (Feb. 1994).
Grifith et al., Coordinating Multiple Droplets in Planar Array Digital Microfluidic Systems, The International Journal of Robotics Research, 24(11):933-949, (Nov. 2005).
Gronostajski et al., The FLP protein of the 2 micron plasmid of yeast (1985) J. Biol. Chem. 260: 12328-12335.
Guilinger et al., Fusion of catalytically inactive Cas9 to FokI nuclease improves the specificity of genome modification. Nat Biotechnol. Jun. 2014;32(6):577-582. doi: 10.1038/nbt.2909. Epub Apr. 25, 2014.
Gulati et al. Opportunities for microfluidic technologies in synthetic biology. Journal of the Royal Society, vol. 6, Suppl. 4, pp. S493-S506, (2009).
Guntas, G., et al. A molecular switch created by in vitro recombination of nonhomologous genes, Chem. & Biol., 11:1483-1487 (Nov. 2004).
Guntas, G., et al. Directed Evolution of Protein Switches and Their Application to the Creation of Ligand-Binding Proteins, Proc. Natl. Acad. Sci. USA, 102(32):11224-11229 (Aug. 9, 2005).
Gupta, N., et al. Studies on Polynucleotides, LXXXVIII. Enzymatic Joining of Chemically Synthesized Segments Corresponding to the Gene for Alanine-tRNA, PNAS, 60:1338-1344, (1968).
Hacia J.G. et al. Applications of DNA chips for genomic analysis. Mol Psychiatry. Nov. 1998;3(6):483-92.
Hacia J.G. Resequencing and mutational analysis using oligonucleotide microarrays, Nature Genetics, 21(1 suppl):42-47, 1999.
Haeberle et al., Microfluidic platforms for lab-on-chip applications, Lab on a Chip 7(9):1094-1110, (2007).
Haffter et al. Enhancer independent mutants of the Cin recombinase have a relaxed topological specificity. (1988) EMBO J. 7:3991-3996.
Hansen et al., Review of Mammalian DNA Repair and Transcriptional Implications, J. Pharmacol. & Exper. Therapeutics, 295(1):1-9, (2000).
Hardy et al., Reagents for the preparation of two oligonucleotides per synthesis (TOPSTM), Nucleic Acids Research, 22(15):2998-3004, (1994).
Hawley et al., Compilation and analysis of Escherichia coli promoter DNA sequences Nucl. Acid. Res. 11:2237-2255. 1983.
Hecker, K. Error Analysis of Chemically Synthesized Polynucleotides, BioTechniques, 24(2):256-260, (Feb. 1998).
Heeb, S., et al. Small, Stable Shuttle Vectors Based on the Minimal pVS1 Replicon for Use in Gram-Negative Plant-Associated Bacteria, MPMI, 13(2):232-237 (2000).
Henegariu et al. Multiplex PCR: critical parameters and step-by-step protocol Biotechniques, 23(3): 504-511, (Sep. 1997).
Hermeling, S., et al. Structure-Immunogenicity Relationships of Therapeutic Proteins, Pharmaceutical Research, 21(6):897-903, (Jun. 2004).
Higuchi, R., et al. A general method of in vitro preparation and specific mutagenesis of DNA fragments: study of protein and DNA interactions, Nucleic Acids Research, 16(15):7351-7367 (1988).
Hoess et al., Mechanism of strand cleavage and exchange in the Cre-lox site-specific recombination system (1985) J. Mol. Biol. 181: 351-362.

(56) References Cited

OTHER PUBLICATIONS

Hoess R.H. et al. Interaction of the bacteriophage P 1 recombinase Cre with the recombining site loxP (1984) Proc. Natl. Acad. Sci. USA 81: 1026-1029.

Hoess R.H. et al. P 1 site-specific recombination: nucleotide sequence of the recombining sites (1982) Proc. Natl. Acad. Sci. USA 79: 3398-3402.

Hoess R.H. et al. The role of the loxP spacer region in PI site-specific recombination (1986), Nucleic Acids Res. 14: 2287-2300.

Holmes, Model studies for new o-nitrobenzyl photolabile linkers: substituent effects on the rates of photochemical cleavage, J. of Org. Chem., 62(8):2370-2380, (Apr. 18, 1997).

Hoover et al., DNAWorks: an automated method for designing oligonucleotides for PCR-based gene synthesis, Nucleic Acids Research, 30(10):e43 (7 pages), (2002).

Horton, R., et al. Engineering hybrid genes without the use of restriction enzymes: Gene splicing by overlap extension, Gene, 77:61-68, (1989).

Hyman, A new method of sequencing DNA, Analytical Biochemistry, 174(2):423-436, (Nov. 1, 1988).

Ibrahim, E., et al. Serine/arginine-rich protein-dependent suppression of exon skipping by exonic splicing enhancers, Proc. Natl. Acad. Sci. U S A, 102(14):5002-5007, (Apr. 5, 2005).

Ito R. et al. Novel muteins of human tumor necrosis factor alpha Biochimica et Biophysica Acta, 1096 (3): 245-252 (1991).

Jayaraman et al. Polymerase chain-reaction mediated gene synthesis: synthesis of a gene coding for Isozyme C of Horseradish Peroxidase PNAS 88:4084-4088, (May 1991).

Jayaraman, et al. A PCR-mediated Gene synthesis strategy involving the assembly of oligonucleotides representing only one of the strands, Biotechniques, 12(3):392-398, (1992).

Jensen P.R. et al. The sequence of spacers between the consensus sequences modulates the strength of prokaryotic promoters Appl. Env. Microbiol. 64:82-87, 1998.

Jinek et al., A programmable dual-RNA-guided DNA endonuclease in adaptive bacterial immunity. Science. Aug. 17, 2012;337(6096):816-21. doi: 10.1126/science.1225829. Epub Jun. 28, 2012.

Johnston M. Gene chips: Array of hope for understanding gene regulation. Current Biology, 8: (5) R171, 1998.

Jones, T.D., et al. The Development of a Modified Human IFN-alpha2b Linked to the Fc Portion of Human IgG1 as a Novel Potential Therapeutic for the Treatment of Hepatitis C Virus Infection, Journal of Interferon & Cytokine Research, 24:560-572,(2004).

Kahl et al. Solution-Phase Bioconjugate Synthesis Using Protected Oligonucleotides Containing 3'-Alkyl Carboxylic Acids, J. of Org. Chem., 64(2):507-510, (1999).

Kahl et al., High-Yielding Method for On-Column Derivatization of Protected Oligodeoxy-nucleotides and Its Application to the Convergent Synthesis of 5',3'-Bis-conjugates, J. of Org. Chem., 63(15):4870.

Kampke et al., Efficient primer design algorithms. Bioinformatics, 2001;17(3):214-225.

Kelly et al., Miniaturizing chemistry and biology in microdroplets, Chem. Commun., 1773-1788, (2007).

Khaitovich, P., et al. Characterization of functionally active subribosomal particles from Thermus aquaticus, Proc. Natl. Acad. Sci., 96:85-90 (Jan. 1999).

Kim et al., Precision genome engineering with programmable DNA-nicking enzymes. Genome Res. Jul. 2012;22(7):1327-33. doi:10.1101/gr.138792.112. Epub Apr. 20, 2012.

Kim J.H. et al. Solid-phase genetic engineering with DNA immobilized on a gold surface. J. Biotechnology, 96:213-221. (2002).

Kim, C., et al. Biological lithography: Improvements in DNA synthesis methods, J. Vac. Sci. Technol. B 22(6):3163-3167 (2004).

Kim, Y., et al. Insertion and Deletion Mutants of FokI Restriction Endonuclease, J. Biol. Chem., 269(50):31978-31982 (1994).

Kinde et al., Detection and quantification of rare mutations with massively parallel sequencing. Proc Natl Acad Sci U S A. Jun. 7, 2011;108(23):9530-5. doi: 10.1073/pnas.1105422108. Epub May 17, 2011. Supplemental Information.

Kisselev, L., et al. Termination of translation: interplay of mRNA, rRNAS and release factors?, The EMBO J., 22(2):175-182, (2003).

Kitamura, K. et al. Construction of Block-Shuffled Libraries of DNA for Evolutionary Protein Engineering: Y-Ligation-Based Block Shuffling. Protein Engineering, 15(10): 843-853, (Oct. 2002).

Kleppe K., et al. Studies of polynucleotides: repair replication of short synthetic DNA's as catalyzed by DNA polymerases, J. Mol. Biol. 56:341-361, (1971).

Kodumal., S., et al. Total synthesis of long DNA sequences: Synthesis of a contiguous 32-kb polyketide synthase gene cluster, PNAS, 101(44):15573-15578, (Nov. 2, 2004).

Kolisnychenko, V., et al. Engineering a Reduced *Escherichia coli* Genome, Genome Research, 12:640-647, (2002).

Kong et al., Parallel gene synthesis in microfluidic device, Nucleic Acids Research, vol. 35, No. 8, pp. e61-e71 (9 pages), (2007).

Kosuri et al. (Scalable gene synthesis by selective amplification of DNA pools from high-fidelity microchips, Nature Biotechnology 28, 1295-1299 (2010), Published online Nov. 28, 2010).

Kotsopoulou, E., et al. A Rev-Independent Human Immunodeficiency Virus Type 1 (HIV-1)-Based Vector That Exploits a Codon-Optimized HIV-1 gag-pol Gene, Journal of Virology, 74(10):4839-4852, (May 2000).

Kowalczykowski, S. In vitro reconstitution of homologous recombination reactions, Experientia, 50:204-215, (1994).

Kowalczykowski, S. Initiation of genetic recombination and recombination-dependent replication, TIBS, 25:156-165, (Apr. 2000).

Krieg et al., Real-time detection of nucleotide incorporation during complementary DNA strand analysis Chem. Bio. Chem. 4:589-592 (2003).

Kurian et al. DNA chip technology. J Pathol.; 187(3):267-71, (Feb. 1999).

Lamers, M., et al. ATP Increases the Affinity between MutS ATPase Domains, J. Biol. Chem., 279(42):43879-43885, (Oct. 15, 2004).

Lashkari et al. An automated multiplex oligonucleotide synthesizer: Development of high throughput, low cost DNA synthesis. PNAS 92(17): 7912-7915, (1995).

Leamon et al., A massively parallel PicoTiterPlate™ based platform for discrete picoliter-scale polymerase chain reactions, Electrophoresis, 24(21):3769-3777, (Nov. 2003).

Lebedenko E.N. et al. Method of artificial DNA splicing by directed ligation Nucleic Acids Research, 19: 6757-6761, 1991.

Lederman et al., DNA-directed peptide synthesis. 1. A comparison of T2 and *Escherichia coli* DNA-directed peptide synthesis in two cell-free systems. Biochim Biophys Acta. Nov. 21, 1967;149(1):253-8.

Lee, K., et al. Genetic approaches to Studying Protein Synthesis: Effects of Mutations at .psi.1516 and A535 in *Escherichia coli* 16S rRNA, J. Nutr., 131:2994S-3004S, (2001).

Leslie et al., Site-specific recombination in the replication terminus region of *Escherichia coli*: functional replacement of dif. (1995) EMBO J. 14: 1561-1570.

Lewis et al. Gene modification via plug and socket gene targeting. J Clin Invest. Jan. 1, 1996;97(1):3-5.

Lewis et al., Control of directionality in integrase-mediated recombination: examination of recombination directionality factors (RDFs) including Xis and Cox proteins, Nucl. Acids Res., 29(11):2205-2216 (2001).

Li et al., Alteration of the cleavage distance of Fok I restriction endonuclease by insertion mutagenesis. Proc Natl Acad Sci U S A, 90:2764-2768, (Apr. 1993).

Li et al., Ligation independent cloning irrespective of restriction site compatibility, Nucl. Acids Res., 25(20):4165-4166, (1997).

Link, A., et al. Methods for generating precise deletions and insertions in the genome of wild-type *Escherichia coli*: Application to open reading frame characterization, J. Bacteriol., 179(20):6228-6237, (Oct. 1997).

Liu et al., DNA ligation of ultramicrovolume using EWOD microfluidic system with coplanar electrodes: DNA ligation of ultramicrovolume using a EWOD microfluidic system, J. of Micromechanics and Microengineering, 18(4):45017 (7 pages), (2008).

Liu G. et al. DNA computing on surfaces. Nature, 403: 175-179 (2000).

(56) References Cited

OTHER PUBLICATIONS

Liu, W. et al. Genetic Incorporation of Unnatural Amino Acids Into Proteins in Mammalian Cells, Nature Methods, 4(3):239-244, (Mar. 2007).
Lu et al., Conjugative transposition: Tn916 integrase contains two independent DNA binding domains that recognize different DNA sequences '(1994) EMBO J. 13: 1541-1548.
Luo, P., et al. Development of a Cytokine Analog with Enhanced Stability Using Computational Ultrahigh Throughput Screening, Protein Science, 11:1218-1226, (2002).
Lutz, S., et al. Homology-Independent Protein Engineering, Current Opinion in Biotechnology, 11(4):319-324, (Aug. 2000).
Mandecki et al. FokI method of gene synthesis Gene, 68:101-107 (1988).
Mandecki W. Oligonucleotide-directed double-strand break repair in plasmids of Escherichia coli: A method for site-specific mutagenesis. 1986, PNAS, 83 :7177-7181.
Mannervik, B. Optimizing the Heterologous Expression of Glutathione Transferase, Methods in Enzymology, 401:254-265, (2005).
Margulies et al., Genome Sequencing in Microfabricated High-Density Picolitre Reactors, Nature. 437: 376-380 (2005). Supplemental materials.
Matzas et al. (High-fidelity gene synthesis by retrieval of sequence-verified DNA identified using high-throughput pyrosequencing, Nature Biotechnology 28, 1291-1294 (2010), Published online Nov. 28, 2010).
McCaughan et al., Single-Molecule Genomics, The Journal of Pathology, 220: 297-306, (Jan. 1, 2009).
McClain et al., Genome Sequence Analysis of Helicobacter Pylori Strains Associated with Gastric Ulceration and Gastric Cancer, BMC Genomics, Biomed Central Ltd, London, IK. 10(1):3 (2009).
McGall et al., Light-Directed Synthesis of High-Density Oligonucleotide Arrays Using Semiconductor Photoresists, Pro. Natl. Acad. Sci. 93(24):13555-13560 (1996).
Mei et al., Cell-Free Protein Synthesis in Microfluidic Array Devices, Biotechnol. Prog. 2007, 23:1305-1311.
Mercier. J. et al. Structural and functional characterization of tnpI, a recombinase locus in Tn21 and related beta-lactamase transposons. (1990) J. Bacteriol. 172: 3745.
Metzker et al., Termination of DNA synthesis by novel 3'-modified-deoxyribonucleoside 5'-triphosphates, NAR, 22(20):4259-4267, (1994).
Metzker, Emerging technologies in DNA sequencing. Genome Res. Dec. 2005;15(12):1767-76.
Meyer-Leon et al. Purification of the FLP site-specific recombinase by affinity chromatography and re-examination of basic properties of the system (1987) Nucleic Acids Res. 15: 6469.
Mezard, C., et al. Recombination Between Similar But Not Identical DNA Sequences During Yeast Transformation Occurs Within Short Stretches of Identity, Cell, 70:659-670, (Aug. 21, 1992).
Miick, S., et al. Crossover isomer bias is the primary sequence-dependent property of immobilized Holliday junctions, Proc. Natl. Acad. Sci. USA, 94:9080-9084, (Aug. 1997).
Milton, R., et al. Total Chemical Synthesis of a D-Enzyme: The Enantiomers of HIV-1 Protease Show Demonstration of Reciprocal Chiral Substrate Specificity, Science, 256:1445-1448, (Jun. 5, 1992).
Mir K. U. et al. Sequencing by cyclic ligation and cleavage (CycLic) directly on a microarray captured template. Nucl. Acids Rse. vol. 37, No. 1 e5, 2008.
Mitra et al., Fluorescent in situ Sequencing on Polymerase Colonies, Analytical Biochemistry. 320:55-65 (2003).
Modrich, P. Strand-specific Mismatch Repair in Mammalian Cells, J. Biol. Chem., 272(40): 24727-24730, (Oct. 3, 1997).
Moffitt et al., Recent Advances in Optical Tweezers. Annual Review of Biochemistry 77 :205 (Feb. 2008).
Moore et al., Computational Challenges in Combinatorial Library Design for Protein Engineering, AIChE Journal, 50(2):262-272, (Feb. 2004).
Morton, Life, Reinvented. Wired. 2009. Retrieved from http://archive.wired.com/wired/archive/13.01/mit_pr.html on Aug. 14, 2015.

Muller, Ten years of gene targeting: targeted mouse mutants, from vector design to phenotype analysis. Mech Dev. Apr. 1999;82(1-2):3-21.
Nakamaye, K., et al. Direct sequencing of polymerase chain reaction amplified DNA fragments through the incorporation of deoxynucleoside-thiotriphosphates, Nucleic Acids Research, 16(21):9947-9959, (1988).
Nakamura et al., How protein reads the stop codon and terminates translation, Genes to Cells, 3:265-278, (1998).
Nakayama et al., A system using convertible vectors for screening soluble recombinant proteins produced in Escherichia coli from randomly fragmented cDNAs, Bioch. and Biophys. Res. Comm., 312:825-830, (2003).
Ness, J., et al. DNA shuffling of subgenomic sequences of subtilisin, Nature Biotechnology 17: 893-896 (1999). Abstract only.
Ness, J., et al. Synthetic Shuffling Expands Functional Protein Diversity by Allowing Amino Acids to Recombine Independently Nature Biotechnology, 20:1251-1255, (Dec. 2002).
Neuman et al., Optical trapping. Rev Sci Instrum. Sep. 2004;75(9):2787-809.
Nilsson P., et al. Real-Time monitoring of DNA manipulations using biosensor technology, Analytical Biochemistry, 224:400-408, (1995).
Nilsson, L., et al. Improved Heterologous Expression of Human Glutathione Transferase A4-4 by Random Silent Mutagenesis of Codons in the 5' Region, Biochemica et Biophysica Acta, 1528: 101-106, (2001).
Noirot et al., DNA Strand Invasion Promoted by Escherichia coli RecT Protein, J. Biol. Chem., 273(20):12274-12280, (May 15, 1998).
Novy, R., et al. Ligation Independent Cloning: Efficient Directional Cloning of PCR Products, Novagen, Inc., InNovations, 5:1-3, http://www.emdbiosciences.com/html/NVG/inNovations.html), (1996).
Orban P.C. et al. Tissue- and site-specific DNA recombination in transgenic mice (1992) Proc. Natl. Acad. Sci. 89: 6861-6865.
Osawa, S., et al. Recent Evidence for Evolution of the Genetic Code, Microbiological Reviews, 56(1):229-264, (Mar. 1992).
Osborn et al., When phage, plasmids, and transposons collide: genomic islands, and conjugative and mobilizable-transposons as a mosaic continuum, Plasmid, 48:202-212, (2002).
Pachuk C.J. et al. Chain reaction cloning: one step method for directional ligation of multiple DNA fragments Gene, 243(1-2): 19-25 (2000).
Padgett et al .. Creating seamless junctions independent of restriction sites in PCR cloning, Gene, Feb. 2, 1996, vol. 168, No. 1, pp. 31-35.
Pan et al., An approach for global scanning of single nucleotide variations, PNAS, 99(14):9346-9351, (Jul. 9, 2002).
Panet et al., Studies of polynucleotides: the linkage of deoxyribopolynucleotides templates to cellulose and its use in their replication. J. Biol. Chem. 249(16):5213-5221 (1974).
Parr et al., New donor vector for generation of histidine-tagged fusion proteins using the Gateway Cloning System, Plasmid, 49:179-183, (2003).
Pemov et al., DNA analysis with multiplex microarray-enhanced PCR. Nucleic Acids Res. Jan. 20, 2005;33(2):e11.
Peters et al., Tn7: Smarter Than We Thought, Nature, 2:806-814, (Nov. 2001).
Petrik et al., Advances in Transfusion Medicine in the First Decade of the 21.sup.st Century: Advances in Miniaturized Technologies, Transfusion and Apheresis Science. 45(1): 45-51 (2011).
Pon, Solid-phase supports for oligonucleotide synthesis, Methods Mol. Biol., 20:465-496, (1993).
Posfai, G., et al. In vivo excision and amplification of large segments of the Escherichia coli genome, Nucl. Acids Res., 22(12):2392-2398, (1994).
Posfai, G., et al. Markerless gene replacement in Escherichia coli stimulated by a double-strand break in the chromosome, Nucl. Acids Res., 27(22):4409-4415, (1999).
Prodromou et al., Recursive PCR: A Novel Technique for Total Gene Synthesis Protein Engineering, 5(8):827-829 (1992).
Ramachandran et al., End-Point Limiting-Dilution Real-Time PCR Assay for Evaluation of Hepatitis C Virus Quasispecies in Serum:

(56) References Cited

OTHER PUBLICATIONS

Performance Under Optimal and Suboptimal Conditions, Journal of Virological Methods. 151(2): 217-224 (2008).
Ramirez et al., Engineered zinc finger nickases induce homology-directed repair with reduced mutagenic effects. Nucleic Acids Res. Jul. 2012;40(12):5560-8. doi: 10.1093/nar/gks179. Epub Feb. 28, 2012.
Randegger et al., Real-time PCR and melting curve analysis for reliable and rapid detection of SHV extended-spectrum beta-lactamases. Antimicrob Agents Chemother. Jun. 2001;45(6):1730-6.
Regalado, A. Next Dream for Venter: Create Entire Set of Genes From Scratch, Wall Street Journal, A1, (Jun. 29, 2005).
Reyrat, J., et al. Counterselectable Markers: Untapped Tools for Bacterial Genetics and Pathogenesis, Infection and Immunity, 66(9):4011-4017, (Sep. 1998).
Richmond, K., et al., Amplification and assembly of chip-eluted DNA (AACED): a method for high-throughput gene synthesis, Nucleic Acids Research, 32(17): 5011-5018 (2004).
Roberts et al., RNA-peptide fusions for the in vitro selection of peptides and proteins, Proc Natl Acad Sci USA. 94(23): 12297-302, 1997.
Rouillard, J. et al. Gen2Oligo: Oligonucleotide design for in vitro gene synthesis, Nucleic Acids Research, 32: W176-W180, (2004).
Rouwendal, G., et al. Enhanced Expression in Tobacco of the Gene Encoding Green Fluorescent Protein by Modification of its Codon Usage, Plant Molecular Biology, 33:989-999, (1997).
Ryu, D.D.Y., et al. Recent Progress in Biomolecular Engineering, Biotechnol. Prog. 16:2-16 (2000).
Sa-Ardyen, P., et al. The flexibility of DNA double crossover molecules, Biophys. J., 84:3829-3837, (Jun. 2003).
Saha et al., The promoter of the Chinese hamster ovary dihydrofolate reductase gene regulates the activity of the local origin and helps define its boundaries. Genes Dev. Feb. 15, 2004;18(4):397-410. Epub Feb. 20, 2004.
Saiki, R., et al. Analysis of enzymatically amplified beta-globin and HLA-DQ alpha DNA with allele-specific oligonucleotide probes, Nature, 324(6093):163-166, (Nov. 13, 1986).
Sakabe, N., et al. A Bioinformatics Analysis of Alternative Exon Usage in Human Genes Coding for Extracellular Matrix Proteins, Genetics and Molecular Research, 3(4):532-544, (2004).
Sakamoto, K., et al. Site-Specific Incorporation of an Unnatural Amino Acid Into Proteins in Mammalian Cells, Nucleic Acids Research, 30(21):4692-4699, (2002).
Saks, M. Making sense out of nonsense, PNAS, 98(5):2125-2127, (Feb. 27, 2001).
Saks, M., et al. An Engineered Tetrahymena tRNA.sup.Gln, for in Vivo Incorporation of Unnatural Amino Acids into Proteins by Nonsense Suppression, J. of Biol. Chem., 271(38):23169-23175, (Sep. 20, 1996).
Salyers, A., et al. Conjugative Transposons: an Unusual and Diverse Set of Integrated Gene Transfer Elements, Microbiological Reviews, 59(4):579-590, (Dec. 1995).
Sanjana, N. et al., A Transcription activator-like effector toolbox for genome engineering, Nature Protocols, Nature Publishing Group. Jan. 1, 2012;7(1):171-192.
Sato et al. The cisA cistron of Bacillus subtilis sporulation gene spoIVC encodes a protein homologous to a site-specific recombinase (1990) J. Bacteriol. 172: 1092-1098.
Sato, T., et al. Production of menaquinone (vitamin K2)-7 by Bacillus subtilis, J. of Bioscience and Engineering, 91(1):16-20, (2001).
Sauer, Functional expression of the ere-lox site-specific recombination system in the yeast *Saccharomvces cerevisiae* (1987) Mol. Cell. Biol. 7: 2087-2096.
Schaerli, Y., et al., ContinuoFlow polymerase Chain reaction of single-copy DNA Micorfluidic Microdroplets, Anal. Chem., 81: 302-306, (2009).
Scior, Annike et al., Directed PCR-free engineering of highly repetitive DNA sequences, BMC Biotechnology, Biomed Central Ltd., London, GB, vol. 11(1):87, Sep. 23, 2011.

Semizarov, D., et al. Stereoisomers of Deoxynucleoside 5'-Triphosphates as Substrates for Template-dependent and-independent DNA Polymerases, J. of Biol. Chem., 272(14):9556-9560, (Apr. 4, 1997).
Seo, T., et al., Four-color DNA sequencing by synthesis on a chip using photocleavable fluorescent nucleotides, PNAS, 102(17):5926-5933, (Apr. 26, 2005).
Sgaramella, V., et al. Studies of polynucleotides, C.: A novel joining reaction catalyzed by T4-polynucleotide ligase, PNAS, 67(3):1468-1475, (Nov. 1970).
Shabarova, Z., et al., Chemical ligation of DNA: the first non-enzymatic assembly of a biologically active gene, Nucl. Acids Res., 19(15):4247-4251, (1991).
Shao, Z., et al. Random-Priming in Vitro Recombination: An Effective Tool for Directed Evolution, Nucleic Acids Research, 26(2):681-683, (1998).
Shendure et al., Accurate Multiplex Polony Sequencing of an Evolved Bacterial Genome, Science. 309:1728-1732 (2005).
Shpaer, GeneAssist. Smith-Waterman and other database similarity searches and identification of motifs: Methods Mol. Biol. 70: 173-187, 1997.
Sieber, V., et al. Libraries of Hybrid Proteins From Distantly Related Sequences, Nature Biotechnology, 19:456-460, (May 2001).
Simon, D., et al. N-methyl-D-aspartate receptor antagonists disrupt the formation of a mammalian neural map Proc. Natl. Acad. Sci. USA, 89:10593-10597, (Nov. 1992).
Smith et al., A detailed study of the substrate specificity of a chimeric restriction enzyme. Nucleic Acids Research 27(2):674-681 (1999).
Smith et al., Mutation Detection with MutH, MutL, and MutS Mismatch Repair Proteins, Proc. Natl. Acad. Sci. USA, 93:4374-4379, (Apr. 1996).
Smith et al., Single-step purification of polypeptides expressed in *Escherichia coli* as fusions with glutathione Sransferase, Gene, vol. 67, Issue 1, pp. 31-40, (1988).
Smith, H.O., et al. Generating a synthetic genome by whole genome assembly:<DX174 bacteriophage from synthetic oligonucleotides, PNAS, 100(26):15440-15445 (2003).
Soderlind et al., Domain libraries: Synthetic diversity for de novo design of antibody V-regions, Gene, 160:269-272, (1995).
Sprinzl et al., Compilation of tRNA sequences and sequences of tRNA genes, Nucleic Acids Research, 33:D139-D140 (2005).
Stamm et al., Sanchored PCR: PCR with CDNA Coupled to a solid phase, Nucleic Acids Research, 19(6):1350, (Mar. 25, 1991).
Stekel, Microarrays: Making Them and Using Them, Microarray Bioinformatics. Cambridge University Press. pp. 211-230 (2003).
Stemmer et al., Single-step assembly of a gene and entire plasmid from large numbers of oligodeoxyribonucleotides Gene, 164 (1): 49-53, (1995).
Stemmer, DNA shuffling by random fragmentation and reassembly: in vitro recombination for molecular evolution, Proc. Natl. Acad. Sci. USA, 91:10747-10751, (1994).
Sternberg et al. Site-specific Recombination and Its Role in the Life Cycle of Bacteriophage Pl Cold Spring Harbor Symp. Quant. Biol. 45: 297-309, 1981.
Steuer et al., Chimeras of the Homing Endonuclease Pi-SeeI and the Homologous Candida Tropicalis Intein: A Study to Explore the Possibility of Exchanging DNA-Binding Modules to Obtain Highly Specific Endonucleases With Altered Specificity,ChemBioChem., 5(2):206-213, (2004).
Strizhov N. et al. A synthetic crylC gene, encoding a Bacillus thuringiensis delta-endotoxin, confers Spodoptera resistance in Alfalfa and Tobacco PNAS, 93(26):15012-15017.
Tan, S., et al. Zinc-finger protein-targeted gene regulation: Genomewide single-gene specificity, PNAS, 100(21):11997-12002, (Oct. 14, 2003).
Tang K. et al. Chip-based genotyping by mass spectrometry. PNAS, 96: 10016-10020 (1999).
Teh et al., Droplet microfluidics, Lab on Chip. 2008;8(2):198-220.
Third Party Observation under Article 115 EPC for EP publication No. 2864531, filed May 18, 2018.
Tian, J., et al. Accurate multiplex gene synthesis from programmable DNA microchips, Nature, 432:1050-1054, (Dec. 2004).

(56) References Cited

OTHER PUBLICATIONS

Tsai et al., Dimeric CRISPR RNA-guided FokI nucleases for highly specific genome editing. Nat Biotechnol. Jun. 2014;32(6):569-76. doi: 10.1038/nbt.2908. Epub Apr. 25, 2014. Online Methods.
Tsutakawa et al., The Structural Basis of Damaged DNA Recognition and Endonucleolytic Cleavage for Very Short Patch Repair Endonuclease, Nucleic Acids Research, 29(18):3775-3783, (2001).
Tucker et al., Massively parallel sequencing: the next big thing in genetic medicine. Am J Hum Genet. Aug. 2009;85(2):142-54. doi:10.1016/j.ajhg.2009.06.022.
Urata, H., et al. Synthesis and properties of mirror-image DNA, Nucleic Acids Research, 20(13):3325-3332 (1992).
Venkatesan et al., Improved Utility of Photolabile Solid Phase Synthesis Supports for the Synthesis of Oligonucleotides Containing 3'-Hydroxyl Termini, J. of Org. Chem., 61:525-529, (Jan. 26, 1996).
Verma et al., Modified Oligonucleotides: Synthesis and Strategy for Users, Annu. Rev. Biochem., 67:99-134, (1998).
Vogelstein et al., Digital PCR, Pro. Natl. Acad. Sci. 96(16):9236-9241 (1999).
Von Neumann, J. The general and logical theory of automata, Pergamon Press, 5:288-326, (1948).
Wang et al., De novo assembly and characterization of root transcriptome using Illumina paired-end sequencing and development of cSSR markers in sweetpotato (*Lpomoea batatas*), BMC Genomics, 2010, vol. 11, pp. 1-14.
Wang et al., Targeted gene addition to a predetermined site in the human genome using a ZFN-based nicking enzyme. Genome Res. Jul. 2012;22(7):1316-26. doi: 10.1101/gr.122879.111. Epub Mar. 20, 2012.
Waters, V. Conjugation between bacterial and mammalian cells, Nature Genetics, 29:375-376, (Dec. 2001).
Weber et al.. A Modular Cloning System for Standardized Assembly of Multigene Constructs, PLoS ONE, Feb. 18, 2011, vol. 6, No. 2, pp. e16765.
Weiler et al., Combining the Preparation of Oligonucleotide Arrays and Synthesis of High-Quality Primers, Analytical Biochemistry, 243:218-227, (1996).
Weiner et al., Kits and their unique role in molecular biology: a brief retrospective. Biotechniques. Apr. 2008;44(5):701-4. doi: 10.2144/000112796.
Weisberg, et al., Site-specific recombination in Phage Lambda, In: Lambda II, Hendrix, et al. Eds., Cold Spring Harbor Press, Cold Spring Harbor, NY (1983) pp. 211-250.
Werner et al., Fast track assembly of multigene constructs using Golden Gate cloning and the MoClo system, Bioengineered Bugs, Jan. 1, 2012;3(1):38-43.
Wheeler, D., et al. Database resources of the National Center for Biotechnology Information, Nucleic Acids Res., 29(1):11-16, (2001).
White et al. (Digital PCR provides sensitive and absolute calibration for high throughput sequencing, BMC Genomics, 2009, 10:116, Published: Mar. 19, 2009).
Wiedmann et al., Ligase chain reaction (LCR)—overview and applications. PCR Methods Appl. Feb. 1994;3(4):S51-64.
Wilgenbus et al., DNA chip technology ante portas, J. Mol. Med, 77:761-768, (1999).
Williams et al., Modifying the stereochemistry of an enzyme-catalyzed reaction by directed evolution. Proc Natl Acad Sci U S A. Mar. 18, 2003;100(6):3143-8. Epub Mar. 7, 2003.
Xie et al., An Expanding Genetic Code, Methods A Companion to Methods in Enzymology, 36:227-238, (2005).
Xiong et al. PCR based accurate synthesis of long DNA sequences Nature protocols 1 (2): 791 (2006).
Xiong et al., Non-Polymerase-Cycling-Assembly-Based Chemical Gene Synthesis: Strategies, Methods, and Progress; Biotechnology Advances; Elsevier Publishing; Barking, GB; vol. 26; No. 2; pp. 121-134; Nov. 7, 2007.
Xiong, A., et al. A simple, rapid, high-fidelity and cost-effective PCR-based two-step DNA synthesis method for long gene sequences, Nucleic Acids Research, 32(12):e98 (10 pages), (2004).

Xu et al., A novel 5'-iodonucleoside allows efficient nonenzymatic ligation of single-stranded and duplex DNAs, Tetrahedron Letters, 38(32):5595-5598, (1997).
Xu et al., High sequence fidelity in a non-enzymatic DNA autoligation reaction, Nucleic Acids Research, 27(3):875-881, (1999).
Xu, Y., et al. Nonenzymatic autoligation in direct three-color detection of RNA and DNA point mutations, Nature Biotechnology, 19:148-152, (Feb. 2001).
Xuei et al. Use of SAM(2)(R) biotin capture membrane in microarrayed compound screening (mu ARCS) format for nucleic acid polymerization assays Journal of Biomolecular Screening 8:273-282 (2003).
Yan et al., Polymer membranes with two-dimensionally arranged pores derived from monolayers of silica particles, Chem. Mater. 16(9): 1622-1626 (2004).
Yehezkel et al. (De novo DNA synthesis using single molecule PCR, Nucleic Acids Research, 2008, vol. 36, No. 17, e107, Published online Jul. 30, 2008).
Yolov et al. RNA—synthesis by use of T7-RNA-Polymerase and immobilized DNA in a flowing-type reactor. Bioorganicheskaya Khimiya, 17:789-794 (1991 ).
Yoon et al., Efficient cloning and engineering of entire mitochondrial genomes in *Escherichia coli* and transfer into transcriptionally active mitochondria, Nucleic Acids Research, 31(5):1407-1415,(2003).
Yoon, Y., et al. Cre/loxP-mediated in vivo excision of large segments from yeast genome and their amplification based on the 2 um plasmid-derived system, Gene, 223:67-76, (1998).
Yosef et al., Restoration of gene function by homologous recombination: from PCR to gene expression in one step. Appl. Environ. Microbiol. Dec. 2004;70(12):7156-60.
Young et al., Two-step Total Gene Synthesis Method Nucleic Acids Research, 32(7):e59 (6 pages), (2004).
Zha, D., et al. Assembly of Designed Oligonucleotides as an Efficient Method for Gene Recombination: A New Tool in Directed Evolution, ChemBioChem, 4:34-39, (2003).
Zhang, C., et al., PCR microfluidic devices for DNA amplification, Biotechnology Advances, 24(3):243-284, 2006.
Zhang, P. et al. Rational Design of a Chimeric Endonuclease Targeted to NotI Recognition Site Protein Engineering Design & Selection, 20(10):497-504, (Oct. 2007).
Zhang, Z., et al. Selective Incorporation of 5-Hydroxytryptophan Into Proteins in Mammalian Cells, Proceedings of the National Academy of Sciences of the United States of America, 101(24):8882-8887, (Jun. 15, 2004).
Zhao, H., et al. Molecular Evolution by Staggered Extension Process (StEP) in Vitro Recombination, Nature Biotechnology, 16:258-261, (Mar. 1998).
Zhou et al. Microfluidic PicoArray synthesis of oligodeoxynucleotides and simultaneous assembling of multiple DNA sequences Nucleic Acids Research , 32(18): 5409-5417 (2004).
Zhu et al., (1995). Cleavage-dependent Ligation by the FLP Recombinase. J Biol. Chem. 270: 23044-23054.
International Preliminary Report on Patentability for PCT/US2013/037921 (Methods for Sorting Nucleic Acids and Multiplexed Preparative In Vitro Cloning, filed Apr. 24, 2013), issued by ISA/WIPO, 12 pages (dated Oct. 28, 2014).
International Search Report in PCT/US2013/037921 dated Dec. 31, 2013.
Invitation to Pay Additional Fees and, Where Applicable, Protest Fee for PCT/US2013/037921 (Methods for Sorting Nucleic Acids and Multiplexed Preparative In Vitro Cloning, filed Apr. 24, 2013), issued by ISA/WIPO, 2 pages (Sep. 5, 2013).
Written Opinion for PCT/US2013/037921 (Methods for Sorting Nucleic Acids and Multiplexed Preparative In Vitro Cloning, filed Apr. 24, 2013), issued by ISA/US, 11 pages (dated Dec. 31, 2013).
Extended European Search Report dated Aug. 27, 2019 for Application No. 19153395.9.
Hayden et al., Gene synthesis by serial cloning of oligonucleotides. DNA. Oct. 1988;7(8):571-7.

C

Junctions: GTGT, CTTA, TATG, [ACAC]
Junctions: GTGT, CTTA, TATG, [ACAC]

GTGT
CTTA = 3 dist

Parse A: Total 22 (2.2 junction distance average), CTTA vs.
CATA = 1 junction distance (failed parse)

Parse B: Total 26 (2.6 junction distance average) =>
better scoring parse

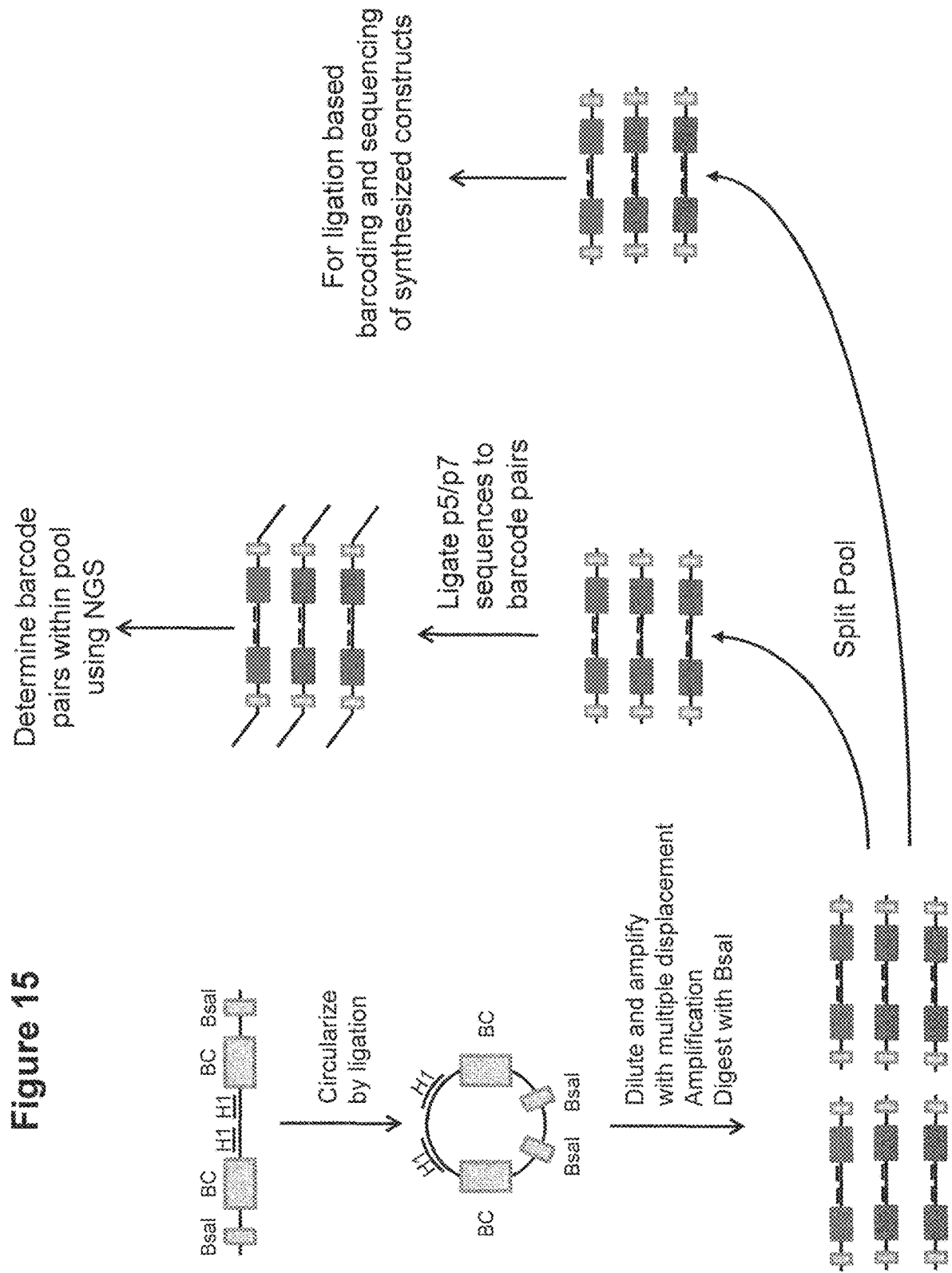

SEQUENCE LISTING

<160> NUMBER OF SEQ ID NOS: 38

<210> SEQ ID NO 1
<211> LENGTH: 14
<212> TYPE: DNA
<213> ORGANISM: Artificial Sequence
<220> FEATURE:
<223> OTHER INFORMATION: Synthetic Polynucleotide

<400> SEQUENCE: 1
actcacctcg tttc                                                       14

<210> SEQ ID NO 2
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 2
ccttataagc atgtctcata                                                 20

<210> SEQ ID NO 3
<211> LENGTH: 22
<212> TYPE: DNA
<213> ORGANISM: Artificial Sequence
<220> FEATURE:
<223> OTHER INFORMATION: Synthetic Polynucleotide

<400> SEQUENCE: 3
agagacagac tcacctcgtt tc                                              22

<210> SEQ ID NO 4
<211> LENGTH: 27
<212> TYPE: DNA
<213> ORGANISM: Artificial Sequence
<220> FEATURE:
<223> OTHER INFORMATION: Synthetic Polynucleotide

<400> SEQUENCE: 4
gagacagtat gagacatgct tataagg                                         27

<210> SEQ ID NO 5
<211> LENGTH: 14
<212> TYPE: DNA
<213> ORGANISM: Artificial Sequence
<220> FEATURE:
<223> OTHER INFORMATION: Synthetic Polynucleotide

<400> SEQUENCE: 5
gccgccgctg gggc                                                       14

<210> SEQ ID NO 6
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 6
cctccccacg ctctctagcc                                                 20

<210> SEQ ID NO 7
<211> LENGTH: 15
<212> TYPE: DNA
<213> ORGANISM: Artificial Sequence

```
<220> FEATURE:
<223> OTHER INFORMATION: Synthetic Polynucleotide

<400> SEQUENCE: 7
ggccgccgct ggggc                                              15

<210> SEQ ID NO 8
<211> LENGTH: 24
<212> TYPE: DNA
<213> ORGANISM: Artificial Sequence
<220> FEATURE:
<223> OTHER INFORMATION: Synthetic Polynucleotide

<400> SEQUENCE: 8
acagggctag agagcgtggg gagg                                    24

<210> SEQ ID NO 9
<211> LENGTH: 14
<212> TYPE: DNA
<213> ORGANISM: Artificial Sequence
<220> FEATURE:
<223> OTHER INFORMATION: Synthetic Polynucleotide

<400> SEQUENCE: 9
ggagcgatca ccat                                               14

<210> SEQ ID NO 10
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 10
tagacgttca tggtacatac                                         20

<210> SEQ ID NO 11
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 11
acagggagcg atcaccat                                           18

<210> SEQ ID NO 12
<211> LENGTH: 24
<212> TYPE: DNA
<213> ORGANISM: Artificial Sequence
<220> FEATURE:
<223> OTHER INFORMATION: Synthetic Polynucleotide

<400> SEQUENCE: 12
acaggtatgt accatgaacg tcta                                    24

<210> SEQ ID NO 13
<211> LENGTH: 14
<212> TYPE: DNA
<213> ORGANISM: Artificial Sequence
<220> FEATURE:
<223> OTHER INFORMATION: Synthetic Polynucleotide

<400> SEQUENCE: 13
cggagtgctg ggat                                               14
```

```
<210> SEQ ID NO 14
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 14
cctttgtggt catgagtttg                                                   20

<210> SEQ ID NO 15
<211> LENGTH: 16
<212> TYPE: DNA
<213> ORGANISM: Artificial Sequence
<220> FEATURE:
<223> OTHER INFORMATION: Synthetic Polynucleotide

<400> SEQUENCE: 15
agcggagtgc tgggat                                                       16

<210> SEQ ID NO 16
<211> LENGTH: 22
<212> TYPE: DNA
<213> ORGANISM: Artificial Sequence
<220> FEATURE:
<223> OTHER INFORMATION: Synthetic Polynucleotide

<400> SEQUENCE: 16
agcaaactca tgaccacaaa gg                                                22

<210> SEQ ID NO 17
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 17
catcaacgtt catgtcgcgc                                                   20

<210> SEQ ID NO 18
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 18
ccttgggtgc tcgcagtaaa                                                   20

<210> SEQ ID NO 19
<211> LENGTH: 14
<212> TYPE: DNA
<213> ORGANISM: Artificial Sequence
<220> FEATURE:
<223> OTHER INFORMATION: Synthetic Polynucleotide

<400> SEQUENCE: 19
tcgtcggcag cgtc                                                         14

<210> SEQ ID NO 20
<211> LENGTH: 19
<212> TYPE: DNA
<213> ORGANISM: Artificial Sequence
<220> FEATURE:
<223> OTHER INFORMATION: Synthetic Polynucleotide
```

```
<400> SEQUENCE: 20
agatgtgtat aagagacag                                         19

<210> SEQ ID NO 21
<211> LENGTH: 15
<212> TYPE: DNA
<213> ORGANISM: Artificial Sequence
<220> FEATURE:
<223> OTHER INFORMATION: Synthetic Polynucleotide

<400> SEQUENCE: 21
gtctcgtggg ctcgg                                             15

<210> SEQ ID NO 22
<211> LENGTH: 19
<212> TYPE: DNA
<213> ORGANISM: Artificial Sequence
<220> FEATURE:
<223> OTHER INFORMATION: Synthetic Polynucleotide

<400> SEQUENCE: 22
agatgtgtat aagagacag                                         19

<210> SEQ ID NO 23
<211> LENGTH: 14
<212> TYPE: DNA
<213> ORGANISM: Artificial Sequence
<220> FEATURE:
<223> OTHER INFORMATION: Synthetic Polynucleotide

<400> SEQUENCE: 23
ctaaatggat tcga                                              14

<210> SEQ ID NO 24
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 24
tgatgaaaga aataaaatgt                                        20

<210> SEQ ID NO 25
<211> LENGTH: 28
<212> TYPE: DNA
<213> ORGANISM: Artificial Sequence
<220> FEATURE:
<223> OTHER INFORMATION: Synthetic Polynucleotide

<400> SEQUENCE: 25
tgtataagag acagctaaat ggattcga                               28

<210> SEQ ID NO 26
<211> LENGTH: 32
<212> TYPE: DNA
<213> ORGANISM: Artificial Sequence
<220> FEATURE:
<223> OTHER INFORMATION: Synthetic Polynucleotide

<400> SEQUENCE: 26
tataagagac agcattttta tttctttcat ca                          32

<210> SEQ ID NO 27
```

```
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 27
gatggagatg ggcaacgcaa                                                20

<210> SEQ ID NO 28
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 28
gatggagatg tgcaacgcaa                                                20

<210> SEQ ID NO 29
<211> LENGTH: 14
<212> TYPE: DNA
<213> ORGANISM: Artificial Sequence
<220> FEATURE:
<223> OTHER INFORMATION: Synthetic Polynucleotide

<400> SEQUENCE: 29
gagacctcgg ctgg                                                      14

<210> SEQ ID NO 30
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 30
gttctacccc gaataaatgc                                                20

<210> SEQ ID NO 31
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 31
caggcattta ttcggggtag aac                                            23

<210> SEQ ID NO 32
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 32
taacaataca gcagggtgtt                                                20

<210> SEQ ID NO 33
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 33
```

```
ttacttcttc caatcaacta                                              20

<210> SEQ ID NO 34
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 34
ttacttcttc aaatcaacta                                              20

<210> SEQ ID NO 35
<211> LENGTH: 14
<212> TYPE: DNA
<213> ORGANISM: Artificial Sequence
<220> FEATURE:
<223> OTHER INFORMATION: Synthetic Polynucleotide

<400> SEQUENCE: 35
gagacctcgg ctgg                                                    14

<210> SEQ ID NO 36
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 36
gttctacccc gaataaatgc                                              20

<210> SEQ ID NO 37
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 37
acaggagacc tcggctgg                                                18

<210> SEQ ID NO 38
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 38
ttacttcttc caatcaacta                                              20
```

METHODS FOR SORTING NUCLEIC ACIDS AND MULTIPLEXED PREPARATIVE IN VITRO CLONING

RELATED APPLICATIONS

This application is a continuation of U.S. patent application Ser. No. 13/986,366, filed Apr. 24, 2013, entitled "Methods for Sorting Nucleic Acids and Multiplexed Preparative In Vitro Cloning," which claims the benefit under 35 U.S.C. § 119(e) of and priority to U.S. provisional application Ser. No. 61/851,774, filed Mar. 13, 2013, U.S. provisional application Ser. No. 61/848,961, filed Jan. 16, 2013, U.S. provisional application Ser. No. 61/637,750, filed Apr. 24, 2012, and U.S. provisional application Ser. No. 61/638,187, filed Apr. 25, 2012, the entire disclosure of each of which is incorporated herein by reference in its entirety.

REFERENCE TO SEQUENCE LISTING

This specification includes a sequence listing provided on a compact disc, submitted herewith, which includes the file entitled 127662-013702US_ST25.txt having the following size: 11,000 bytes which was created Apr. 24, 2013, the contents of which are incorporated by reference herein.

FIELD OF THE INVENTION

Methods and compositions of the invention relate to nucleic acid assembly, and particularly to methods for sorting and cloning nucleic acids having a predetermined sequence.

BACKGROUND

Recombinant and synthetic nucleic acids have many applications in research, industry, agriculture, and medicine. Recombinant and synthetic nucleic acids can be used to express and obtain large amounts of polypeptides, including enzymes, antibodies, growth factors, receptors, and other polypeptides that may be used for a variety of medical, industrial, or agricultural purposes. Recombinant and synthetic nucleic acids also can be used to produce genetically modified organisms including modified bacteria, yeast, mammals, plants, and other organisms. Genetically modified organisms may be used in research (e.g., as animal models of disease, as tools for understanding biological processes, etc.), in industry (e.g., as host organisms for protein expression, as bioreactors for generating industrial products, as tools for environmental remediation, for isolating or modifying natural compounds with industrial applications, etc.), in agriculture (e.g., modified crops with increased yield or increased resistance to disease or environmental stress, etc.), and for other applications. Recombinant and synthetic nucleic acids also may be used as therapeutic compositions (e.g., for modifying gene expression, for gene therapy, etc.) or as diagnostic tools (e.g., as probes for disease conditions, etc.).

Numerous techniques have been developed for modifying existing nucleic acids (e.g., naturally occurring nucleic acids) to generate recombinant nucleic acids. For example, combinations of nucleic acid amplification, mutagenesis, nuclease digestion, ligation, cloning and other techniques may be used to produce many different recombinant nucleic acids. Chemically synthesized polynucleotides are often used as primers or adaptors for nucleic acid amplification, mutagenesis, and cloning.

Techniques also are being developed for de novo nucleic acid assembly whereby nucleic acids are made (e.g., chemically synthesized) and assembled to produce longer target nucleic acids of interest. For example, different multiplex assembly techniques are being developed for assembling oligonucleotides into larger synthetic nucleic acids that can be used in research, industry, agriculture, and/or medicine. However, one limitation of currently available assembly techniques is the relatively high error rate. As such, high fidelity, low cost assembly methods are needed.

SUMMARY OF THE INVENTION

Aspects of the invention relate to methods of sorting and cloning nucleic acid molecules having a desired or predetermined sequence. In some embodiments, the method comprises providing one or more pools of nucleic acid molecules comprising at least two populations of target nucleic acid molecules, each population of nucleic acid molecules having a unique target nucleic acid sequence, tagging the 5' end and the 3' end of the nucleic acid molecules with a non-target oligonucleotide tag sequence, wherein the oligonucleotide tag sequences comprise a unique nucleotide tag and a primer region, diluting the tagged nucleic acid molecules, subjecting the tagged nucleic acid molecules to sequencing reactions from both ends to obtain paired end reads, and sorting the nucleic acid molecules having the desired sequence according to the identity of their corresponding unique pair of oligonucleotide tags. Yet in other embodiments, the method comprises providing one or more pools of nucleic acid molecules comprising at least two populations of nucleic acid molecules, with each population of nucleic acid molecules having a unique internal nucleic acid sequence, and a oligonucleotide tag sequence at its 5' end and 3' end, wherein the oligonucleotide tag sequences comprise a unique nucleotide tag and a primer region, subjecting the tagged nucleic acid molecules to sequencing reactions from both ends to obtain paired end reads, and sorting the nucleic acid molecules having the desired sequence according to the identity of their corresponding unique pair of oligonucleotide tags. In some embodiments, each population of nucleic acid molecules has a different desired nucleic acid sequence.

In some embodiments, the unique nucleotide tag can be ligated at the 5' end and the 3' end of the nucleic acid molecule. Yet in other embodiments, the unique oligonucleotide tag can be joined at each end of the nucleic acid molecules by PCR. In some embodiments, the unique nucleotide tag can include a completely degenerate sequence, a partially degenerate sequence or a non-degenerate sequence. In some embodiments, the unique oligonucleotide tag can include a coded barcode. For example, the unique nucleotide tag can include the following sequences CCWSWDHSHDBVHDNNNNMM or CCSWSWHDSDHVBDHNNNNMM.

In some embodiments, the method further comprises amplifying the nucleic acid molecules having the desired sequence. In some embodiments, the method comprises amplifying the constructs having the desired sequence using primers complementary to the primer region and the tag nucleotide sequence. In some embodiments, the method comprises amplifying the constructs having the desired sequence using primers complementary to the oligonucleotide tag sequence. Yet in other embodiments, primers that are complementary to the target nucleic acid sequence can be used to amplify the constructs having the desired sequence.

In some embodiments, the method further comprises pooling a plurality of nucleic acid molecules to form the pool of nucleic acid molecules, wherein each plurality of nucleic acid molecules comprises a population of nucleic acid sequences having the desired sequence (i.e. error-free nucleic acid sequences) and a population of nucleic acid a sequences different than the desired sequence (error-containing nucleic acid sequences). In some embodiments, the nucleic acid molecules can be assembled de novo. In some embodiments, the plurality of nucleic acid molecules can be diluted prior to the step of pooling or after the step of pooling to form a normalized pool of nucleic acid molecules.

In some embodiments, the oligonucleotide tags can be joined to the nucleic acid molecules prior to diluting the nucleic acid molecules from a pool. In some embodiments, the method can further comprise amplifying the tagged nucleic acid molecules after the dilution step. Yet in other embodiments, the oligonucleotide tags can be joined to the nucleic acid molecules after diluting the nucleic acid molecules from a pool.

In some embodiments, each nucleic acid molecule comprises a 5' end common adaptor sequence and 3' end common adaptor sequence and the oligonucleotide tag sequence further comprises a common adaptor sequence. In some embodiments, each nucleic acid molecule is designed to have a 5' end common adaptor sequence and 3' end common adaptor sequence. Yet in other embodiments, the 5' end common adaptor sequence and 3' end common adaptor sequences are added to each nucleic acid molecules by ligation.

Some aspects of the invention relate to methods for designing a plurality of oligonucleotides for assembly into a nucleic acid sequence of interest having a predefined sequence. In some embodiments, the method comprises computationally dividing the sequence of each nucleic acid sequence of interest into partially overlapping construction oligonucleotide sequences; selecting a first plurality of construction oligonucleotide sequences such that every two adjacent construction oligonucleotide sequences overlap with each other by N bases, wherein each N-base sequence is at least 4 bases long; comparing the N-base sequences to one another so that one or more of the following constraints are met: the N-base sequences differ to one another by at least 2 bases, or the N-base sequences differ to one another by at least one base in the last 3 bases of the 5' end or 3' end; identifying from the first plurality of construction oligonucleotide sequences, a second plurality of construction oligonucleotide sequences satisfying the constraints; determining the number of oligonucleotides in the second plurality of oligonucleotides; ranking the oligonucleotides from the second plurality of oligonucleotides that meet or exceed the constraints and based on the number of oligonucleotides; and using the ranking to design a set of satisfactory partially overlapping construction oligonucleotides. In the step of ranking, the set having the smaller number of oligonucleotides can be selected, and/or the set having the higher number of base differences in the N-base sequence can be selected. In some embodiments, non-target flanking sequences can be computationally adding to the termini of at least a portion of said construction oligonucleotides. The non-target flanking sequences can comprise a primer binding site. The method can further comprise synthesizing the set of satisfactory partially overlapping construction oligonucleotides, for example on a solid support and assembling the construction oligonucleotides into the nucleic acid of interest.

In some aspects, the invention relate to a method of isolating a nucleic acid having a predefined sequence, the method comprising: providing at least one population of nucleic acid molecules; isolating a clonal population of nucleic acid molecules on a surface, determining the sequence of the clonal population of nucleic acid molecules, localizing the clonal population having the predefined sequence, and amplifying the nucleic acid molecule having the predefined sequence. In some embodiments, the step of isolating can be by dilution and the surface can be a flow cell.

In other aspects of the invention, the method for isolating a nucleic acid having a predefined sequence comprises providing a pool of nucleic acid molecules comprising error-free and error-containing nucleic acid molecules, tagging the nucleic acid molecules, optionally fragmenting the nucleic acid molecules, determining the sequence of the nucleic acid molecules, localizing the error-free and error-containing nucleic acid molecules, and isolating the error-free nucleic acid molecules. In some embodiments, the step of isolating comprises one or more of the following: ablating the error-containing nucleic acid molecules, selectively amplifying the error-free nucleic acid molecules, and/or immobilizing the error-free nucleic acid molecules onto a surface and separating the error-free nucleic acid molecules from the error-containing nucleic acid molecules. In some embodiments, the pool of nucleic acid molecules comprises at least two populations of nucleic acids and each population of nucleic acid can be immobilized onto a distinct population of beads. In some embodiments, the method further comprises sorting the distinct populations of beads.

In some aspects of the invention, methods for sorting molecules having a predetermined sequence are provided. In some embodiments, the method comprises (a) providing a pool of nucleic acid molecules comprising at least two population of nucleic acid molecules, each population of nucleic acid molecule having a unique target nucleic acid sequence, the target nucleic acid sequence having a 5' end and a 3' end, (b) tagging the 5' end and the 3' end of the target nucleic acid molecules with a pair of non-target oligonucleotide tag sequences, wherein the oligonucleotide tag sequence comprises a unique nucleotide tag, (c) diluting the tagged target nucleic acids, (d) amplifying the tagged nucleic acids, (e) dividing the amplified tagged nucleic acids into two pools, (f) subjecting a first pool comprising the tagged target nucleic acid molecules to a sequencing reaction from both ends to obtain a paired end read; (g) subjecting a second pool comprising the tagged target nucleic acid molecules to ligation to form circular nucleic acid molecules thereby bringing the pair of tags in close proximity, (h) sequencing the pair of tags, (i) sorting the target nucleic acid molecules having the predetermined sequence according to the identity of their corresponding unique pair of oligonucleotide tags. In some embodiments, the pair of tags can be amplified before being sequenced. In some embodiments, the pair of tags can be cleaved off before being sequenced, for example using a restriction enzyme.

BRIEF DESCRIPTION OF THE FIGURES

The patent or application file contains at least one drawing executed in color. Copies of this patent or patent application publication with color drawing(s) will be provided by the Office upon request and payment of the necessary fee.

FIG. 14A illustrates a pathway according to one embodiment by which the barcoded ends of the molecules are brought together by blunt end ligation of the constructs into circles. FIG. 14B illustrates a pathway according to another embodiment by which the barcoded ends of the molecules are brought together by blunt end ligation of the constructs into circles. FIG. 14C illustrates a method according to a non-limiting embodiment of attaching barcodes to the synthesized constructs.

FIG. 15 illustrates a non-limiting embodiment for determining barcode pair information.

DETAILED DESCRIPTION OF THE INVENTION

Figure 1:
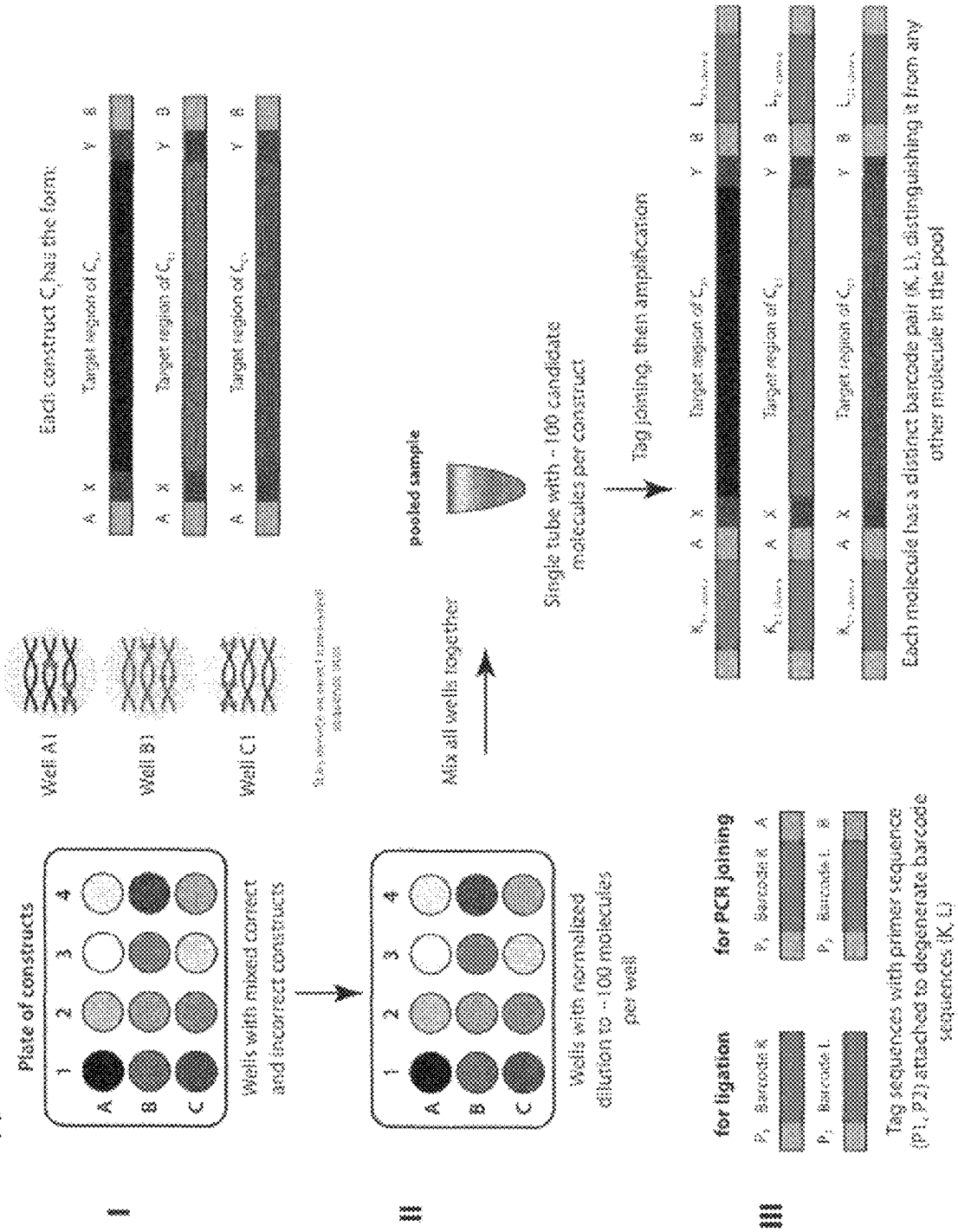
FIG. 1A illustrates steps I, II, and III of a non-limiting exemplary method of preparative cloning according to some embodiments.
FIG. 1B illustrates steps IV and V of a non-limiting exemplary method of preparative cloning according to some embodiments.
FIG. 1C illustrates the preparative recovery of correct clones, step VI, of a non-limiting exemplary method of preparative cloning according to some embodiments. Stars denote incorrect or undesired sequence sites.
Figure 1:
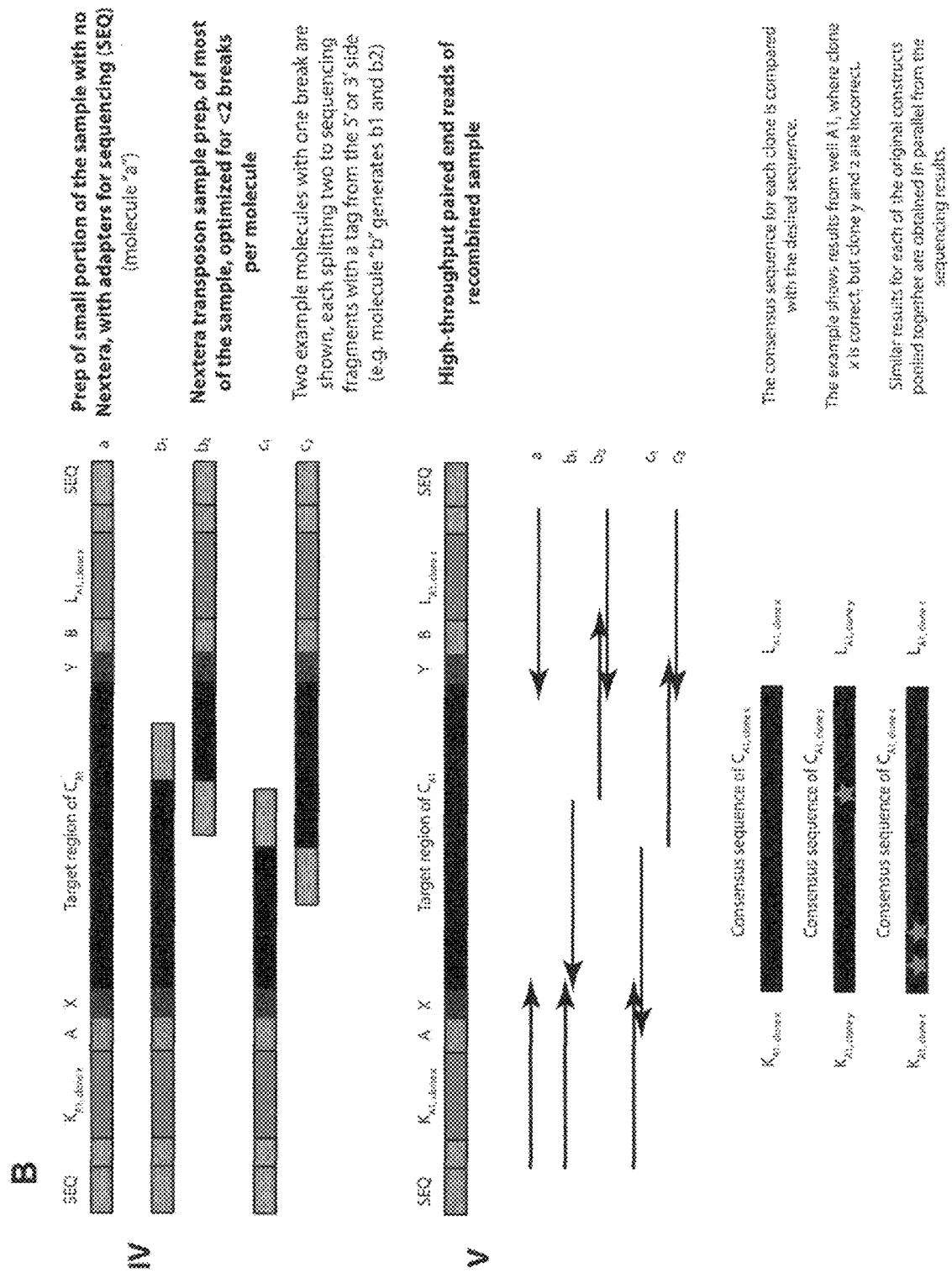
Figure 1:
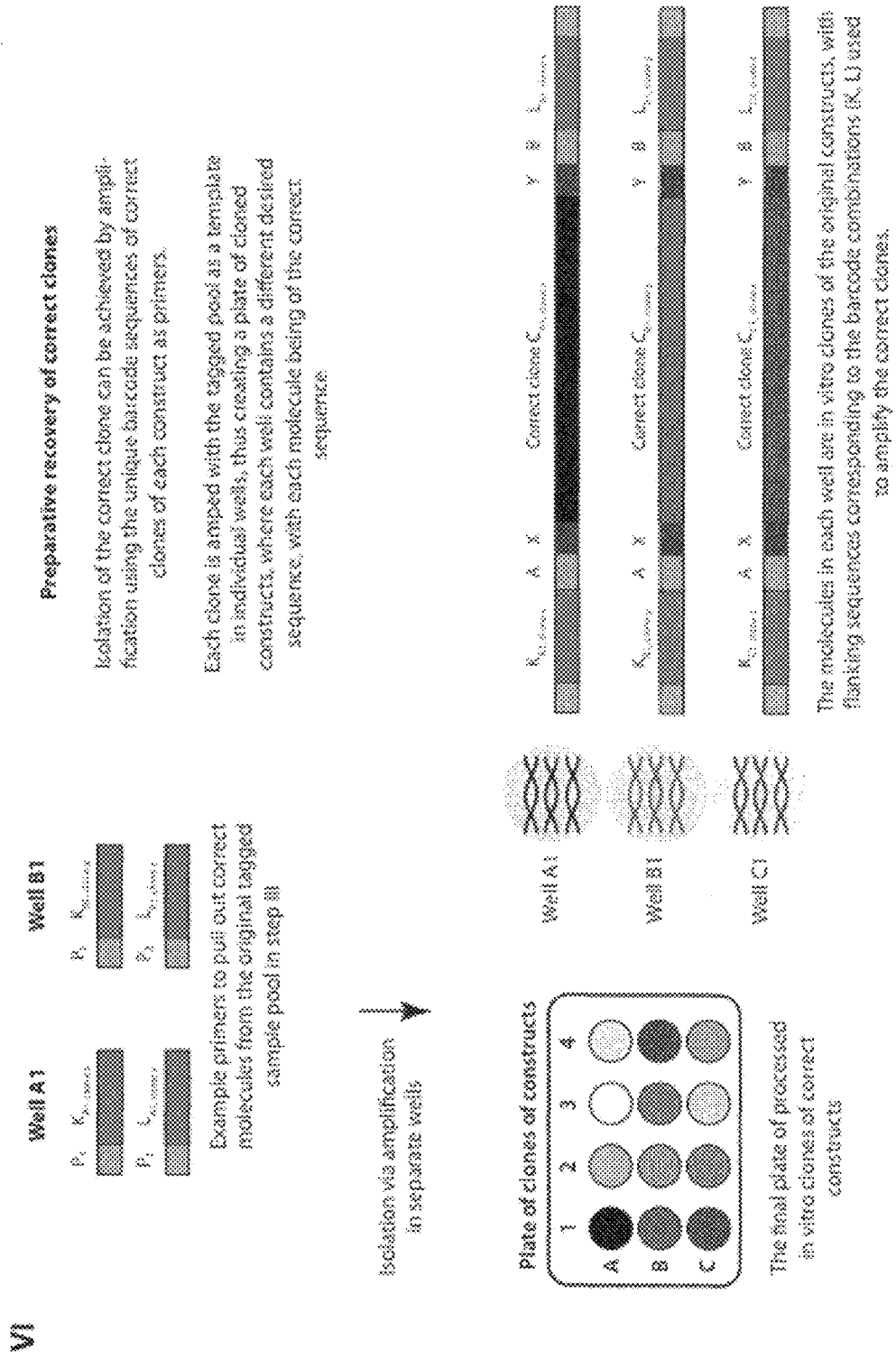

Techniques have been developed for de novo nucleic acid assembly whereby nucleic acids are made (e.g., chemically synthesized) and assembled to produce longer target nucleic acids of interest. For example, different multiplex assembly techniques are being developed for assembling oligonucleotides into larger synthetic nucleic acids. However, one limitation of currently available assembly techniques is the relatively high error rate. There is therefore a need to isolate nucleic acid constructs having a predetermined sequence and discarding constructs having nucleic acid errors.

Aspects of the invention can be used to isolate nucleic acid molecules from large numbers of nucleic acid fragments efficiently, and/or to reduce the number of steps required to generate large nucleic acid products, while reducing error rate. Aspects of the invention can be incorporated into nucleic assembly procedures to increase assembly fidelity, throughput and/or efficiency, decrease cost, and/or reduce assembly time. In some embodiments, aspects of the invention may be automated and/or implemented in a high throughput assembly context to facilitate parallel production of many different target nucleic acid products. In some embodiments, nucleic acid constructs may be assembled using starting nucleic acids obtained from one or more different sources (e.g., synthetic or natural polynucleotides, nucleic acid amplification products, nucleic acid degradation products, oligonucleotides, etc.). Aspects of the invention relate to the use of a high throughput platform for sequencing nucleic acids such as assembled nucleic acid constructs to identify high fidelity nucleic acids at lower cost. Such platform has the advantage to be scalable, to allow multiplexed processing, to allow for the generation of a large number of sequence reads, to have a fast turnaround time and to be cost efficient.

Some aspects the invention relate to the preparation of construction oligonucleotides for high fidelity nucleic acid assembly. Aspects of the invention may be useful to increase the throughput rate of a nucleic acid assembly procedure and/or reduce the number of steps or amounts of reagent used to generate a correctly assembled nucleic acid. In certain embodiments, aspects of the invention may be useful in the context of automated nucleic acid assembly to reduce the time, number of steps, amount of reagents, and other factors required for the assembly of each correct nucleic acid. Accordingly, these and other aspects of the invention may be useful to reduce the cost and time of one or more nucleic acid assembly procedures.

The methods described herein may be used with any nucleic acid molecules, library of nucleic acids or pool of nucleic acids. For example, the methods of the invention can be used to generate nucleic acid constructs, oligonucleotides or libraries of nucleic acids having a predefined sequence. In some embodiments, the nucleic acid library may be obtained from a commercial source or may be designed and/or synthesized onto a solid support (e.g. array).

Parsing

In some embodiments, a nucleic acid sequence of interest can be parsed into a set of construction oligonucleotides that together comprise the nucleic acid sequence of interest. For example, in a first step, sequence information can be obtained. The sequence information may be the sequence of a nucleic acid of interest that is to be assembled. In some embodiments, the sequence may be received in the form of an order from a customer. In some embodiments, the sequence may be received as a nucleic acid sequence (e.g., DNA or RNA). In some embodiments, the sequence may be received as a protein sequence. The sequence may be converted into a DNA sequence. For example, if the sequence obtained is an RNA sequence, the Us may be replaced with Ts to obtain the corresponding DNA sequence. If the sequence obtained is a protein sequence, it may be converted into a DNA sequence using appropriate codons for the amino acids.

In some embodiments, the sequence information may be analyzed to determine an assembly strategy, according to one or more of the following: the number of the junctions, the length of the junctions, the sequence of the junctions, the number of the fragments, the length of the fragments, the sequence of the fragments to be assembled by cohesive end ligation, to generate the predefined nucleic acid sequences of interest. In some embodiments, the fragments can be assembled by cohesive end ligation or by polymerase chain assembly.

In some embodiments, the assembly design is based on the length of the construction oligonucleotides and/or the number of junctions. For example, according to some embodiments, the length of the fragments can have an average length range of 98 to 104 bps or 89 to 104 bps. In some embodiments, the design that results in the smaller number of fragments or junctions can be selected.

In some embodiments, the sequence analysis may involve scanning the junctions and selecting junctions having one or more of the following feature(s): each junction is 4 or more nucleotides long, each junction differs from the other junctions by at least 2 nucleotides, and/or each junction differs from the other junctions by one or more nucleotide in the last 3 nucleotides of the junction sequence. Junction can then be scored according to the junction distance (also referred herein as Levenshtein distance) in the junction sequences. As used herein, the junction distance or Levenshtein distance corresponds to the measure of the difference between two sequences. Accordingly, the junction distance or Levenshtein distance between a first and a second junction sequences corresponds to the number of single nucleotide changes required to change the first sequence into the second sequence. For example, a 1 nucleotide difference in a sequence of 4 nucleotides corresponds to a junction distance of 1, a 2 nucleotides difference in a sequence of 4 nucleotides corresponds to a junction distance of 2. Junction distances can be averaged. In some embodiments, the junctions are designed so as to have an average of 2 or higher junction distance. In some embodiments, the design that results in the greater junction distance can be selected.

In some embodiments, all possible parses which satisfy the predetermined constraints are analyzed. If no valid parses are found, constraints can be relaxed to find a set of possible oligonucleotide sequences and junctions. For example, the constraint on the length of oligonucleotides can be relaxed to include oligonucleotides having shorter or longer lengths.

Figure 6:
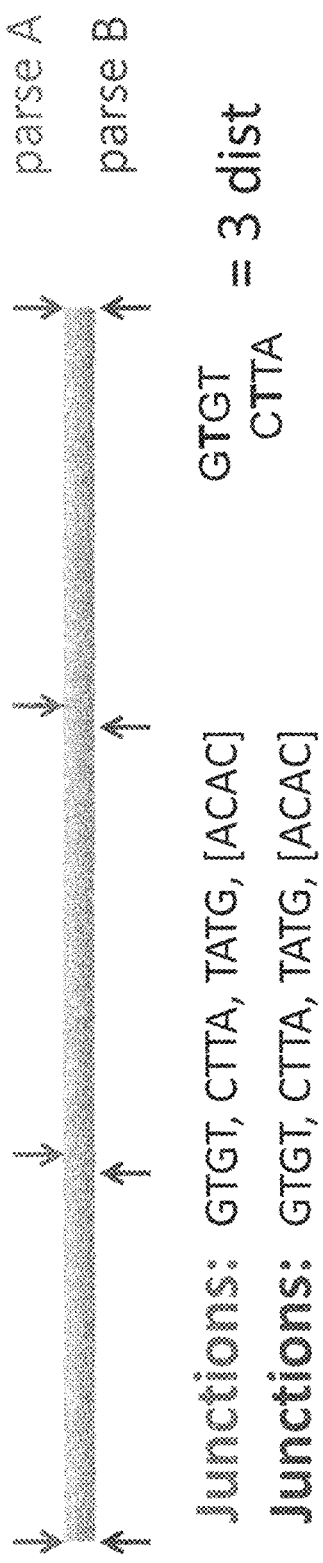
FIG. 6 illustrates a non-limiting exemplary parsing and scoring parses.

In some embodiments, all possible parses which satisfy the predetermined constraints are ranked based on any metric provided herein. For example, each parse can be ranked based on the average junction distance metric (as illustrated in FIG. 6), the GC content, the complexity of the oligonucleotide sequence, and/or any other suitable metric.

In some embodiments, the sequence analysis may involve scanning for the presence of one or more interfering sequence features that are known or predicted to interfere with oligonucleotide synthesis, amplification or assembly. For example, an interfering sequence structure may be a sequence that has a low GC content (e.g., less than 30% GC, less than 20% GC, less than 10% GC, etc.) over a length of at least 10 bases (e.g., 10-20 bases, 20-50 bases, 50-100 bases, or more than 100 bases), or sequence that may be forming secondary structures or stem-loop structures.

In some embodiments, after the construct qualification and parsing steps, synthetic construction oligonucleotides for the assembly may be designed (e.g. sequence, size, and number). Synthetic oligonucleotides can be generated using standard DNA synthesis chemistry (e.g. phosphoramidite method). Synthetic oligonucleotides may be synthesized on a solid support, such as for example a microarray, using any appropriate technique known in the art. Oligonucleotides can be eluted from the microarray prior to be subjected to amplification or can be amplified on the microarray.

As used herein, an oligonucleotide may be a nucleic acid molecule comprising at least two covalently bonded nucleotide residues. In some embodiments, an oligonucleotide may be between 10 and 1,000 nucleotides long. For example, an oligonucleotide may be between 10 and 500 nucleotides long, or between 500 and 1,000 nucleotides long. In some embodiments, an oligonucleotide may be between about 20 and about 300 nucleotides long (e.g., from about 30 to 250, from about 40 to 220 nucleotides long, from about 50 to 200 nucleotides long, from about 60 to 180 nucleotides long, or from about 65 or about 150 nucleotides long), between about 100 and about 200 nucleotides long, between about 200 and about 300 nucleotides long, between about 300 and about 400 nucleotides long, or between about 400 and about 500 nucleotides long. However, shorter or longer oligonucleotides may be used. An oligonucleotide may be a single-stranded or double-stranded nucleic acid. As used herein the terms "nucleic acid", "polynucleotide", "oligonucleotide" are used interchangeably and refer to naturally-occurring or synthetic polymeric forms of nucleotides. The oligonucleotides and nucleic acid molecules of the present invention may be formed from naturally occurring nucleotides, for example forming deoxyribonucleic acid (DNA) or ribonucleic acid (RNA) molecules. Alternatively, the naturally occurring oligonucleotides may include structural modifications to alter their properties, such as in peptide nucleic acids (PNA) or in locked nucleic acids (LNA). The solid phase synthesis of oligonucleotides and nucleic acid molecules with naturally occurring or artificial bases is well known in the art. The terms should be understood to include equivalents, analogs of either RNA or DNA made from nucleotide analogs and as applicable to the embodiment being described, single-stranded or double-stranded polynucleotides. Nucleotides useful in the invention include, for example, naturally-occurring nucleotides (for example, ribonucleotides or deoxyribonucleotides), or natural or synthetic modifications of nucleotides, or artificial bases. As used herein, the term monomer refers to a member of a set of small molecules which are and can be joined together to form an oligomer, a polymer or a compound composed of two or more members. The particular ordering of monomers within a polymer is referred to herein as the "sequence" of the polymer. The set of monomers includes but is not limited to example, the set of common L-amino acids, the set of D-amino acids, the set of synthetic and/or natural amino acids, the set of nucleotides and the set of pentoses and hexoses. Aspects of the invention described herein primarily with regard to the preparation of oligonucleotides, but could readily be applied in the preparation of other polymers such as peptides or polypeptides, polysaccharides, phospholipids, heteropolymers, polyesters, polycarbonates, polyureas, polyamides, polyethyleneimines, polyarylene sulfides, polysiloxanes, polyimides, polyacetates, or any other polymers.

Usually nucleosides are linked by phosphodiester bonds. Whenever a nucleic acid is represented by a sequence of letters, it will be understood that the nucleosides are in the 5' to 3' order from left to right. In accordance to the IUPAC notation, "A" denotes deoxyadenosine, "C" denotes deoxycytidine, "G" denotes deoxyguanosine, "T" denotes deoxythymidine, "U" denotes the ribonucleoside, uridine. In addition, there are also letters which are used when more than one kind of nucleotide could occur at that position: "W" (i.e. weak bonds) represents A or T, "S" (strong bonds) represents G or C, "M" (for amino) represents A or C, "K"

(for keto) represents G or T, "R" (for purine) represents A or G, "Y" (for pyrimidine) represents C or T, "B" represents C, G or T, "D" represents A, G or T, "H" represents A, C or T, "V" represents A, C, or G and "N" represents any base A, C, G or T (U). It is understood that nucleic acid sequences are not limited to the four natural deoxynucleotides but can also comprise ribonucleoside and non-natural nucleotides.

In some embodiments, the methods and devices provided herein can use oligonucleotides that are immobilized on a surface or substrate (e.g., support-bound oligonucleotides) where either the 3' or 5' end of the oligonucleotide is bound to the surface. Support-bound oligonucleotides comprise for example, oligonucleotides complementary to construction oligonucleotides, anchor oligonucleotides and/or spacer oligonucleotides. As used herein the term "support", "substrate" and "surface" are used interchangeably and refers to a porous or non-porous solvent insoluble material on which polymers such as nucleic acids are synthesized or immobilized. As used herein "porous" means that the material contains pores having substantially uniform diameters (for example in the nm range). Porous materials include paper, synthetic filters, polymeric matrices, etc. In such porous materials, the reaction may take place within the pores or matrix. The support can have any one of a number of shapes, such as pin, strip, plate, disk, rod, bends, cylindrical structure, particle, including bead, nanoparticles and the like. The support can have variable widths. The support can be hydrophilic or capable of being rendered hydrophilic. The support can include inorganic powders such as silica, magnesium sulfate, and alumina; natural polymeric materials, particularly cellulosic materials and materials derived from cellulose, such as fiber containing papers, e.g., filter paper, chromatographic paper, etc.; synthetic or modified naturally occurring polymers, such as nitrocellulose, cellulose acetate, poly (vinyl chloride), polyacrylamide, cross linked dextran, agarose, polyacrylate, polyethylene, polypropylene, poly (4-methylbutene), polystyrene, polymethacrylate, poly(ethylene terephthalate), nylon, poly(vinyl butyrate), polyvinylidene difluoride (PVDF) membrane, glass, controlled pore glass, magnetic controlled pore glass, ceramics, metals, and the like etc.; either used by themselves or in conjunction with other materials. In some embodiments, oligonucleotides are synthesized on an array format. For example, single-stranded oligonucleotides are synthesized in situ on a common support wherein each oligonucleotide is synthesized on a separate or discrete feature (or spot) on the substrate. In some embodiments, single-stranded oligonucleotides can be bound to the surface of the support or feature. As used herein the term "array" refers to an arrangement of discrete features for storing, amplifying and releasing oligonucleotides or complementary oligonucleotides for further reactions. In some embodiments, the support or array is addressable: the support includes two or more discrete addressable features at a particular predetermined location (i.e., an "address") on the support. Therefore, each oligonucleotide molecule of the array is localized to a known and defined location on the support. The sequence of each oligonucleotide can be determined from its position on the support.

In some embodiments, oligonucleotides are attached, spotted, immobilized, surface-bound, supported or synthesized on the discrete features of the surface or array. Oligonucleotides may be covalently attached to the surface or deposited on the surface. Arrays may be constructed, custom ordered or purchased from a commercial vendor (e.g., Agilent, Affymetrix, Nimblegen). Various methods of construction are well known in the art e.g., maskless array synthesizers, light directed methods utilizing masks, flow channel methods, spotting methods, etc. In some embodiments, construction and/or selection oligonucleotides may be synthesized on a solid support using maskless array synthesizer (MAS). Maskless array synthesizers are described, for example, in PCT Application No. WO 99/42813 and in corresponding U.S. Pat. No. 6,375,903. Other examples are known of maskless instruments which can fabricate a custom DNA microarray in which each of the features in the array has a single-stranded DNA molecule of desired sequence. Other methods for synthesizing oligonucleotides include, for example, light-directed methods utilizing masks, flow channel methods, spotting methods, pin-based methods, and methods utilizing multiple supports. Light directed methods utilizing masks (e.g., VLSIPS™ methods) for the synthesis of oligonucleotides is described, for example, in U.S. Pat. Nos. 5,143,854, 5,510,270 and 5,527,681. These methods involve activating predefined regions of a solid support and then contacting the support with a preselected monomer solution. Selected regions can be activated by irradiation with a light source through a mask much in the manner of photolithography techniques used in integrated circuit fabrication. Other regions of the support remain inactive because illumination is blocked by the mask and they remain chemically protected. Thus, a light pattern defines which regions of the support react with a given monomer. By repeatedly activating different sets of predefined regions and contacting different monomer solutions with the support, a diverse array of polymers is produced on the support. This process can also be effected through the use of a photoresist which is compatible with the growing surface bound molecules and synthesis chemistries involved. Other steps, such as washing unreacted monomer solution from the support, can be optionally used. Other applicable methods include mechanical techniques such as those described in U.S. Pat. No. 5,384,261. Additional methods applicable to synthesis of oligonucleotides on a single support are described, for example, in U.S. Pat. No. 5,384,261. For example, reagents may be delivered to the support by either (1) flowing within a channel defined on predefined regions or (2) "spotting" on predefined regions. Other approaches, as well as combinations of spotting and flowing, may be employed as well. In each instance, certain activated regions of the support are mechanically separated from other regions when the monomer solutions are delivered to the various reaction sites. Flow channel methods involve, for example, microfluidic systems to control synthesis of oligonucleotides on a solid support. For example, diverse polymer sequences may be synthesized at selected regions of a solid support by forming flow channels on a surface of the support through which appropriate reagents flow or in which appropriate reagents are placed. Spotting methods for preparation of oligonucleotides on a solid support involve delivering reactants in relatively small quantities by directly depositing them in selected regions. In some steps, the entire support surface can be sprayed or otherwise coated with a solution, if it is more efficient to do so. Precisely measured aliquots of monomer solutions may be deposited dropwise by a dispenser that moves from region to region. Pin-based methods for synthesis of oligonucleotides on a solid support are described, for example, in U.S. Pat. No. 5,288,514. Pin-based methods utilize a support having a plurality of pins or other extensions. The pins are each inserted simultaneously into individual reagent containers in a tray. An array of 96 pins is commonly utilized with a 96-container tray, such as a 96-well microtiter dish. Each tray is filled with a particular reagent for coupling in a particular chemical reaction on an individual pin. Accordingly, the trays will often contain different reagents. Since the chemical reactions have been optimized such that each of the reactions can be performed under a relatively similar set of reaction conditions, it becomes possible to conduct multiple chemical coupling steps simultaneously.

In another embodiment, a plurality of oligonucleotides may be synthesized or immobilized on multiple supports. One example is a bead-based synthesis method which is described, for example, in U.S. Pat. Nos. 5,770,358; 5,639,603; and 5,541,061. For the synthesis of molecules such as oligonucleotides on beads, a large plurality of beads is suspended in a suitable carrier (such as water) in a container. The beads are provided with optional spacer molecules having an active site to which is complexed, optionally, a protecting group. At each step of the synthesis, the beads are divided for coupling into a plurality of containers. After the nascent oligonucleotide chains are deprotected, a different monomer solution is added to each container, so that on all beads in a given container, the same nucleotide addition reaction occurs. The beads are then washed of excess reagents, pooled in a single container, mixed and re-distributed into another plurality of containers in preparation for the next round of synthesis. It should be noted that by virtue of the large number of beads utilized at the outset, there will similarly be a large number of beads randomly dispersed in the container, each having a unique oligonucleotide sequence synthesized on a surface thereof after numerous rounds of randomized addition of bases. An individual bead may be tagged with a sequence which is unique to the double-stranded oligonucleotide thereon, to allow for identification during use.

Pre-synthesized oligonucleotide and/or polynucleotide sequences may be attached to a support or synthesized in situ using light-directed methods, flow channel and spotting methods, inkjet methods, pin-based methods and bead-based methods set forth in the following references: McGall et al. (1996) Proc. Natl. Acad. Sci. U.S.A. 93:13555; Synthetic DNA Arrays In Genetic Engineering, Vol. 20:111, Plenum Press (1998); Duggan et al. (1999) Nat. Genet. S21:10; Microarrays: Making Them and Using Them In Microarray Bioinformatics, Cambridge University Press, 2003; U.S. Patent Application Publication Nos. 2003/0068633 and 2002/0081582; U.S. Pat. Nos. 6,833,450, 6,830,890, 6,824,866, 6,800,439, 6,375,903 and 5,700,637; and PCT Publication Nos. WO 04/031399, WO 04/031351, WO 04/029586, WO 03/100012, WO 03/066212, WO 03/065038, WO 03/064699, WO 03/064027, WO 03/064026, WO 03/046223, WO 03/040410 and WO 02/24597; the disclosures of which are incorporated herein by reference in their entirety for all purposes. In some embodiments, pre-synthesized oligonucleotides are attached to a support or are synthesized using a spotting methodology wherein monomers solutions are deposited dropwise by a dispenser that moves from region to region (e.g., ink jet). In some embodiments, oligonucleotides are spotted on a support using, for example, a mechanical wave actuated dispenser.

In some embodiments, each nucleic acid fragment or construct (also referred herein as nucleic acid of interest) being assembled may be between about 100 nucleotides long and about 1,000 nucleotides long (e.g., about 200, about 300, about 400, about 500, about 600, about 700, about 800, about 900). However, longer (e.g., about 2,500 or more nucleotides long, about 5,000 or more nucleotides long, about 7,500 or more nucleotides long, about 10,000 or more nucleotides long, etc.) or shorter nucleic acid fragments may be assembled using an assembly technique (e.g., shotgun assembly into a plasmid vector). It should be appreciated that the size of each nucleic acid fragment may be independent of the size of other nucleic acid fragments added to an assembly. However, in some embodiments, each nucleic acid fragment may be approximately the same size.

Aspects of the invention relate to methods and compositions for the selective isolation of nucleic acid constructs having a predetermined sequence of interest. As used herein, the term "predetermined sequence" means that the sequence of the polymer is known and chosen before synthesis or assembly of the polymer. In particular, aspects of the invention is described herein primarily with regard to the preparation of nucleic acids molecules, the sequence of the oligonucleotide or polynucleotide being known and chosen before the synthesis or assembly of the nucleic acid molecules. In some embodiments of the technology provided herein, immobilized oligonucleotides or polynucleotides are used as a source of material. In various embodiments, the methods described herein use pluralities of construction oligonucleotides, each oligonucleotide having a target sequence being determined based on the sequence of the final nucleic acid constructs to be synthesized (also referred herein as nucleic acid of interest). In one embodiment, oligonucleotides are short nucleic acid molecules. For example, oligonucleotides may be from 10 to about 300 nucleotides, from 20 to about 400 nucleotides, from 30 to about 500 nucleotides, from 40 to about 600 nucleotides, or more than about 600 nucleotides long. However, shorter or longer oligonucleotides may be used. Oligonucleotides may be designed to have different length. In some embodiments, the sequence of the polynucleotide construct may be divided up into a plurality of shorter sequences (e.g. construction oligonucleotides) that can be synthesized in parallel and assembled into a single or a plurality of desired polynucleotide constructs using the methods described herein. Nucleic acids, such as construction oligonucleotides, may be pooled from one or more arrays to form a library or pool of nucleic acids before being processed (e.g. tagged, diluted, amplified, sequenced, isolated, assembled etc.).

According to some aspects of the invention, each nucleic acid sequence to be assembled (also referred herein as nucleic acid source molecules) can comprise an internal predetermined target sequence having a 5' end and a 3' end and additional flanking sequences at the 5' end and/or at the 3' end of the internal target sequence. In some embodiments, the internal target sequences or nucleic acids including the internal target sequences and the additional 5' and 3' flanking sequences can be synthesized onto a solid support as described herein.

In some embodiments, the synthetic nucleic acid sequences comprise an internal target sequence, and non-target sequences upstream and downstream the target sequence. In some embodiments, the non-target sequences can include a sequence ID (SeqID) at the 3' end (downstream) and the 5' end (upstream) of the target sequence for identification of similar target sequences and a sequencing handle (H) at the 3' end and the 5' end of the target sequence for multiplexed sample preparation. The sequencing handle can be at the 3' end and 5' end of the sequence ID. In some embodiments, the sequence ID is 10 nucleotides in length. In some embodiments, the sequencing handle H is 20 nucleotides in length. However shorter and longer sequence ID and/or sequencing handles can be used. In some embodiments, the nucleic acid sequences can be synthesized with additional sequences, such as oligonucleotide tag sequences. For example, the nucleic acid sequences can be designed so that they include an oligonucleotide tag sequence chosen from a library of oligonucleotide tag sequences, as described herein. In some embodiments, the nucleic acid sequences can be designed to have an oligonucleotide tag sequence including a sequence common across a set of nucleic acid constructs. The term "common sequence" means that the sequences are identical. In some embodiments, the common sequences can be universal sequences. Yet in other embodiments, the 5' oligonucleotide tag sequences are designed to have common sequences at their 3' end and the 3' oligonucleotide tag sequences are designed to have common sequences at their 5' end. For example, the nucleic acid can be designed to have a common sequence at the 3' end of the 5' oligonucleotide tag and at the 5' end of the 3' oligonucleotide tag. The library of oligonucleotide tag sequences can be used for nucleic acid construct to be assembled from a single array. Yet in other embodiments, the library of oligonucleotide tags can be reused for different constructs produced from different arrays. In some embodiments, the library of oligonucleotide tag sequences can be designed to be universal. In some embodiments, the nucleic acid or the oligonucleotide tags are designed to have additional sequences. The additional sequences can comprise any nucleotide sequence suitable for nucleic acid sequencing, amplification, isolation or assembly in a pool.

Preparative In Vitro Cloning (IVC) Methods

Provided herein are preparative in vitro cloning methods or strategies for de novo high fidelity nucleic acid synthesis. In some embodiments, the in vitro cloning methods can use oligonucleotide tags. Yet in other embodiments, the in vitro cloning methods do not necessitate the use of oligonucleotide tags.

In some embodiments, the methods described herein allow for the cloning of nucleic acid sequences having a desired or predetermined sequence from a pool of nucleic acid molecules. In some embodiments, the methods may include analyzing the sequence of target nucleic acids for parallel preparative cloning of a plurality of target nucleic acids. For example, the methods described herein can include a quality control step and/or quality control readout to identify the nucleic acid molecules having the correct sequence. FIGS. 1A-C show an exemplary method for isolating and cloning nucleic acid molecules having predetermined sequences. In some embodiments, the nucleic acid can be first synthesized or assembled onto a support. For example, the nucleic acid molecules can be assembled in a 96-well plate with one construct per well. In some embodiments, each nucleic acid construct ($C_1$ through $C_N$, FIGS. 1A-C) has a different nucleotide sequence. For example, the nucleic acid constructs can be non-homologous nucleic acid sequences or nucleic acid sequences having a certain degree of homology. Yet in other embodiments, a plurality of nucleic acid molecules having a predefined sequence, e.g. $C_1$ through $C_N$, can be deposited at different location or well of a solid support. In some embodiments, the limit of the length of the nucleic acid constructs can depend on the efficiency of sequencing the 5' end and the 3' end of the full length target nucleic acids via high-throughput paired end sequencing. One skilled in the art will appreciate that the methods described herein can bypass the need for cloning via the transformation of cells with nucleic acid constructs in propagatable vectors (i.e. in vivo cloning). In addition, the methods described herein eliminate the need to amplify candidate constructs separately before identifying the target nucleic acids having the desired sequences.

One skilled in the art would appreciate that after oligonucleotide assembly, the assembly product may contain a pool of sequences containing correct and incorrect assembly products. For example, referring to FIG. 1A, each well of the plate (nucleic acid construct $C_1$ through $C_N$) can be a mixture of nucleic acid molecules having correct or incorrect sequences (incorrect sequence sites being represented by a star). The errors may result from sequence errors introduced during the oligonucleotide synthesis, or during the assembly of oligonucleotides into longer nucleic acids. In some instances, up to 90% of the nucleic acid sequences may be unwanted sequences. Devices and methods to selectively isolate the correct nucleic acid sequence from the incorrect nucleic acid sequences are provided herein. The correct sequence may be isolated by selectively isolating the correct sequence(s) from the other incorrect sequences as by selectively moving or transferring the desired assembled polynucleotide of predefined sequence to a different feature of the support, or to another plate. Alternatively, polynucleotides having an incorrect sequence can be selectively removed from the feature comprising the polynucleotide of interest. According to some methods of the invention, the assembly nucleic acid molecules may first be diluted within the solid support in order to obtain a normalized population of nucleic acid molecules. As used herein, the term "normalized" or "normalized pool" means a nucleic acid pool that has been manipulated, to reduce the relative variation in abundance among member nucleic acid molecules in the pool to a range of no greater than about 1000-fold, no greater than about 100-fold, no greater than about 10-fold, no greater than about 5-fold, no greater than about 4-fold, no greater than about 3-fold or no greater than about 2-fold. In some embodiments, the nucleic acid molecules are normalized by dilution. For example, the nucleic acid molecules can be normalized such as the number of nucleic acid molecules is in the order of about 5, about 10, about 20, about 30, about 40, about 50, about 60, about 60, about 70, about 80, about 90, about 100, about 1000 or higher. In some embodiments, each population of nucleic acid molecules can be normalized by limiting dilution before pooling the nucleic acid molecules to reduce the complexity of the pool. In some embodiments, to ensure that at least one copy of the target nucleic acid sequence is present in the pool, dilution is limited to provide for more than one nucleic acid molecule. In some embodiments, the oligonucleotides can be diluted serially. In some embodiments, the device (for example, an array or microwell plate, such as 96 wells plate) can integrate a serial dilution function. In some embodiments, the assembly product can be serially diluted to a produce a normalized population of nucleic acids. The concentration and the number of molecules can be assessed prior to the dilution step and a dilution ratio is calculated in order to produce a normalized population. In an exemplary embodiment, the assembly product is diluted by a factor of at least 2, at least 3, at least 4, at least 5, at least 6, at least 7, at least 10, at least 20, at least 50, at least 100, at least 1,000 etc. . . . . In some embodiments, prior to sequencing, the target nucleic acid sequences can be diluted and placed for example, in distinct wells or at distinct locations of a solid support or on distinct supports.

In some embodiments, the normalized populations of nucleic acid molecules can be pooled to create a pool of nucleic acid molecules having different predefined sequences. In some embodiments, each nucleic acid molecule in the pool can be at a relatively low complexity. Yet in other embodiments, normalization of the nucleic acid molecules can be performed after mixing the different population of nucleic acid molecules present at high concentration.

Figure 2A:
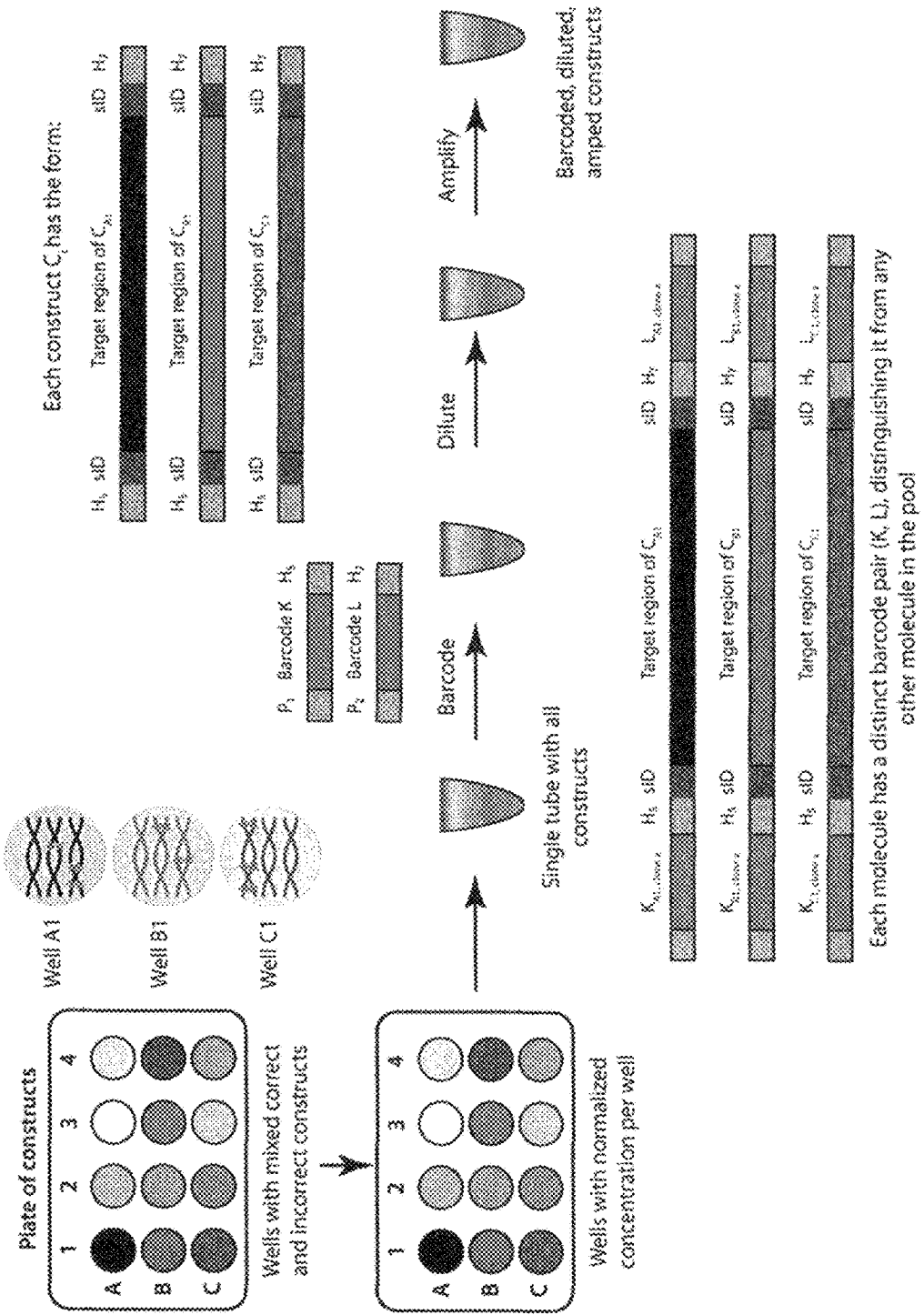
FIG. 2A illustrates a non-limiting exemplary method of preparative in vitro cloning sample preparation according to some embodiments.
Figure 2B:
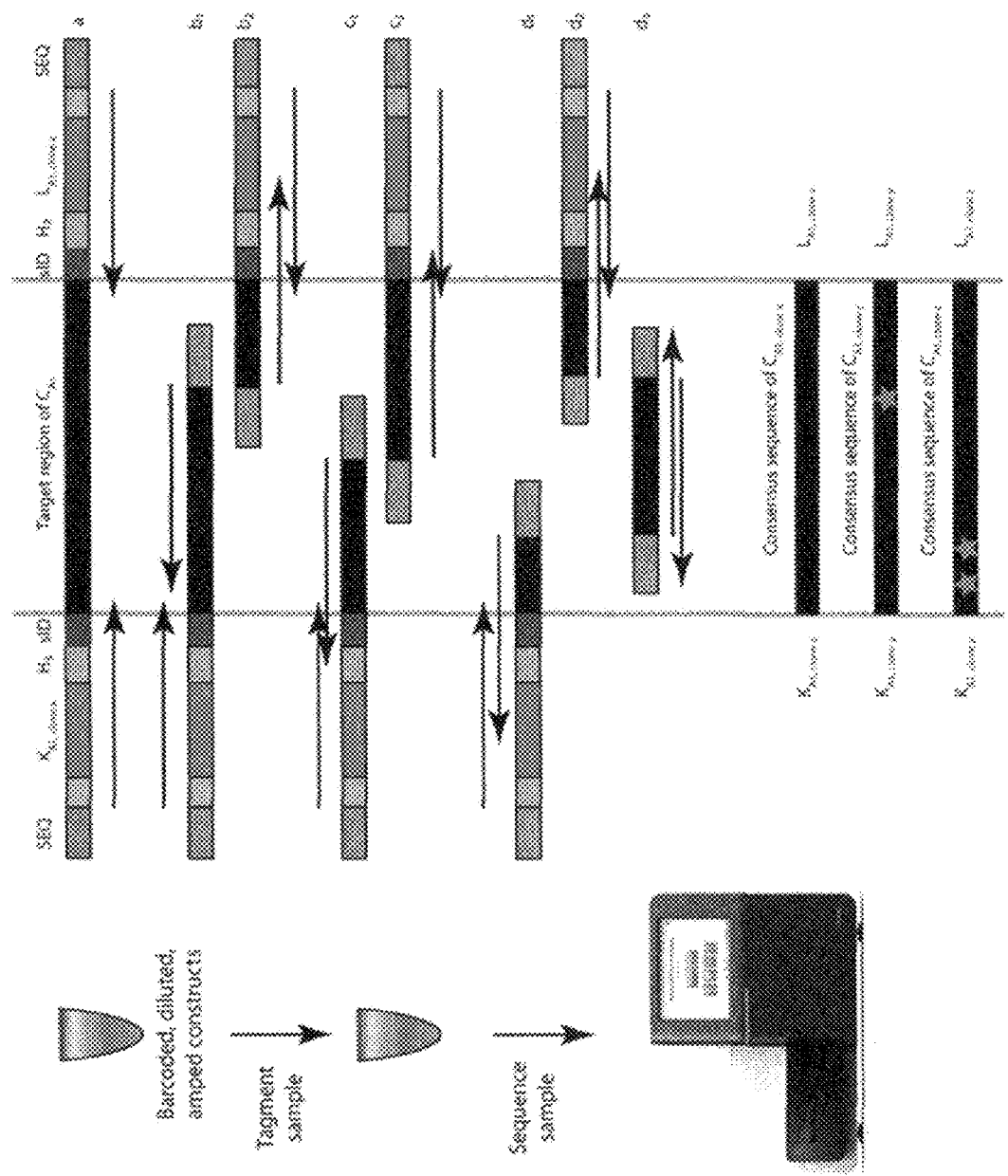
FIG. 2B illustrates a non-limiting exemplary method of preparative in vitro cloning sequencing according to some embodiments.
Figure 2C:
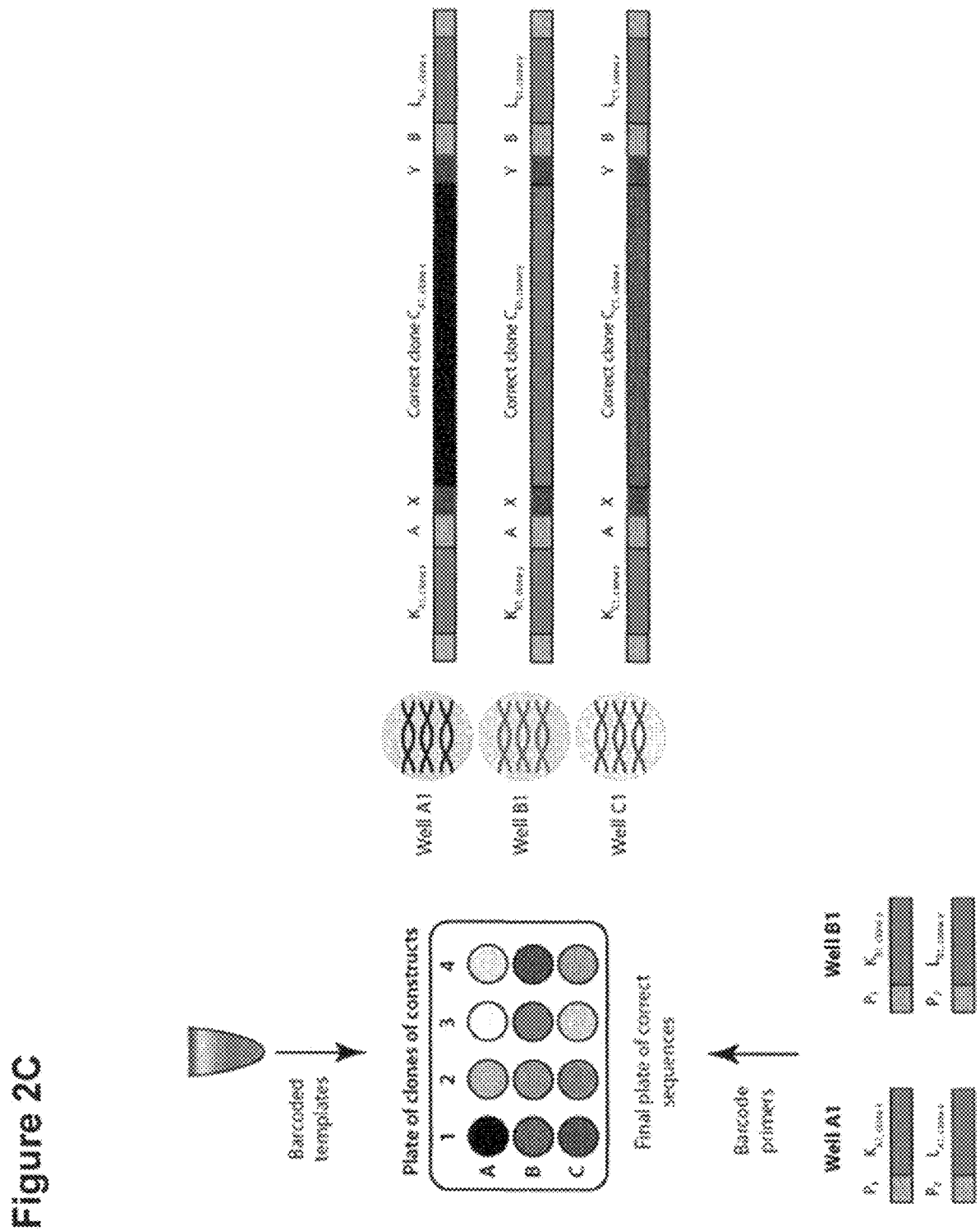
FIG. 2C illustrates a non-limiting exemplary method of in vitro cloning preparative isolation according to some embodiments

Yet in other embodiments, the methods of the invention comprise the following steps as illustrated in FIG. 2A: (a) providing a pool of different nucleic acid constructs (also referred herein as source molecules); (b) providing a repertoire of oligonucleotide tags, each oligonucleotide tag comprising a unique nucleotide tag sequence or barcode; (c) attaching at the 5' end and at the 3' end an oligonucleotide tag (K and L) to each source molecule in the pool of nucleic acid molecules, such that substantially all different molecules in the pool have a different oligonucleotide tag pair (K, L) attached thereto and so as to associate a barcode to a specific source molecule, and (d) diluting the tagged nucleic acid sequences; (e) obtaining a paired end read for each nucleic acid molecule; and (f) sorting the nucleic acid molecules having the desired predetermine sequence according to the identity of the barcodes. As used herein, the term "barcode" refers to a unique oligonucleotide tag sequence that allows a corresponding nucleic acid sequence to be identified. By designing the repertoire or library of barcodes to form a library of barcodes large enough relative to the number of nucleic acid molecules, each different nucleic acid molecule can have a unique barcode pair. In some embodiments, the library of barcodes comprises a plurality of 5' end barcodes and a plurality of 3' end barcodes. Each 5' end barcode of the library can be design to have 3' end or internal sequence common to each member of the library. Each 3' end barcode of the library can be design to have 5' end or internal sequence common to each member of the library In some embodiments, the methods further comprise digesting the tagged source molecules using Nextera™ tagmentation and sequencing using MiSeq®, HiSeq® or higher throughput next generation sequencing platforms. The Nextera™ tagmented paired reads generally generate one sequence with an oligonucleotide tag sequence for identification, and another sequence internal to the construct target region (as illustrated in FIG. 2C). With high throughput sequencing, enough coverage can be generated to reconstruct the consensus sequence of each tag pair construct and determine if the sequence is correct (i.e. error-free sequence).

In some embodiments, the nucleic acid molecules can be pooled from one or more solid supports for multiplex processing. The nucleic acid molecules can be diluted to keep a tractable number of clones per target nucleic acid molecule. Each nucleic acid molecule can be tagged by adding a unique barcode or pair of unique barcodes to each end of the molecule. Diluting the nucleic acid molecules prior to attaching the oligonucleotide tags can allow for a reduction of the complexity of the pool of nucleic acid molecules thereby enabling the use of a library of barcodes of reduced complexity. The tagged molecules can then be amplified. In some embodiments, the oligonucleotide tag sequence can comprise a primer binding site for amplification (FIG. 2C). In some embodiments, the oligonucleotide tag sequence can be used as a primer-binding site. Amplified tagged molecules can be subjected to tagmentation and subjected to paired-read sequencing to associate barcodes with the desired target sequence. The barcodes can be used as primers to recover the sequence clones having the desired sequence. Amplification methods are well know in the art. Examples of enzymes with polymerase activity which can be used for amplification by PCR are NA polymerase (Klenow fragment, T4 DNA polymerase), heat stable DNA polymerases from a variety of thermostable bacteria (Taq, VENT, Pfu or Tfl DNA polymerases) as well as their genetically modified derivatives (TaqGold, VENTexo, Pfu exo), or KOD Hifi DNA polymerases. In some embodiments, amplification by chimeric PCR can reduce signal to noise of barcode association.

In other embodiments, the nucleic acid molecules can be pooled from one or more array for multiplex processing. As described herein, the nucleic acid molecules can be designed to include a barcode at the 5' and at the 3' ends. In some embodiments, the barcodes can have common sequences within and across a set of constructs. For example, the barcodes can be universal for each construct assembled from a single array. In some embodiments, the barcodes can have common junction sequences or common primer binding site sequences.

In some embodiments, barcodes can be added to the nucleic acid molecules and tagged nucleic acid molecules can be diluted before being subjected to amplification. Amplified tagged molecules can be subjected to tagmentation and sequenced to associate the barcode pairs to each nucleic acid molecule. In some embodiments, one read of each read pair is used for sequencing barcoded end. The read pairs without any barcodes can be filtered out. Sequencing error rate can be removed by consensus calling. Nucleic acid molecules having the desired sequence can be isolated for example using the barcodes as primers.

According to some methods of the invention, the nucleic acid sequences (construction oligonucleotides, assembly intermediates or assembled nucleic acid of interest) may first be diluted in order to obtain a clonal population of target polynucleotides (i.e. a population containing a single target polynucleotide sequence). As used herein, a "clonal nucleic acid" or "clonal population" or "clonal polynucleotide" are used interchangeably and refer to a clonal molecular population of nucleic acids, i.e. to nucleic acids that are substantially or completely identical to each other. Accordingly, the dilution based protocol provides a population of nucleic acid molecules being substantially identical or identical to each other. In some embodiments, the polynucleotides can be diluted serially. The concentration and the number of molecules can be assessed prior to the dilution step and a dilution ratio can be calculated in order to produce a clonal population.

In some embodiments, next-generation sequencing (NGS) spot location or microfluidic channel location can act as a nucleic acid construct identifier eliminating the need for designing construct specific barcodes.

In some embodiments, when using NGS with multiple flow cells (e.g. Hiseq® 2000), it is possible to obtain an average of one clone of each gene per flow cell. As determined by the Poisson distribution, limiting dilution should result in a single-hit, e.g. one clone per well. Poisson statistics gives that if the average number of clones of each gene is one per flow cell then approximately ⅓ of the flow cells will have 0 clones, ⅓ will have 1 clone and ⅓ will have 2 clones. Therefore, if the error rate is such that N clones are required in order to yield a perfect or error-free full length construct, then 3*N flow cells would be required to have high likelihood that at least one flow cell will contain a clonal representation of the perfect construct. For example, if N=4, 12 flow cells would be required. In some embodiments, after sequencing the clones inside the flow cell, means can be provided for collecting the effluent of each flow cell into separate wells. Sequencing data can then used to identify the collection wells that contain the nucleic acid(s) having the predetermined sequence. After determination of which nucleic acids having the predetermined sequence are in which collection wells, primers that are specific to the nucleic acids having the predetermined sequences may then be used to amplify nucleic acids having the predetermined sequences from their appropriate well. In such embodiments, primers can be complementary of the nucleic acid sequences of interest and/or oligonucleotide tags.

Tag Oligonucleotides

In some embodiments, the 5' end and the 3' end of each nucleic acid molecules within the pool can be tagged with a pair of tag oligonucleotide sequence. In some embodiments, the tag oligonucleotide sequence can be composed of common DNA primer regions and unique "barcode" regions such as a specific nucleotide sequence. In some embodiments, the number of tag nucleotide sequences can be greater than the number of molecules per construct (i.e. 10-1000 molecules in the dilution).

In some embodiments, the barcode sequence may also act as a primer binding site to amplify the barcoded nucleic acid molecules or to isolate the nucleic acid molecules having the desired predetermined sequence. In such embodiments, the term barcode and oligonucleotide tag can be used interchangeably. In such embodiments, the terms "barcoded nucleic acids" and "tagged nucleic acids" can be used interchangeably. It should be appreciated that the oligonucleotide tags may be of any suitable length and composition. In some embodiments, the oligonucleotide tags can be designed such as (a) to allow generation of a sufficient large repertoire of barcodes to allow each nucleic acid molecule to be tagged with a unique barcode at each end; and (b) to minimize cross hybridization between different barcodes. In some embodiments, the nucleotide sequence of each barcode is sufficiently different from any other barcode of the repertoire so that no member of the barcode repertoire can form a dimer under the reactions conditions, such as the hybridization conditions, used.

In some embodiments, the barcode sequence can be 6 bp, 7 bp, 8 bp, 9 bp, 10 bp, 12 bp, 13 bp, 14 bp, 15 bp, 16 bp, 17 bp, 18 bp, 19 bp, 20 bp, 21 bp, 22 bp, 23 bp, 24 bp, 25 bp, 26 bp, 27 bp, 28 bp, 29 bp, 30 bp or more than 30 bp in length. In some embodiments, the 5' end barcode sequence and the 3' end barcode sequence can differ in length. For example, the 5' barcode can be 14 nucleotides in length and the 3' barcode can be 20 nucleotides in length. In some embodiments, the length of the barcode can be chosen to minimize reduction in barcode space, maximize barcode space at the 3' end for primability, allows error correction for barcodes, and/or minimize the variation of barcode melting temperatures. For example, the melting temperatures of the barcodes within a set can be within 10° C. of one another, within 5° C. of one another or within 2° C. of one another.

Each barcode sequence can include a completely degenerate sequence, a partially degenerate sequence or a non-degenerate sequence.

For example, a 6 bp, 7 bp, 8 bp, or longer nucleotide tag can be used. In some embodiments, a degenerate sequence NNNNNNNN (8 degenerate bases, wherein each N can be any natural or non-natural nucleotide) can be used and generates 65,536 unique barcodes. In some embodiments, the length of the nucleotide tag can be chosen such as to limit the number of pairs of tags that share a common tag sequence for each nucleic acid construct.

One of skill in the art would appreciate that a completely degenerate sequence can give rise to a high number of different barcodes but also to higher variations in primer melting temperature Tm. Melting temperature is the temperature at which a population of double-stranded nucleic acid molecules becomes half dissociated into single-strands. Equations for calculating the Tm of nucleic acids are well known in the art. For example, a simple estimate of the Tm value can be calculated by the equation $Tm = 81.5 \pm 0.41$ (% G+C) when the nucleic acid are in aqueous solution at IM NaCl. In some embodiments, the barcode sequences are coded barcode and may comprise a partially degenerate sequence combined with fixed or constant nucleotides. In some embodiments, the barcodes can include one or more of the following: (a) degenerate bases N at the 3' end; (b) one or more C at the 5' end (to restrict the Tm); (c) stretch comprising W, D, H, S, B, V and M.

In some embodiments, the barcodes are coded barcodes and may include, but are not limited to, a library of barcodes having the following sequences:

Barcode 1: CCWSWDHSHDBVHDNNNNMM. This 20 bases barcode has the same barcode degeneracy space than 13N.

Barcode 2: CCSWSWHDSDHVBDHNNNNMM. This 21 bases barcode has some degenerate bases switched in location as compared to Barcode 1. It should be noted that primers can be distinguished between Barcode 1 and Barcode 2.

In some embodiments, barcodes sequences can be designed, analyzed and ranked to generate a ranked list of nucleotide tags that are enriched for both perfect sequence and primer performance. It should be appreciated that the coded barcodes provide a method for generating primers with tighter Tm range.

In some embodiments, the tag oligonucleotide sequences or barcodes can be joined to each nucleic acid molecule to form a nucleic acid molecule comprising a tag oligonucleotide sequence at its 5' and 3' ends. In some embodiments, the tag oligonucleotide sequences or barcodes can be ligated to blunt end nucleic acid molecules using a ligase. For example, the ligase can be a T7 ligase or any other ligase capable of ligating the tag oligonucleotide sequences to the nucleic acid molecules. Ligation can be performed under conditions suitable to avoid concatamerization of the nucleic acid constructs. In other embodiments, the nucleic acid molecules are designed to have at their 5' and 3' ends a sequence that is common or complementary to the tag oligonucleotide sequences. In some embodiments, the tag oligonucleotide sequences and the nucleic acid molecules having common sequences can be joined as adaptamers by polymerase chain reaction. As illustrated in FIG. 2A, barcodes can be joined at the 5' end and the 3' end of the sequencing handle H (A and B), which are flanking the internal target sequence. In some embodiments, each source molecule synthesized on a first solid support has a common pair of sequencing handles at its 5' and 3' end. For example, oligonucleotides synthesized on a first solid support has a first pair of sequencing handles (A1, B1), and oligonucleotides synthesized on a second solid support has a second pair of sequencing handles (A2, B2), etc. . . .

Figure 4:
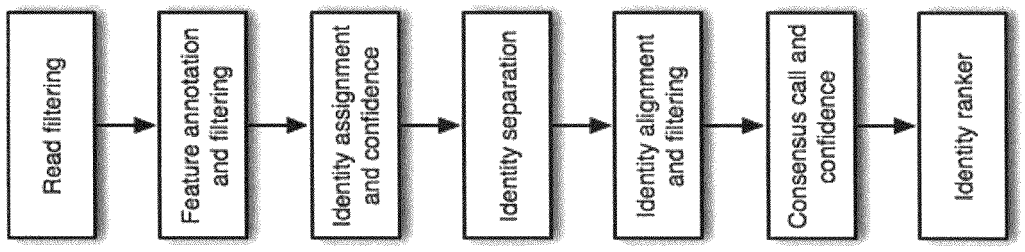
FIG. 4 illustrates a non-limiting exemplary flow chart for sequencing data analysis.

Yet in other embodiments, barcoding can be introduced by ligation to the 5' end and the 3' end of a nucleic acid molecule without the addition of sequence identifiers SeqID and/or sequencing handles H. Accordingly, the construct primers are still intact and can act as sequence identifiers. This process can have the advantage to use nucleic acid constructs having an internal target sequence and a primer region at the 5' end and the 3' end of the target sequence as synthesized onto an array and to have greater control to normalize the construct. In some embodiments, the barcoding can be introduced using a plasmid-based methodology as illustrated in FIG. 4 comprising the steps of (1) providing a barcoded vector (e.g. pUC19 vector), (2) providing a nucleic assembly construct or oligonucleotide, (3) phosphorylating the nucleic acid constructs; (4) ligating the barcoded vector and the nucleic assembly constructs, and (5) pooling ligation products; and (6) subjecting the ligation products to dilution and/or amplification. For example, the linearized vector comprises 5' and 3' flanking regions. In some embodiments, the flanking regions may be designed to have an external barcode and internal sequence adaptors. For example, the flanking regions can comprise a barcode, a tagmentation adaptor and M13 sequences. It should be appreciated that this alternative barcoding scheme is not necessarily plasmid-based and that any linear nucleic acid fragment having a barcode at its 5' end and 3' end can be used.

Figure 3:
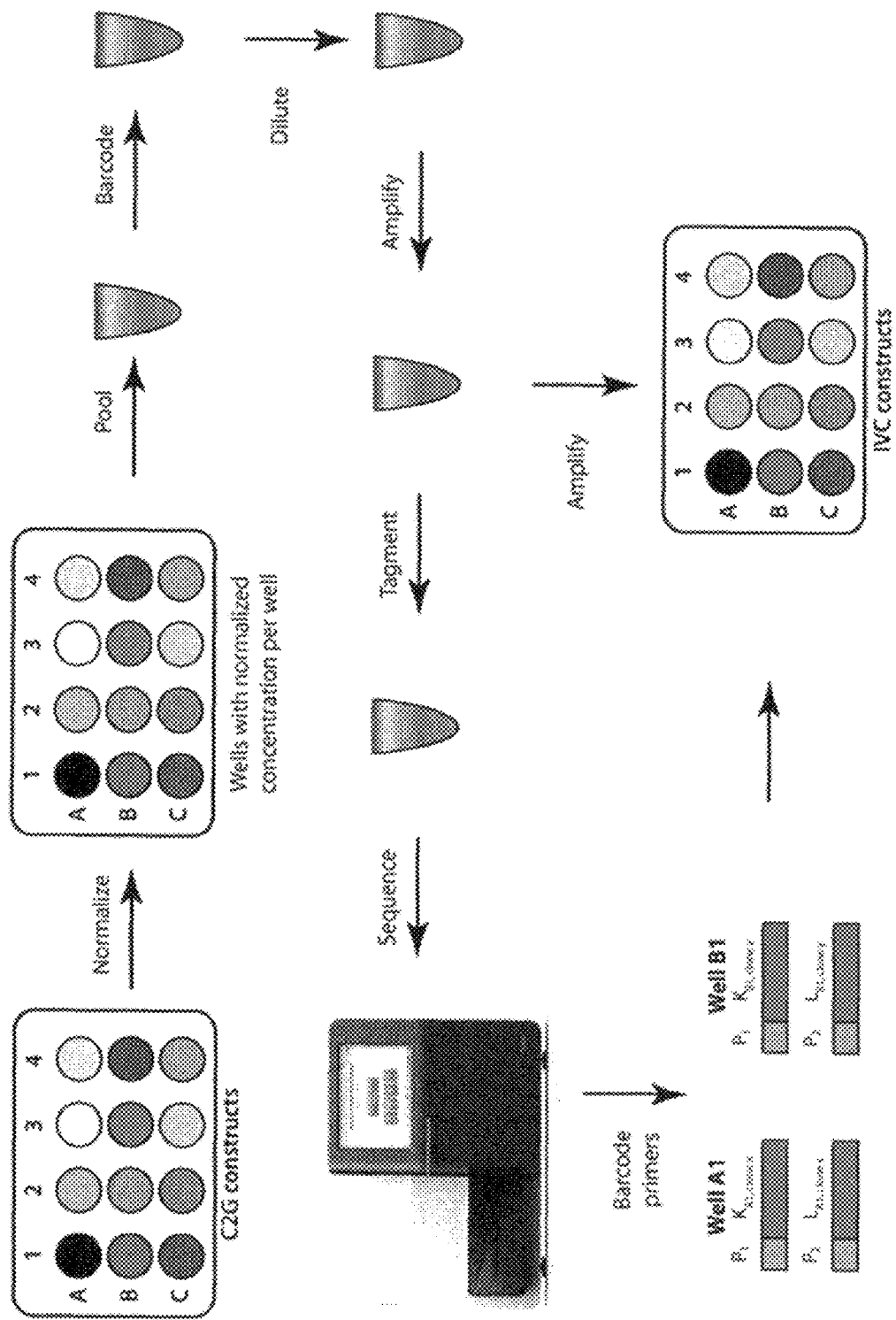
FIG. 3 illustrates a non-limiting exemplary sample processing from nucleic acid constructs (C2G constructs) to in vitro cloning constructs (IVC constructs).

FIG. 3 illustrates the workflow of the foregoing process of tagging a population of target nucleic acid sequences with an oligonucleotide tag, sequencing the molecules to get both the oligonucleotide tag and the internal target sequencing information, and recovering the desired tagged construct sequences. The flow for this workflow/invention could be simplified as: population of target molecules (A)=>tag (B)=>sequencing (C)=>recover desired target nucleic sequence (D).

Figure 12:
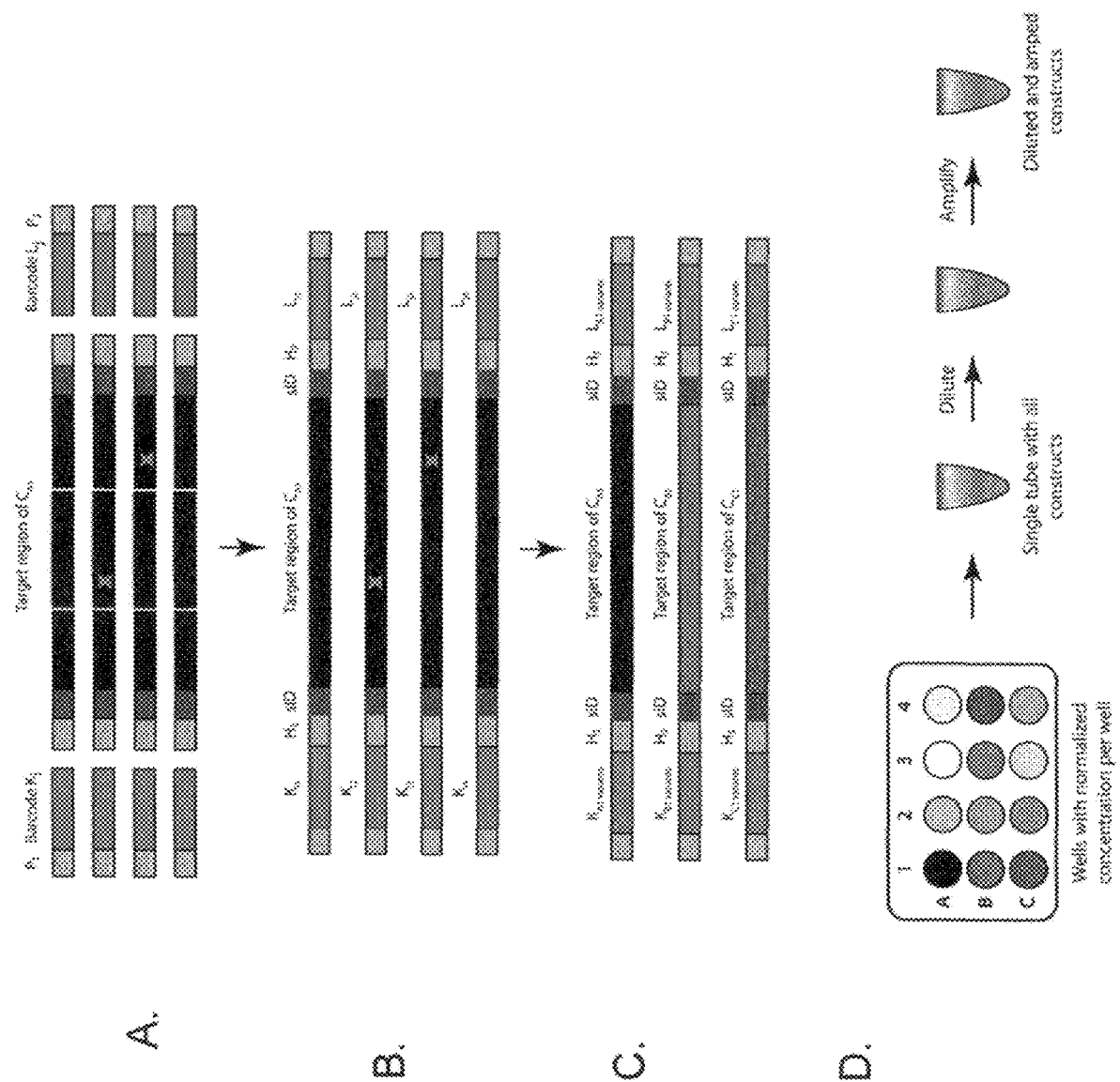
FIG. 12 illustrates a non-limiting example of in vitro cloning integration with assembly.

Yet in other embodiments, and referring to FIGS. 12A-B, the nucleic acid constructs can be assembled from a plurality of internal target sequence fragments and unique barcode sequences. The unique barcode sequences can be designed to be assembled at the 5' end and 3' end of the internal target sequence simultaneously with the target sequences, to create a population of molecules having unique flanking barcoding sequences and interior target regions of interest. In some embodiments, the 5' end internal target sequence fragment is designed to have at its 5' end a sequence identifier SeqID and/or sequencing handle H and the 3' end internal target sequence fragments is designed to have at its 3' end a sequence identifies SeqID and/or sequencing handle H. Such process has the advantage to integrate the in vitro cloning process (IVC process) with the assembly process (also referred herein as C2G assembly process). As illustrated in FIG. 12A-B, each assembled molecule having the internal target of interest has a distinct pair ($K_i$, $L_i$), such as ($K_{i1}$, $L_{i1}$), ($K_{i2}$, $L_{i2}$) etc. . . . of sequences distinguishing it from other molecules in a pool of nucleic acid constructs. In some embodiments, a plurality of constructs having different internal target sequences of interest (for example $C_{A1}$, $C_{B1}$ and $C_{C1}$) can be mixed in a pool (FIG. 12C). The different constructs can be diluted, amplified and sequenced as described herein and as illustrated in FIG. 12D. The nucleic acid molecules having the desired sequence can be sorted according to the identity of the corresponding unique pair of barcodes.

One of skill in art will appreciate that the foregoing process has the advantage not to subject the constructs to tagging process, as the core population of molecules is essentially already equivalent to process point B in the workflow above. The workflow could then be described as follow: population of unique target molecules (A')=>sequencing (C)=>recover desired target nucleic sequence (D).

Sequencing

In some embodiments, the target nucleic acid sequence or a copy of the target nucleic acid sequence can be isolated from a pool of nucleic acid sequences, some of them containing one or more sequence errors. As used herein, a copy of the target nucleic acid sequence refers to a copy using template dependent process such as PCR. In some embodiments, sequence determination of the target nucleic acid sequences can be performed using sequencing of individual molecules, such as single molecule sequencing, or sequencing of an amplified population of target nucleic acid sequences, such as polony sequencing. In some embodiments, the pool of nucleic acid molecules are subjected to high throughput paired end sequencing reactions, such as using the HiSeq®, MiSeq® (Illumina) or the like or any suitable next-generation sequencing system (NGS).

In some embodiments, the nucleic acid molecules are amplified using the common primer sequences on each tag oligonucleotide sequence. In some embodiments, the primer can be universal primers or unique primer sequences. Amplification allows for the preparation of the target nucleic acids for sequencing, as well as to retrieve the target nucleic acids having the desired sequences after sequencing. In some embodiments, a sample of the nucleic acid molecules is subjected to transposon-mediated fragmentation and adapter ligation to enable rapid preparation for paired end reads using high throughput sequencing systems. For example, the sample can be prepared to undergo Nextera™ tagmentation (Illumina).

One skilled in the art will appreciate that it can be important to control the extent of the fragmentation and the size of the nucleic acid fragments to maximize the number of reads in the sequencing paired reads and thereby allow for sequencing the desired length of the fragment. In some embodiments, the paired end reads can generate one sequence with a tag for identification, and another sequence which is internal to the construct target region. With high throughput sequencing, enough coverage can be generated to reconstruct the consensus sequence of each tag pair construct and determine if the construct sequence is correct. In some embodiments, it is preferable to limit the number of breakage to less than 2, less than 3, or less than 4. In some embodiments the extent of the fragmentation and/or the size of the fragments can be controlled using appropriate reaction conditions such as by using the suitable concentration of transposon enzyme and controlling the temperature and time of incubation. Suitable reaction conditions can be obtained by using known amounts of a test library and titrating the enzyme and time to build a standard curve for actual sample libraries. In some embodiments, a portion of the sample which is not used for fragmentation can be mixed back into the fragmented sample and processed for sequencing.

The sample can then be sequenced on a platform that generates paired end reads. Depending on the size of the individual DNA constructs, the number of constructs mixed together, and the estimated error rate of the populations, the appropriate platform can be chosen to maximize the number of reads desired and minimize the cost per construct.

The sequencing of the nucleic acid molecules results in reads with both of the tags from each molecule in the paired end reads. The paired end reads can be used to identify which pairs of tags were ligated or PCR joined and the identity of the molecule.

Data Analysis

Figure 5:
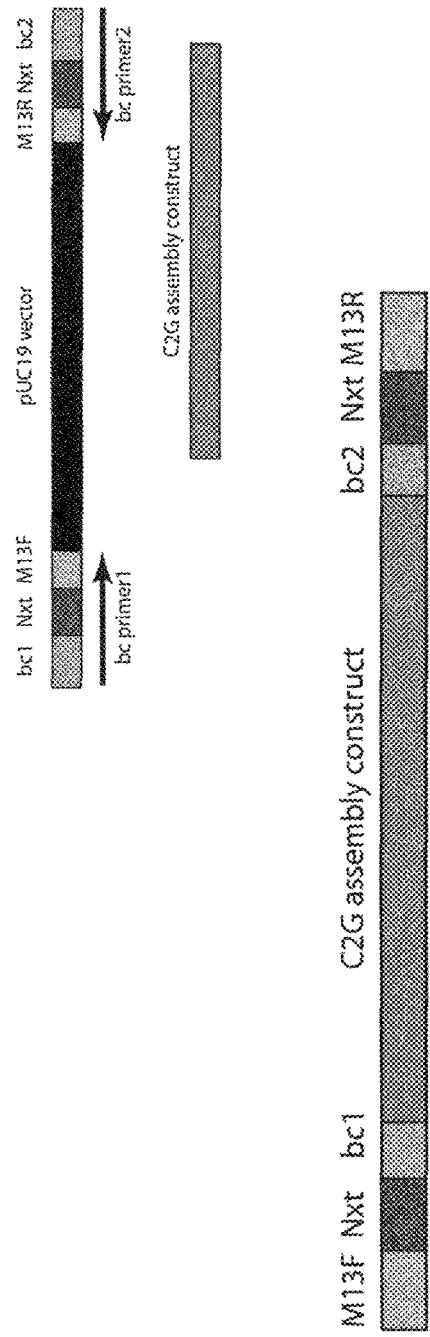
FIG. 5 illustrates a non-limiting exemplary alternative scheme of plasmid-based barcoding.

In some embodiments, sequencing data or reads are analyzed according to the scheme of FIG. 5. A read can represent consecutive base calls associated with a sequence of a nucleic acid. It should be understood that a read could include the full length sequence of the sample nucleic acid template or a portion thereof such as the sequence comprising the barcode sequence, the sequence identifier, and a portion of the target sequence. A read can comprise a small number of base calls, such as about eight nucleotides (base calls) but can contain larger numbers of base calls as well, such as 16 or more base calls, 25 or more base calls, 50 or more base calls, 100 or more base calls, or 200 or more nucleotides or base calls.

For data analysis, reads for which one tag is paired with multiple other tags for the same construct are discarded, because this would result in ambiguity as to which clone the data came from.

The sequencing results can then be analyzed to determine the sequences of each clone of each construct. For each paired read where one read contains a tag sequence, the identity of the molecule each sequencing read comes from is known, and the construct sequence itself can be used to distinguish between constructs with the same tag. The other read from the paired read can be used to build a consensus sequence of the internal regions of the molecule. From these results, a mapping of tag pairs corresponding to correct target sequence for each construct can be generated.

According to one embodiment, the analysis can comprise one or more of the following: (1) feature annotation; (2) feature correction; (3) identity assignment and confidence; (4) consensus call and confidence; and (5) preparative isolation.

Aspects of the invention provide the ability to generate a consensus sequence for each nucleic acid construct. Each base called in a sequence can be based upon a consensus base call for that particular position based upon multiple reads at that position. These multiple reads are then assembled or compared to provide a consensus determination of a given base at a given position, and as a result, a consensus sequence for the particular sequence construct. It will be appreciated that any method of assigning a consensus determination to a particular base call from multiple reads of that position of sequence, are envisioned and encompassed by the present invention. Methods for determining such call are known in the art. Such methods can include heuristic methods for multiple-sequence alignment, optimal methods for multiple sequences alignment, or any methods know in the art. In some embodiments, the sequence reads are aligned to a reference sequence (e.g. predetermined sequence of interest). High throughput sequencing requires efficient algorithms for mapping multiple query sequences such as short reads of the sequence identifiers or barcodes to such reference sequences.

According to some aspects of the invention, feature annotation comprises finding primary features and secondary features. For example, using alignment of the two reads of sequence identifiers SeqID in a read pairs allow for filtering constructs that do not have the correct sequence identifiers at the 5' end and 3' end of the constructs or do not have the correct sequences of the barcodes at the 5' end and the 3' end of the sequence identifiers. In some embodiments, the Levenshtein distance can be used to cluster clones and thereby correct features. Clones can then be ranked based on confidence in identity assignment.

Isolation of Target Nucleic Acid Sequences

Aspects of the invention are especially useful for isolating nucleic acid sequences of interest from a pool comprising nucleic acid sequences comprising sequences errors. The technology provided herein can embrace any method of non-destructive sequencing. Non-limiting examples of non-destructive sequencing include pyrosequencing, as originally described by Hyman et al., (1988, Anal. Biochem. 74: 324-436) and bead-based sequencing, described for instance by Leamon et al., (2004, Electrophoresis 24: 3769-3777). Non-destructive sequencing also includes methods using cleavable labeled oligonucleotides, as the above described Mitra et al., (2003, Anal. Biochem. 320:55-62) and photocleavable linkers (Seo et al., 2005, PNAS 102: 5926-5933). Methods using reversible terminators are also embraced by the technology provided herein (Metzker et al, 1994, NAR 22: 4259-4267). Further methods for non-destructive sequencing (including single molecule sequencing) are described in U.S. Pat. Nos. 7,133,782 and 7,169,560 which are hereby incorporated by reference.

Methods to selectively extract or isolate the correct sequence from the incorrect sequences are provided herein. The term "selective isolation", as used herein, can involve physical isolation of a desired nucleic acid molecule from others as by selective physical movement of the desired nucleic acid molecule, selective inactivation, destruction, release, or removal of other nucleic acid molecules than the nucleic acid molecule of interest. It should be appreciated that a nucleic acid molecule or library of nucleic acid constructs may include some errors that may result from sequence errors-introduced during the oligonucleotides synthesis, the synthesis of the assembly nucleic acids and/or from assembly errors during the assembly reaction. Unwanted nucleic acids may be present in some embodiments. For example, between 0% and 50% (e.g., less than 45%, less than 40%, less than 35%, less than 30%, less than 25%, less than 20%, less than 15%, less than 10%, less than 5% or less than 1%) of the sequences in a library may be unwanted sequences.

In some embodiments, the target having the desired sequence can be recovered using the methods for recovery of the annotated correct target sequences disclosed herein. In some embodiments, the tag sequence pairs for each correct target sequence can be used to amplify by PCR the construct from the sample pool (as illustrated in FIG. 1C, step IV). It should be noted that since the likelihood of the same pair being used for multiple molecules is extremely low, the likelihood to isolate the nucleic acid molecule having the correct sequence is high. Yet in other embodiments, the nucleic acid having the desired sequence can be recovered directly from the sequencer. In some embodiments, the identity of a full length construct can be determined once the pairs of tags are identified. In principle, the location of the full length read (corresponding to a paired end read with the 5' and 3' tags) can be determined on the original sequencing flow cell. After locating the cluster on the flow cell surface, molecules can be eluted or otherwise captured from the surface.

In some embodiment, nucleic acids can be sequenced in a sequencing channel. In some embodiments, the nucleic acid constructs can be sequenced in situ on the solid support used in gene synthesis and reused/recycled therefrom. Analysis of the sequence information from the oligonucleotides permits the identification of those nucleic acid molecules that appear to have desirable sequences and those that do not. Such analysis of the sequence information can be qualitative, e.g., providing a positive or negative answer with regard to the presence of one or more sequences of interest (e.g., in stretches of 10 to 120 nucleotides). In some embodiments, target nucleic acid molecules of interest can then be selectively isolated from the rest of the population. The sorting of individual nucleic acid molecules can be facilitated by the use of one or more solid supports (e.g. bead, insoluble polymeric material, planar surface, membrane, porous or non porous surface, chip, or any suitable support, etc. . . . ) to which the nucleic acid molecules can be immobilized. For example, the nucleic acid molecules can be immobilized on a porous surface such as a glass surface or a glass bead. Yet in other examples, the nucleic acid can be immobilized on a flow-through system such as a porous membrane or the like. Nucleic acid molecules determined to have the correct desired sequence can be selectively released or selectively copied.

If the nucleic acid molecules are located in different locations, e.g. in separate wells of a substrate, the nucleic acid molecules can be taken selectively from the wells identified as containing nucleic acid molecules with desirable sequences. For example, in the apparatus of Margulies et al., polony beads are located in individual wells of a fiber-optic slide. Physical extraction of the bead from the appropriate well of the apparatus permits the subsequent amplification or purification of the desirable nucleic acid molecules free of other contaminating nucleic acid molecules. Alternatively, if the nucleic acid molecules are attached to the beads using a selectively cleavable linker, cleavage of the linker (e.g., by increasing the pH in the well to cleave a base-labile linker) followed by extraction of the solvent in the well can be used to selectively isolate the nucleic acid molecules without physical manipulation of the bead. Likewise, if the method of Shendure et al. is used, physical extraction of the beads or of the portions of the gel containing the nucleic acid molecules of interest can be used to selectively isolate desired nucleic acid molecules.

Certain other methods of selective isolation involve the targeting of nucleic acid molecules without a requirement for physical manipulation of a solid support. Such methods can incorporate the use of an optical system to specifically target radiation to individual nucleic acid molecules. In some embodiments, destructive radiation can be selectively targeted against undesired nucleic acid molecules (e.g., using micromirror technology) to destroy or disable them, leaving a population enriched for desired nucleic acid molecules. This enriched population can then be released from solid support and/or amplified, e.g., by PCR.

Example of methods and systems for selectively isolating the desired product (e.g. nucleic acids of interest) can use a laser tweezer or optical tweezer. Laser tweezers have been used for approximately two decades in the fields of biotechnology, medicine and molecular biology to position and manipulate micrometer-sized and submicrometer-sized particles (A. Ashkin, Science, (210), pp 1081-1088, 1980). By focusing the laser beam on the desired location (e.g. bead, well etc. . . . ) comprising the desired nucleic acid molecule of interest, the desired vessel remain optically trapped while the undesired nucleic acid sequences are eluted. Once all of the undesirable materials are washed off, the optical tweezer can be tuned off allowing the release the desired nucleic acid molecules.

Another method to capture the desirable products is by ablating the undesirable nucleic acids. In some embodiments, a high power laser can be used to generate enough energy to disable, degrade, or destroy the nucleic acid molecules in areas where undesirable materials exist. The area where desirable nucleic acids exist does not receive any destructive energy, hence preserving its contents.

In some embodiments, error-containing nucleic acid constructs can be eliminated. According to some embodiments, the method comprises generating a nucleic acid having oligonucleotide tags at its 5' end and 3' end. For example, after assembly of the target sequences (e.g. full length nucleic acid constructs), the target sequences can be barcoded or alternatively, the target sequence can be assembled from a plurality of oligonucleotides designed such that the target sequence has a barcode at its 5' end and it 3' end. The tagged target sequence can be fragmented and sequenced using, for example, next-generation sequencing as provided herein. After identification of error-free target sequences, error-free target sequences can be recovered from directly from the next-generation sequencing plate. In some embodiments, error-containing nucleic acids can be eliminated using laser ablation or any suitable method capable of eliminating undesired nucleic acid sequences. The error-free nucleic acid sequences can be eluted from the sequencing plate. Eluted nucleic acid sequences can be amplified using primers that are specific to the target sequences.

In some embodiments, the target polynucleotides can be amplified after obtaining clonal populations. In some embodiments, the target polynucleotide may comprise universal (common to all oligonucleotides), semi-universal (common to at least a portion of the oligonucleotides) or individual or unique primer (specific to each oligonucleotide) binding sites on either the 5' end or the 3' end or both. As used herein, the term "universal" primer or primer binding site means that a sequence used to amplify the oligonucleotide is common to all oligonucleotides such that all such oligonucleotides can be amplified using a single set of universal primers. In other circumstances, an oligonucleotide contains a unique primer binding site. As used herein, the term "unique primer binding site" refers to a set of primer recognition sequences that selectively amplifies a subset of oligonucleotides. In yet other circumstances, a target nucleic acid molecule contains both universal and unique amplification sequences, which can optionally be used sequentially.

In some aspects of the invention, a binding tag capable of binding error-free nucleic acid molecules or a solid support comprising a binding tag can be added to the error-free nucleic acid sequences. For example, the binding tag, solid support comprising binding tag or solid support capable of binding nucleic acid can be added to locations of the sequencing plate or flow cells identified to include error-free nucleic acid sequences. In some embodiments, the binding tag has a sequence complementary to the target nucleic acid sequence. In some embodiments the binding tag is a double-stranded sequence designed for either hybridization or ligation capture of nucleic acid of interest.

In some embodiments, the solid support can be a bead. In some embodiments, the bead can be disposed onto a substrate. The beads can be disposed on the substrate in a number of ways. Beads, or particles, can be deposited on a surface of a substrate such as a well or flow cell and can be exposed to various reagents and conditions which permit detection of the tag or label. In some embodiments, the binding tags or beads can be deposited by inkjet at specific location of a sequencing plate.

In some embodiments, beads can be derivatized in-situ with binding tags that are complementary to the barcodes or the additional sequences appended to the nucleic acids to capture, and/or enrich, and/or amplify the target nucleic acids identified to have the correct nucleic acid sequences (e.g. error-free nucleic acid). Nucleic acids can be immobilized on the beads by hybridization, covalent attachment, magnetic attachment, affinity attachment and the like. Hybridization is usually performed under stringent conditions. In some embodiments, the binding tags can be universal or generic primers complementary to non-target sequences, for example all barcodes or to appended additional sequences. In some embodiments, each bead can have binding tags capable of binding sequences present both the 5' end and the 3' end of the target molecules. Upon binding the target molecules, a loop-like structure is produced. Yet in other embodiments, beads can have a binding tag capable of binding sequences present at the 3' end of the target molecule. Yet in other embodiments, beads can have a binding tag capable of binding sequences present at the 5' end of the target molecule.

Beads, such as magnetic or paramagnetic beads, can be added to the each well or arrayed on a solid support. For example, Solid Phase Reversible Immobilization (SPRI) beads from Beckman Coulter can be used. In some embodiments, the pool of constructs can be distributed to the individual wells containing the beads. Additional thermal cycling can be used to enhance capture specificity. Using standard magnetic capture, the solution can then be removed followed by subsequent washing of the conjugated beads Amplification of the desired construct clone can be done either on bead or after release of the captured clone. In some embodiments, the beads can be configured for either hybridization or ligation based capture using double-stranded sequences on the bead.

A variation of the bead-based process can involve a set of flow-sortable encoded beads. Bead-based methods can employ nucleic acid hybridization to a capture probe or attachment on the surface of distinct populations of capture beads. Such encoded beads can be used on a pool of constructs and then sorted into individual wells for downstream amplification, isolation and clean up. While the use of magnetic beads described above can be particularly useful, other methods to separate beads can be envisioned in some aspects of the invention. The capture beads may be labeled with a fluorescent moiety which would make the target-capture bead complex fluorescent. For example, the beads can be impregnated with a fluorophore thereby creating distinct populations of beads that can be sorted according to the fluorescence wavelength. The target capture bead complex may be separated by flow cytometry or fluorescence cell sorter. In other embodiments, the beads can vary is size, or in any suitable characteristics allowing the sorting of distinct population of beads. For example, using capture beads having distinct sizes would allow separation by filtering or other particle size separation techniques.

In some embodiments, the flow-sortable encoded beads can be used to isolate the nucleic acid constructs prior to or after post-synthesis release. Such process allows for sorting by construct size, customer etc.

Figure 11:
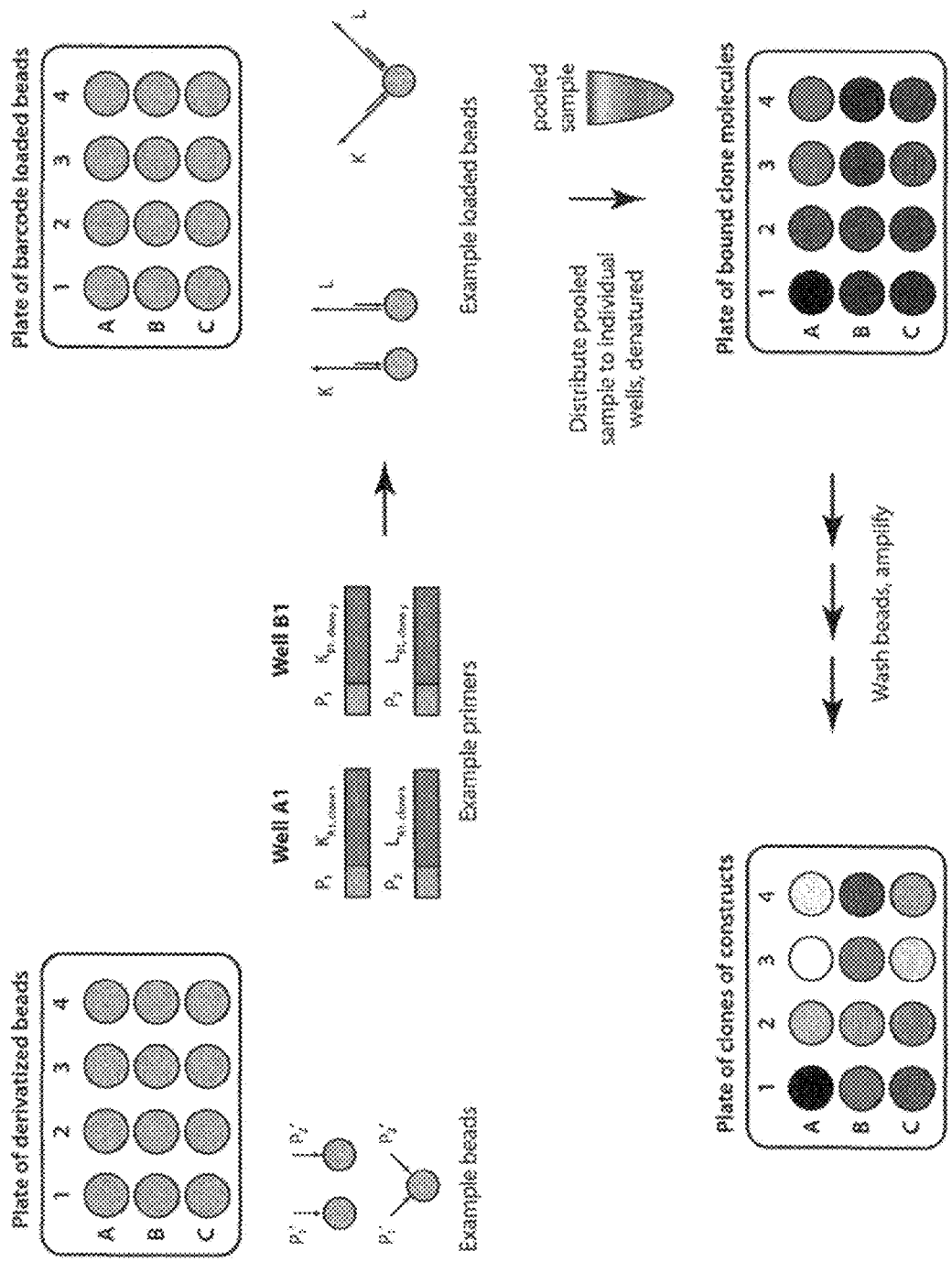
FIG. 11 illustrates a non-limiting exemplary embodiment of bead-based recovery process.

FIG. 11 schematically depicts a non-limiting exemplary bead-based recovery process. In some embodiments, primers can be loaded onto generic beads, for example, magnetic beads. Each bead can be derivatized many times to have many primers bound to it. In some embodiments, derivatization allows to have two or more different primers bound per bead, or to have the same primer bound per bead. Such beads can be distributed in each well of a multi-well plate. Beads can be loaded with barcodes capable of capturing specific nucleic acid molecules, for example by hybridizing a nucleic acid sequence comprising the barcode and a sequence complementary to the primer(s) loaded onto the generic beads. The sample comprising the double-stranded pooled nucleic acids can be subjected to appropriate conditions to render the double-stranded nucleic acids single-stranded. For example, the double-stranded nucleic acids can be subjected to any denaturation conditions known in the art. The pooled single-stranded sample can be distributed across all the wells of a multi-well plate. Under appropriate conditions, the derivatized beads comprising the barcodes can capture specific nucleic acid molecules in each well, based on the exact barcodes (K, L) loaded onto the beads in each well. The beads can then be washed. For example, when using magnetic beads, the beads can be pulled down with a magnet, allowing washing and removal of the solution. In some embodiments, the beads can be washed iteratively. The nucleic acids that remained bound on the beads can then amplified using PCR to produce individual clones in each well of the multi-well construct plate.

In other aspects of the invention, nanopore sequencing can be used to sequence individual nucleic acid strand at single nucleotide level. One of skill in the art would appreciate that nanopore sequencing has the advantage of minimal sample preparation, sequence readout that does not require nucleotides, polymerases or ligases, and the potential of very long read-lengths. However, nanopore sequencing can have relatively high error rates (~10% error per base). In some embodiments, the nanopore sequencing device comprises a shuntable microfluidic flow valve to recycle the full length nucleic acid construct so as to allow for multiple sequencing passes. In some embodiments, the nanopores can be connected in series with a shuntable microfluidic flow valve such that full length nucleic acid construct can be shunted back to the nanopore several times to allow for multiple sequencing passes. Using these configurations, the full length nucleic acid molecules can be sequenced two or more times. Resulting error-free nucleic acid sequences may be shunted to a collection well for recovery and use.

In some aspects of the invention, alternative preparative sequencing methods are provided herein. The methods comprise circularizing the target nucleic acid (e.g. the full length target nucleic acid) using double-ended primers capable of binding the 5' end and the 3' end of the target nucleic acids. In some embodiments, the double-ended primers have sequences complementary to the 5' end and the 3' end barcodes. Nucleases can be added so as to degrade the linear nucleic acid, thus locking-in the desired constructs. Optionally, the target nucleic acid can be amplified using primers specific to the target nucleic acids.

Inverted In Vitro Cloning

Figure 13A:
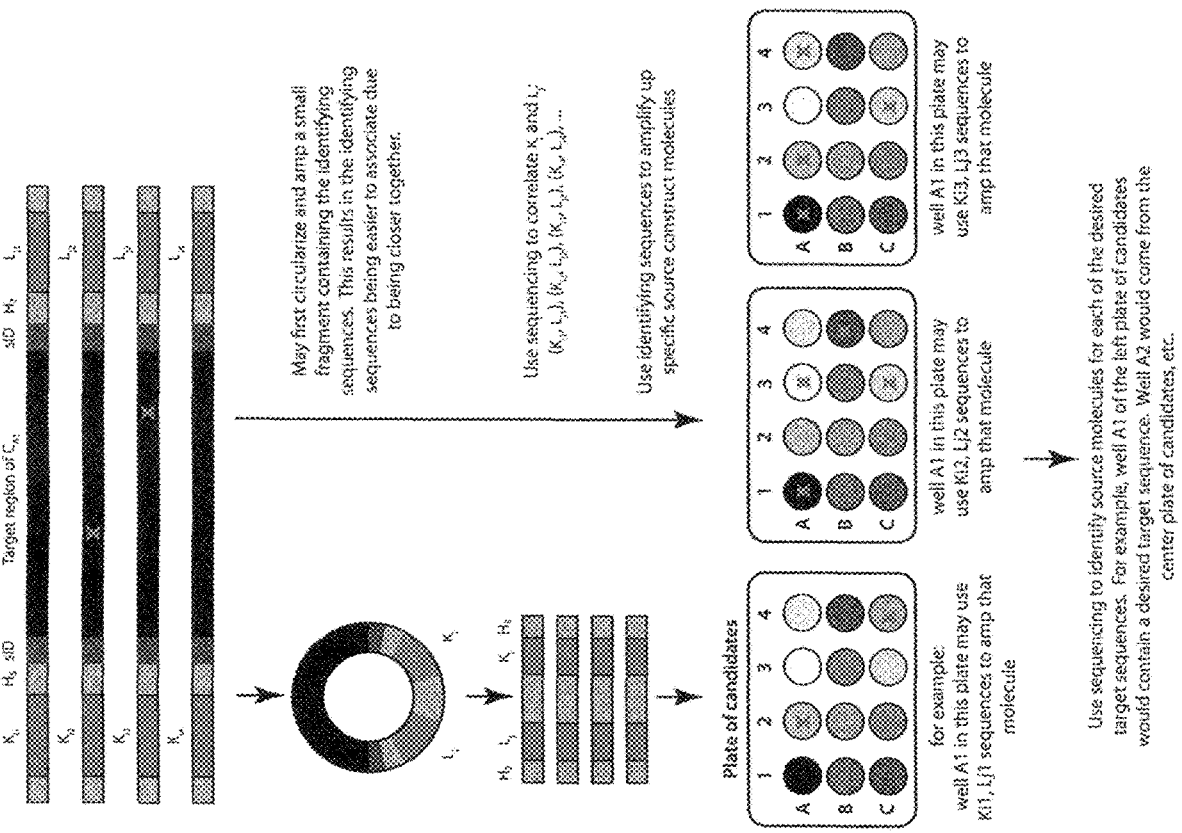
FIG. 13A illustrates a non-limiting example of inverted in vitro cloning.
Figure 13B:
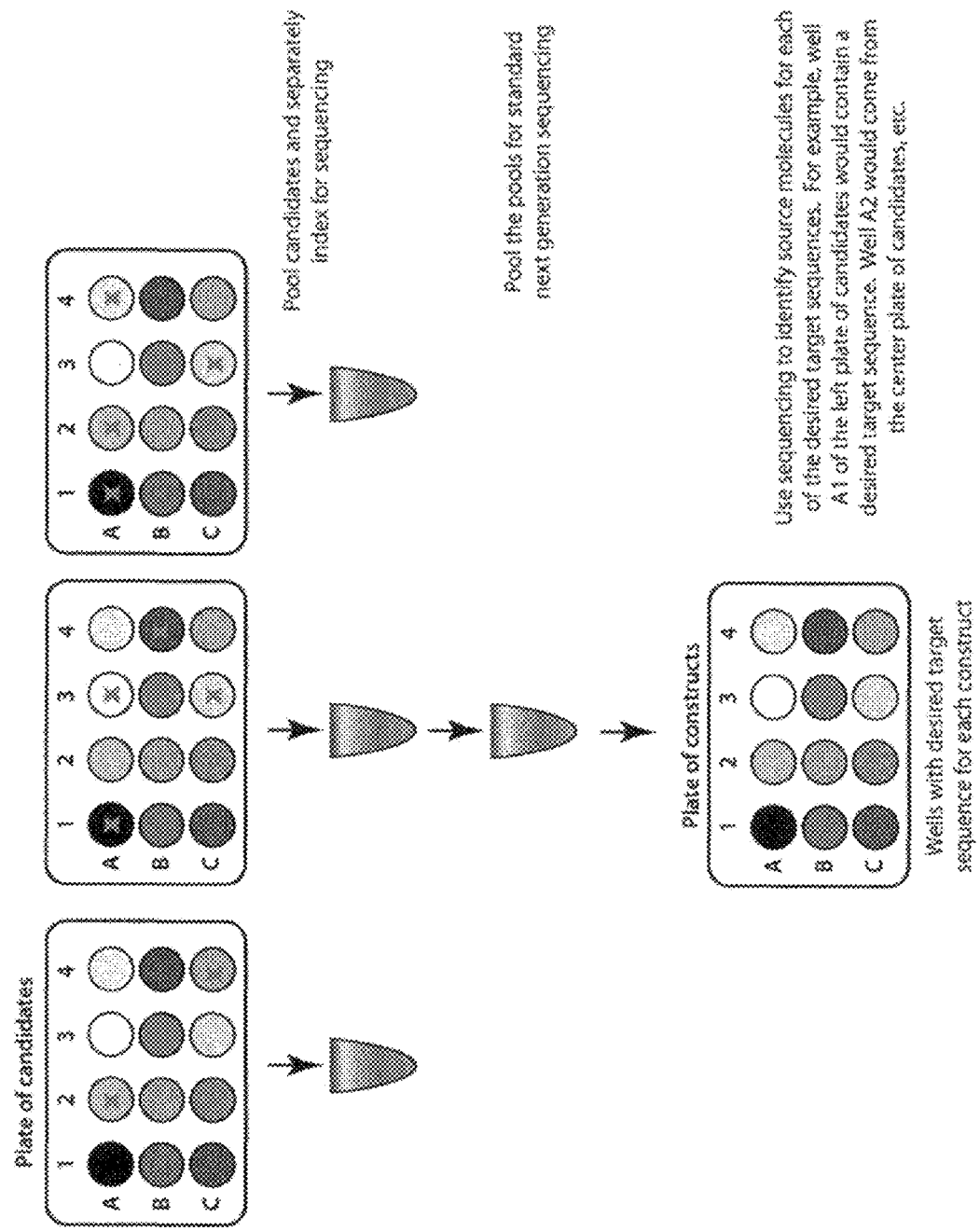
FIG. 13B illustrates a non-limiting example of inverted in vitro cloning.

In some aspects of the invention, methods are provided to isolate and/or recover a sequence-verified nucleic acid of interest. The methods described herein may be used to recover for example, error-free nucleic acid sequences of interest from a nucleic acid library or a pool of nucleic acid sequences. The nucleic acid library or the pool of nucleic acid sequences may include one or more target nucleic acid sequences of interest (e.g. N genes). In some embodiments, the library of nucleic acid sequences can include constructs assembled from oligonucleotides or nucleic acid fragments. A plurality of barcoded constructs can be assembled as described herein. In some embodiments, the plurality of constructs can be assembled and barcoded using a library of barcodes such that each nucleic acid construct can be tagged with a unique barcode at each end. Yet in other embodiments, the plurality of constructs can be assembled from a plurality of internal target sequence fragments and unique barcode sequences. For example, the library of nucleic acid sequences can comprise M copies of N different target nucleic acid sequences. For instance 100 copies of 96 target sequences, and the library of barcodes can have 316 different barcodes for a combinatories of 100,000. In some embodiments, the library of barcodes can have common amplification sequences (e.g. common primer binding sequences) on the outside of the barcodes. In some embodiments, if necessary, the pool of barcoded constructs can be amplified using the common amplification tags such as to have an appropriate concentration of nucleic acids for next generation sequencing. In some embodiments, the barcoded constructs can be subjected to sequencing reactions from both ends to obtain short paired end reads. In some embodiments, and as illustrated in FIG. 13A, the barcoded constructs of the pool of constructs can be circularized so as to get a barcode association which is independent of the length of the nucleic acid constructs. This way, a small nucleic acid fragment containing the identifying sequences such as barcodes $K_j$ and $L_j$ or oligonucleotide tags can be amplified. Identifying sequences are subjected to sequencing to correlate $K_i$, and $L_j$ ($K_{i1}$, $L_{j1}$), ($K_{i2}$, $L_{j2}$) etc. . . . For example, sequencing of the identifying sequences can result in C clones having the target sequence according to the identity of their corresponding unique pair of identifying sequences. The identifying sequences can then be used to amplify the C specific source construct molecules in separate wells of a microtiter plate as illustrated in FIG. 13A. For example, if C=8 clones, 8 plates of N target nucleic acid sequences (e.g. 96 genes) can be provided, each plate having a different index tag (FIG. 13B). Source molecules (C*N) can be digested using Nextera™ tagmentation and sequenced using MiSeq®, HiSeq® or higher throughput next generation sequencing platforms to identify the correct target sequences. Sequencing data can be used to identify the target nucleic acid sequence, and sort the sequence-verified nucleic acid of interest. For example, as illustrated in FIG. 13A, well A1 of the left plate of candidates would contain the sequence-verified nucleic acid of interest. The identified clone can then be recovered from the well identified to have the sequence-verified nucleic acid of interest.

Determination of Barcode Pair Information

In some embodiments, and as described herein, the barcode pairs can be defined by sequencing full length molecules. Sequencing from both ends gives the required pairing information. For the most effective determination of barcode pairs using full length sequencing method, multiple Nextera™ tagmentation reactions, where the amount of Nextera™ enzyme is varied. These individual reactions can be processed in parallel and sequenced using MiSeq® at the same time using separate indexes. The read information can then be combined and processed as a whole. Using such process design allows for the identification of error-free molecules that can be subsequently captured by amplification. However due to the length limitation of the MiSeq® sequencing (e.g. poor sequencing of nucleic acids longer than ~1000 bps), barcode pairing using this method can be inefficient for constructs greater than 1000 bps.

The barcode pair information, according to some embodiments, can be determined according to the methods described in FIG. 14. FIGS. 14A and 14B illustrate different methods allowing the barcoded ends of the molecules to be brought together by blunt end ligation of the constructs into circles. In both concepts, barcodes can be added to the constructs via PCR, using sequence H1 as priming sites. After dilution and amplification with H2 primers, the construct pools can be split into two parallel paths. One part can be amplified with H2 primers with the p5 and p7 sequences necessary for sequencing on the MiSeq®. The amplified constructs can be fragmented by Nextera™ based cleavage and subsequently sequenced using MiSeq®. The second path is focused on determining the barcode pairing information. Referring to FIG. 14A, the barcode pairs can be amplified and sequenced. Referring to FIG. 14B, the barcode pairs can be cut out of the circle by restriction digest and subsequently sequenced. Using the methods described herein, the end barcode pairs can be associated in a manner that is independent of the length of the construct being sequenced.

Figure 14A:
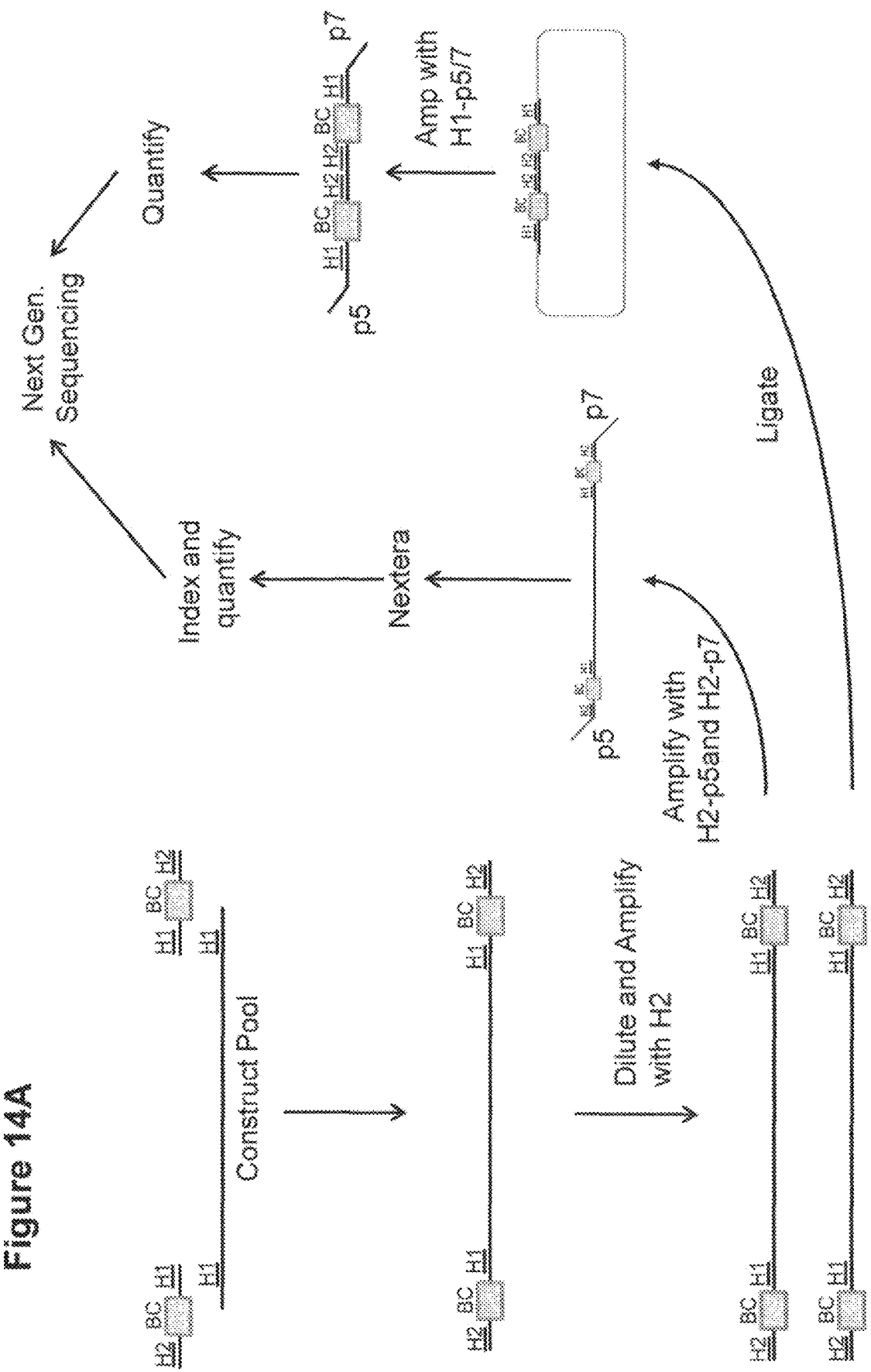
FIGS. 14A-C illustrate a method according to a non-limiting embodiment for determining barcode pair information.
Figure 14B:
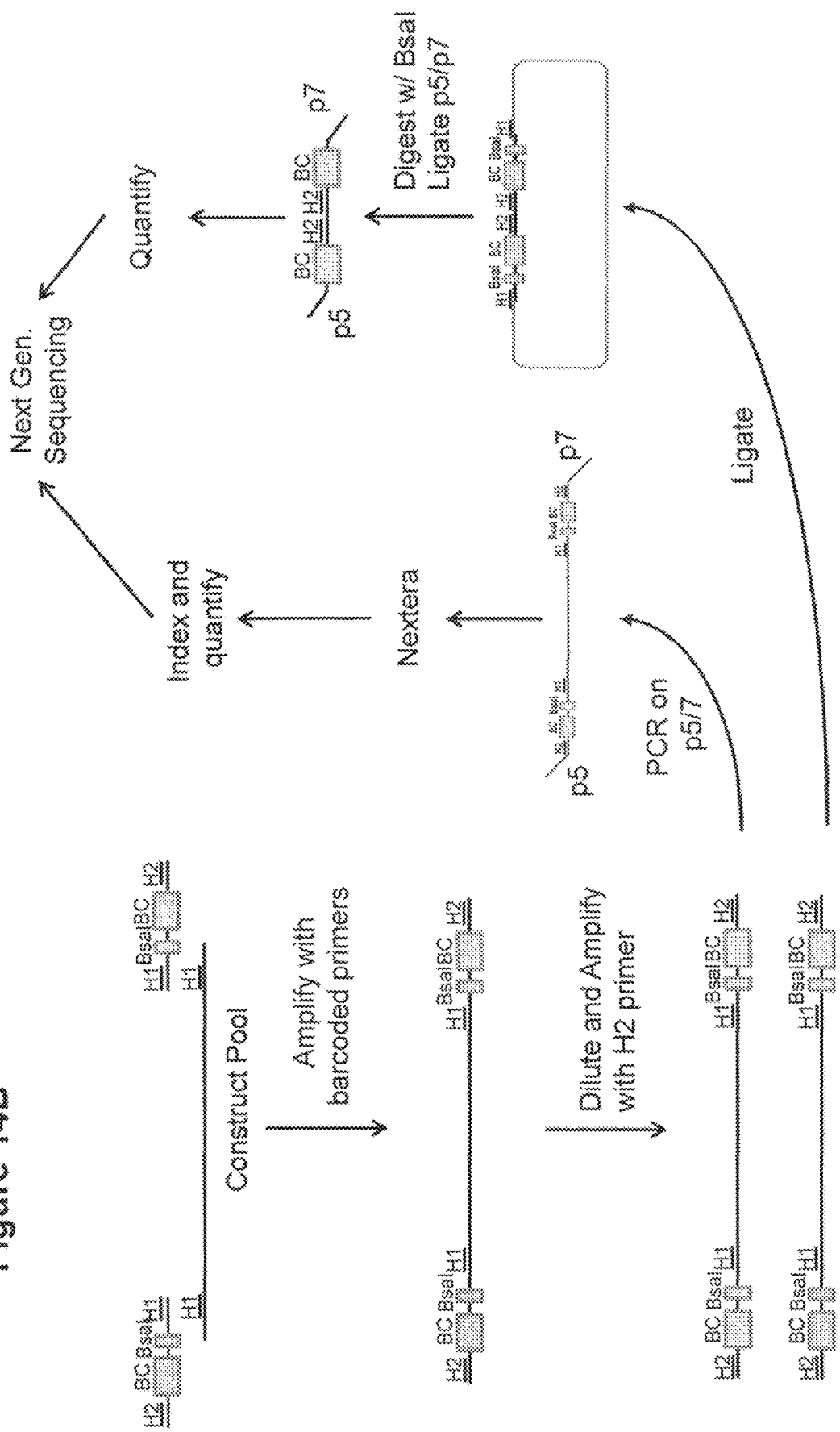
Figure 14C:
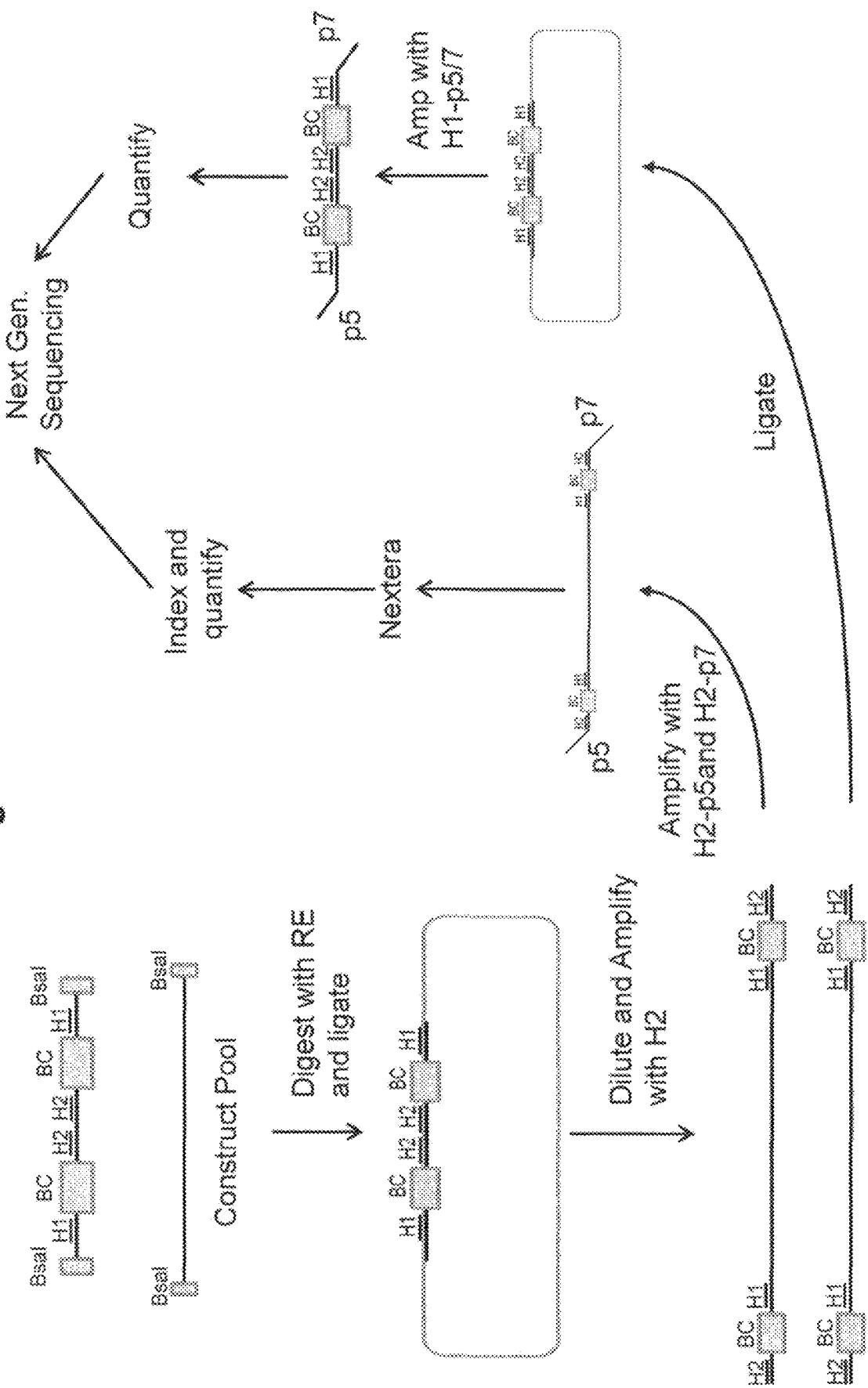
Figure 14D:
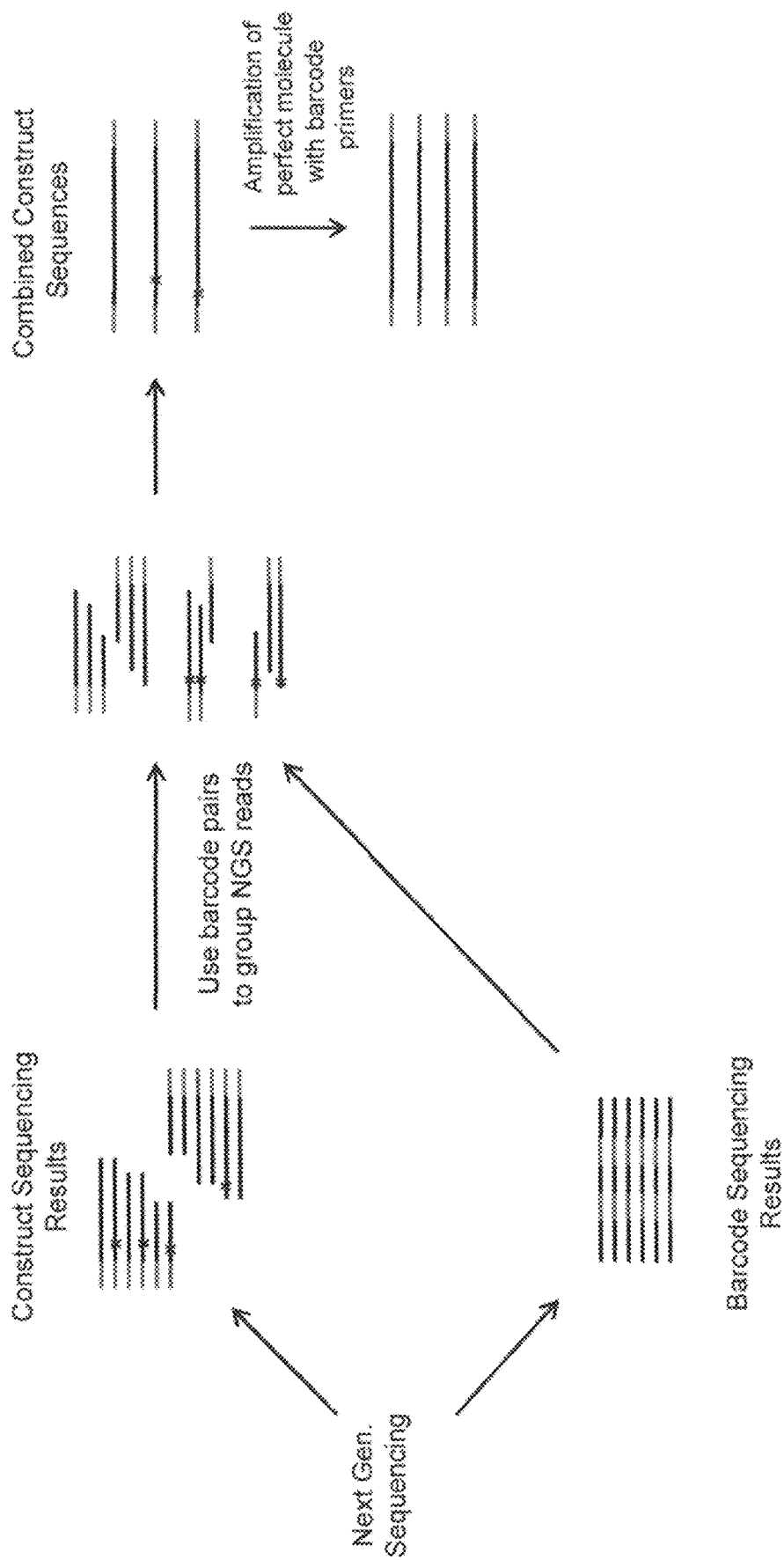
FIG. 14D illustrates how parallel sequencing of constructs and the isolated barcode pairs can be used to identify the correct molecule for subsequent capture by amplification. X in a sequence denotes an error in the molecule.

FIG. 14C illustrates a different method of attaching barcodes to the synthesized constructs. According to some embodiments, restriction enzymes, such as BsaI or any suitable restriction enzyme, can be used to open compatible nucleic acid overhangs which can then be used to ligate paired barcode molecules to the constructs, resulting in circular constructs. The pool of circular constructs can then diluted and amplified with primer H2. The constructs can then be processed as shown in either FIG. 14A or FIG. 14B. FIG. 14D shows a non-limiting embodiment using parallel sequencing of constructs and the isolated barcode pairs to identify the correct molecule for subsequent capture by amplification.

According to some embodiments, the barcode pairs can be generated as a pool of molecules, each with a single pair of barcodes. Referring to FIG. 15, these molecules can be circularized and diluted to an appropriate level, which can be defined by the appropriate total number of barcodes. For example, the number of barcodes can be $10^5$ or $10^6$. The diluted barcodes can then be amplified using multiple displacement amplification to generate multiple copies of each barcode. The resulting pool of barcodes can then split into two. A first portion can be used in barcoding synthesized constructs. The second portion can be sequenced using next generation sequencing. The sequencing data will give the barcode-barcode associations within the pool. With appropriate sequencing, the pool can be defined to completion. It should be appreciate that when sequencing the constructs using such pool, the barcode associations are already known, removing the need for processes outlined in FIG. 14.

Applications

Aspects of the invention may be useful for a range of applications involving the production and/or use of synthetic nucleic acids. As described herein, the invention provides methods for producing synthetic nucleic acids having the desired sequence with increased efficiency. The resulting nucleic acids may be amplified in vitro (e.g., using PCR, LCR, or any suitable amplification technique), amplified in vivo (e.g., via cloning into a suitable vector), isolated and/or purified. An assembled nucleic acid (alone or cloned into a vector) may be transformed into a host cell (e.g., a prokaryotic, eukaryotic, insect, mammalian, or other host cell). In some embodiments, the host cell may be used to propagate the nucleic acid. In certain embodiments, the nucleic acid may be integrated into the genome of the host cell. In some embodiments, the nucleic acid may replace a corresponding nucleic acid region on the genome of the cell (e.g., via homologous recombination). Accordingly, nucleic acids may be used to produce recombinant organisms. In some embodiments, a target nucleic acid may be an entire genome or large fragments of a genome that are used to replace all or part of the genome of a host organism. Recombinant organisms also may be used for a variety of research, industrial, agricultural, and/or medical applications.

Many of the techniques described herein can be used together, applying suitable assembly techniques at one or more points to produce long nucleic acid molecules. For example, ligase-based assembly may be used to assemble oligonucleotide duplexes and nucleic acid fragments of less than 100 to more than 10,000 base pairs in length (e.g., 100 mers to 500 mers, 500 mers to 1,000 mers, 1,000 mers to 5,000 mers, 5,000 mers to 10,000 mers, 25,000 mers, 50,000 mers, 75,000 mers, 100,000 mers, etc.). In an exemplary embodiment, methods described herein may be used during the assembly of an entire genome (or a large fragment thereof e.g., about 10%, 20%, 30%, 40%, 50%, 60%, 70%, 80%, 90%, or more) of an organism (e.g., of a viral, bacterial, yeast, or other prokaryotic or eukaryotic organism), optionally incorporating specific modifications into the sequence at one or more desired locations.

Any of the nucleic acid products (e.g., including nucleic acids that are amplified, cloned, purified, isolated, etc.) may be packaged in any suitable format (e.g., in a stable buffer, lyophilized, etc.) for storage and/or shipping (e.g., for shipping to a distribution center or to a customer). Similarly, any of the host cells (e.g., cells transformed with a vector or having a modified genome) may be prepared in a suitable buffer for storage and or transport (e.g., for distribution to a customer). In some embodiments, cells may be frozen. However, other stable cell preparations also may be used.

Host cells may be grown and expanded in culture. Host cells may be used for expressing one or more RNAs or polypeptides of interest (e.g., therapeutic, industrial, agricultural, and/or medical proteins). The expressed polypeptides may be natural polypeptides or non-natural polypeptides. The polypeptides may be isolated or purified for subsequent use.

Accordingly, nucleic acid molecules generated using methods of the invention can be incorporated into a vector. The vector may be a cloning vector or an expression vector. In some embodiments, the vector may be a viral vector. A viral vector may comprise nucleic acid sequences capable of infecting target cells. Similarly, in some embodiments, a prokaryotic expression vector operably linked to an appropriate promoter system can be used to transform target cells. In other embodiments, a eukaryotic vector operably linked to an appropriate promoter system can be used to transfect target cells or tissues.

Transcription and/or translation of the constructs described herein may be carried out in vitro (i.e. using cell-free systems) or in vivo (i.e. expressed in cells). In some embodiments, cell lysates may be prepared. In certain embodiments, expressed RNAs or polypeptides may be isolated or purified. Nucleic acids of the invention also may be used to add detection and/or purification tags to expressed polypeptides or fragments thereof. Examples of polypeptide-based fusion/tag include, but are not limited to, hexa-histidine ($His^6$) Myc and HA, and other polypeptides with utility, such as $GFP_5$ GST, MBP, chitin and the like. In some embodiments, polypeptides may comprise one or more unnatural amino acid residue(s).

In some embodiments, antibodies can be made against polypeptides or fragment(s) thereof encoded by one or more synthetic nucleic acids. In certain embodiments, synthetic nucleic acids may be provided as libraries for screening in research and development (e.g., to identify potential therapeutic proteins or peptides, to identify potential protein targets for drug development, etc.) In some embodiments, a synthetic nucleic acid may be used as a therapeutic (e.g., for gene therapy, or for gene regulation). For example, a synthetic nucleic acid may be administered to a patient in an amount sufficient to express a therapeutic amount of a protein. In other embodiments, a synthetic nucleic acid may be administered to a patient in an amount sufficient to regulate (e.g., down-regulate) the expression of a gene.

It should be appreciated that different acts or embodiments described herein may be performed independently and may be performed at different locations in the United States or outside the United States. For example, each of the acts of receiving an order for a target nucleic acid, analyzing a target nucleic acid sequence, designing one or more starting nucleic acids (e.g., oligonucleotides), synthesizing starting nucleic acid(s), purifying starting nucleic acid(s), assembling starting nucleic acid(s), isolating assembled nucleic acid(s), confirming the sequence of assembled nucleic acid(s), manipulating assembled nucleic acid(s) (e.g., amplifying, cloning, inserting into a host genome, etc.), and any other acts or any parts of these acts may be performed independently either at one location or at different sites within the United States or outside the United States. In some embodiments, an assembly procedure may involve a combination of acts that are performed at one site (in the United States or outside the United States) and acts that are performed at one or more remote sites (within the United States or outside the United States).

Automated Applications

Aspects of the methods and devices provided herein may include automating one or more acts described herein. In some embodiments, one or more steps of an amplification and/or assembly reaction may be automated using one or more automated sample handling devices (e.g., one or more automated liquid or fluid handling devices). Automated devices and procedures may be used to deliver reaction reagents, including one or more of the following: starting nucleic acids, buffers, enzymes (e.g., one or more ligases and/or polymerases), nucleotides, salts, and any other suitable agents such as stabilizing agents. Automated devices and procedures also may be used to control the reaction conditions. For example, an automated thermal cycler may be used to control reaction temperatures and any temperature cycles that may be used. In some embodiments, a scanning laser may be automated to provide one or more reaction temperatures or temperature cycles suitable for incubating polynucleotides. Similarly, subsequent analysis of assembled polynucleotide products may be automated. For example, sequencing may be automated using a sequencing device and automated sequencing protocols. Additional steps (e.g., amplification, cloning, etc.) also may be automated using one or more appropriate devices and related protocols. It should be appreciated that one or more of the device or device components described herein may be combined in a system (e.g., a robotic system) or in a micro-environment (e.g., a micro-fluidic reaction chamber). Assembly reaction mixtures (e.g., liquid reaction samples) may be transferred from one component of the system to another using automated devices and procedures (e.g., robotic manipulation and/or transfer of samples and/or sample containers, including automated pipetting devices, micro-systems, etc.). The system and any components thereof may be controlled by a control system.

Accordingly, method steps and/or aspects of the devices provided herein may be automated using, for example, a computer system (e.g., a computer controlled system). A computer system on which aspects of the technology provided herein can be implemented may include a computer for any type of processing (e.g., sequence analysis and/or automated device control as described herein). However, it should be appreciated that certain processing steps may be provided by one or more of the automated devices that are part of the assembly system. In some embodiments, a computer system may include two or more computers. For example, one computer may be coupled, via a network, to a second computer. One computer may perform sequence analysis. The second computer may control one or more of the automated synthesis and assembly devices in the system. In other aspects, additional computers may be included in the network to control one or more of the analysis or processing acts. Each computer may include a memory and processor. The computers can take any form, as the aspects of the technology provided herein are not limited to being implemented on any particular computer platform. Similarly, the network can take any form, including a private network or a public network (e.g., the Internet). Display devices can be associated with one or more of the devices and computers. Alternatively, or in addition, a display device may be located at a remote site and connected for displaying the output of an analysis in accordance with the technology provided herein. Connections between the different components of the system may be via wire, optical fiber, wireless transmission, satellite transmission, any other suitable transmission, or any combination of two or more of the above.

Each of the different aspects, embodiments, or acts of the technology provided herein can be independently automated and implemented in any of numerous ways. For example, each aspect, embodiment, or act can be independently implemented using hardware, software or a combination thereof. When implemented in software, the software code can be executed on any suitable processor or collection of processors, whether provided in a single computer or distributed among multiple computers. It should be appreciated that any component or collection of components that perform the functions described above can be generically considered as one or more controllers that control the above-discussed functions. The one or more controllers can be implemented in numerous ways, such as with dedicated hardware, or with general purpose hardware (e.g., one or more processors) that is programmed using microcode or software to perform the functions recited above.

In this respect, it should be appreciated that one implementation of the embodiments of the technology provided herein comprises at least one computer-readable medium (e.g., a computer memory, a floppy disk, a compact disk, a tape, etc.) encoded with a computer program (i.e., a plurality of instructions), which, when executed on a processor, performs one or more of the above-discussed functions of the technology provided herein. The computer-readable medium can be transportable such that the program stored thereon can be loaded onto any computer system resource to implement one or more functions of the technology provided herein. In addition, it should be appreciated that the reference to a computer program which, when executed, performs the above-discussed functions, is not limited to an application program running on a host computer. Rather, the term computer program is used herein in a generic sense to reference any type of computer code (e.g., software or microcode) that can be employed to program a processor to implement the above-discussed aspects of the technology provided herein.

It should be appreciated that in accordance with several embodiments of the technology provided herein wherein processes are stored in a computer readable medium, the computer implemented processes may, during the course of their execution, receive input manually (e.g., from a user).

Accordingly, overall system-level control of the assembly devices or components described herein may be performed by a system controller which may provide control signals to the associated nucleic acid synthesizers, liquid handling devices, thermal cyclers, sequencing devices, associated robotic components, as well as other suitable systems for performing the desired input/output or other control functions. Thus, the system controller along with any device controllers together form a controller that controls the operation of a nucleic acid assembly system. The controller may include a general purpose data processing system, which can be a general purpose computer, or network of general purpose computers, and other associated devices, including communications devices, modems, and/or other circuitry or components to perform the desired input/output or other functions. The controller can also be implemented, at least in part, as a single special purpose integrated circuit (e.g., ASIC) or an array of ASICs, each having a main or central processor section for overall, system-level control, and separate sections dedicated to performing various different specific computations; functions and other processes under the control of the central processor section. The controller can also be implemented using a plurality of separate dedicated programmable integrated or other electronic circuits or devices, e.g., hard wired electronic or logic circuits such as discrete element circuits or programmable logic devices. The controller can also include any other components or devices, such as user input/output devices (monitors, displays, printers, a keyboard, a user pointing device, touch screen, or other user interface, etc.), data storage devices, drive motors, linkages, valve controllers, robotic devices, vacuum and other pumps, pressure sensors, detectors, power supplies, pulse sources, communication devices or other electronic circuitry or components, and so on. The controller also may control operation of other portions of a system, such as automated client order processing, quality control, packaging, shipping, billing, etc., to perform other suitable functions known in the art but not described in detail herein.

Various aspects of the present invention may be used alone, in combination, or in a variety of arrangements not specifically discussed in the embodiments described in the foregoing and is therefore not limited in its application to the details and arrangement of components set forth in the foregoing description or illustrated in the drawings. For example, aspects described in one embodiment may be combined in any manner with aspects described in other embodiments.

Use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

The following examples are set forth as being representative of the present invention. These examples are not to be construed as limiting the scope of the invention as these and other equivalent embodiments will be apparent in view of the present disclosure, figures and accompanying claims.

EXAMPLES

Example 1

The methods described herein and illustrated in FIG. 1A-C allow for the identification of target nucleic acids having the correct desired sequence from a plate of having a plurality of distinct nucleic acid constructs, each plurality of nucleic acid constructs comprising a mixture of correct and incorrect sequences.

In step I, FIG. 1A, a plurality of constructs ($C_{A1}$-$C_{An}$, . . . , $C_{N1}$-$C_{Nn}$) is provided within separate wells of a microplate, each well comprising a mixture of correct and incorrect sequence sites. Each construct can have a target region flanked at the 5' end with a construct specific region X and a common region or adaptor A and at the 3' end a construct specific region Y and a common region or adaptor B.

In step II, FIG. 1A, each of the construct mixture can be diluted to a limited number of molecules (about 100-1000) such as each well of the plate comprise normalized mixture of molecules. Each of the dilutions can be mixed and pooled together into one tube.

In step III, FIG. 1A, the plurality of molecules is tagged with pairs of primers (P1, P2) and a large library of nucleotide tags or barcodes (K,L) by ligation or polymerase chain reaction. The methods described herein allow for each molecule to be tagged with a unique pair of barcodes (K, L) to distinguish the molecule from the other molecules in the pool. For example, each well can comprise about 100 molecules and each molecule can be tagged with a unique K-L tag (e.g. $K_1$-$L_1$; $K_j$-$L_j$, ... $K_{100}$-$L_{100}$). The entire sample can be amplified to generate enough material for sequencing and the preparative recovery.

In step IV, FIG. 1B, the sample is then split, with the bulk of the sample undergoing Nextera™ tagmentation. The tagmentation reaction can be optimized to make under two breakages per molecule, ensuring that the bulk of the molecules contain one of the tag barcodes and a partial length of the construct target region. The reserved portion of the sample that did not undergo tagmentation, is mixed back in and prepped for sequencing. Two example molecules with one break are shown, each splitting two to sequencing fragments with a tag from the 5' or 3' end. For example, as illustrated in FIG. 1B, molecule b can be splitted in two to generate b1 and b2.

In step V, FIG. 1B, the full length molecules generate paired reads which map the tag pairs (Kj, Lj) to individual clonal construct molecules (for example construct $C_1$, clone j in well 1). The Nextera™ tagmented paired reads generate one sequence with a tag for identification, and another sequence internal to the construct target region. With high throughput sequencing, enough coverage can be generated to reconstruct the consensus sequence of each tag pair construct and determine if the sequence is correct. For example, as illustrated in FIG. 1B, each fragment in sequencing generates two reads (a paired read). Molecule "a" generates reads with associate a unique barcode $K_{A1-x}$ with a unique barcode $L_{A1-x}$. No other molecule should have the same combination. If two molecules from the same construct have a common barcode, the data is discarded due to the ambiguity of the source molecule for those reads. Fragments b1, b2, c1, c2 etc. are identified by one read of the paired read with the barcode. The other read is used to make consensus sequence of internal regions of the molecule. The consensus sequence from each clone is compared with the desired sequence. The example shows results from well A1 in which clone x is correct, but clone y and z are incorrect. Similar results for each of the original constructs pooled together can be obtained in parallel from the sequencing results.

In step VI, FIG. 1C, the correct construct sequences is amplified using a pair of primers in each well which have the unique tag sequences from the tag pair corresponding to the correct nucleic acid clone. Each clone can be amplified with the tagged pool as a template in individual wells. This allows for the generation of a plate of cloned constructs, each well containing a different desired sequence with each molecule having the correct sequence. As illustrated in FIG. 1C, the molecules in each well are in vitro clones of the original constructs, with flanking sequences corresponding to the barcode combination (K,L) used to amplify the clones having the correct predetermined sequence.

Example 2

Figure 7A:
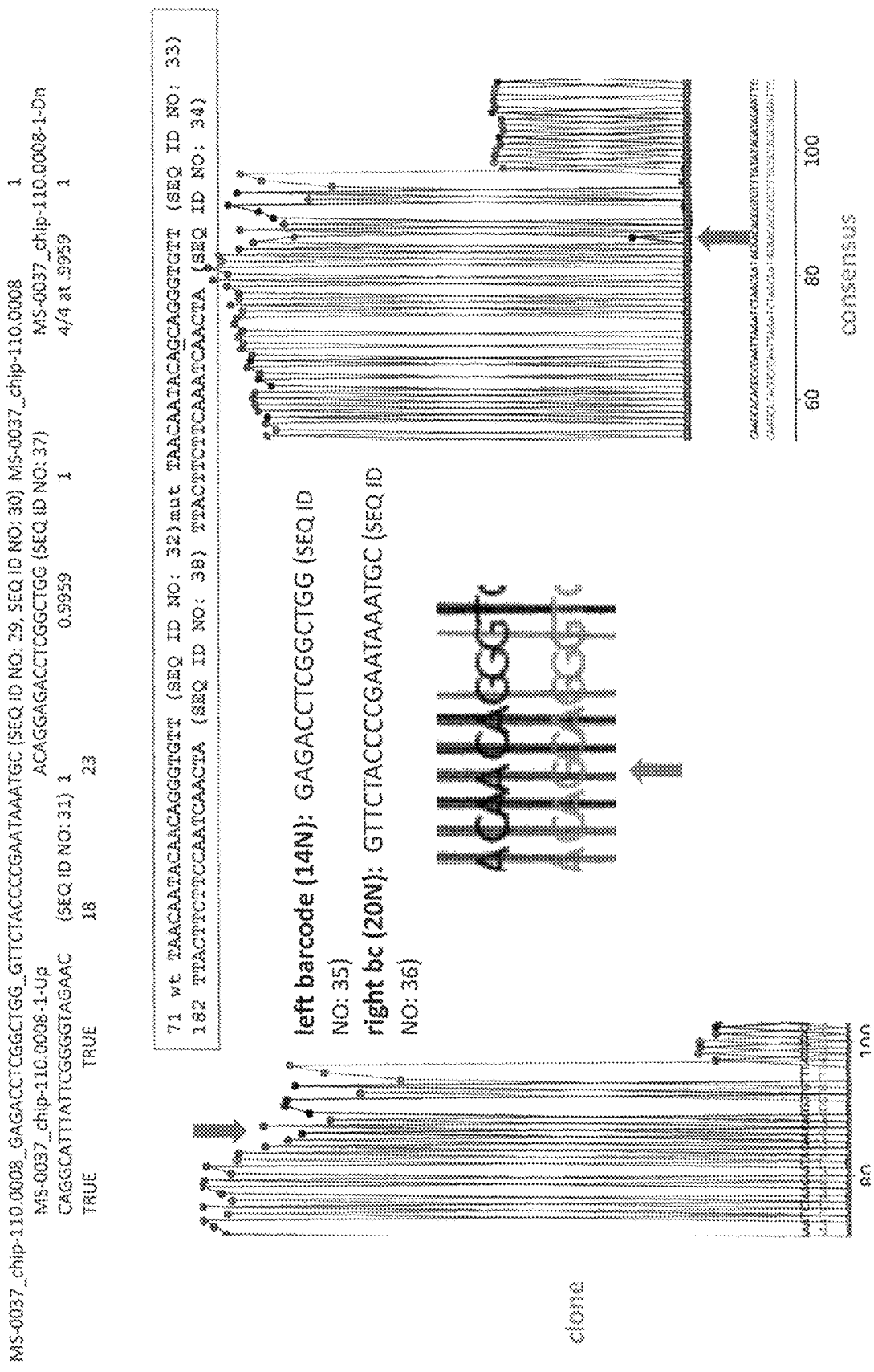
FIG. 7A illustrates non-limiting embodiments of the separation of source molecules.
Figure 7B:
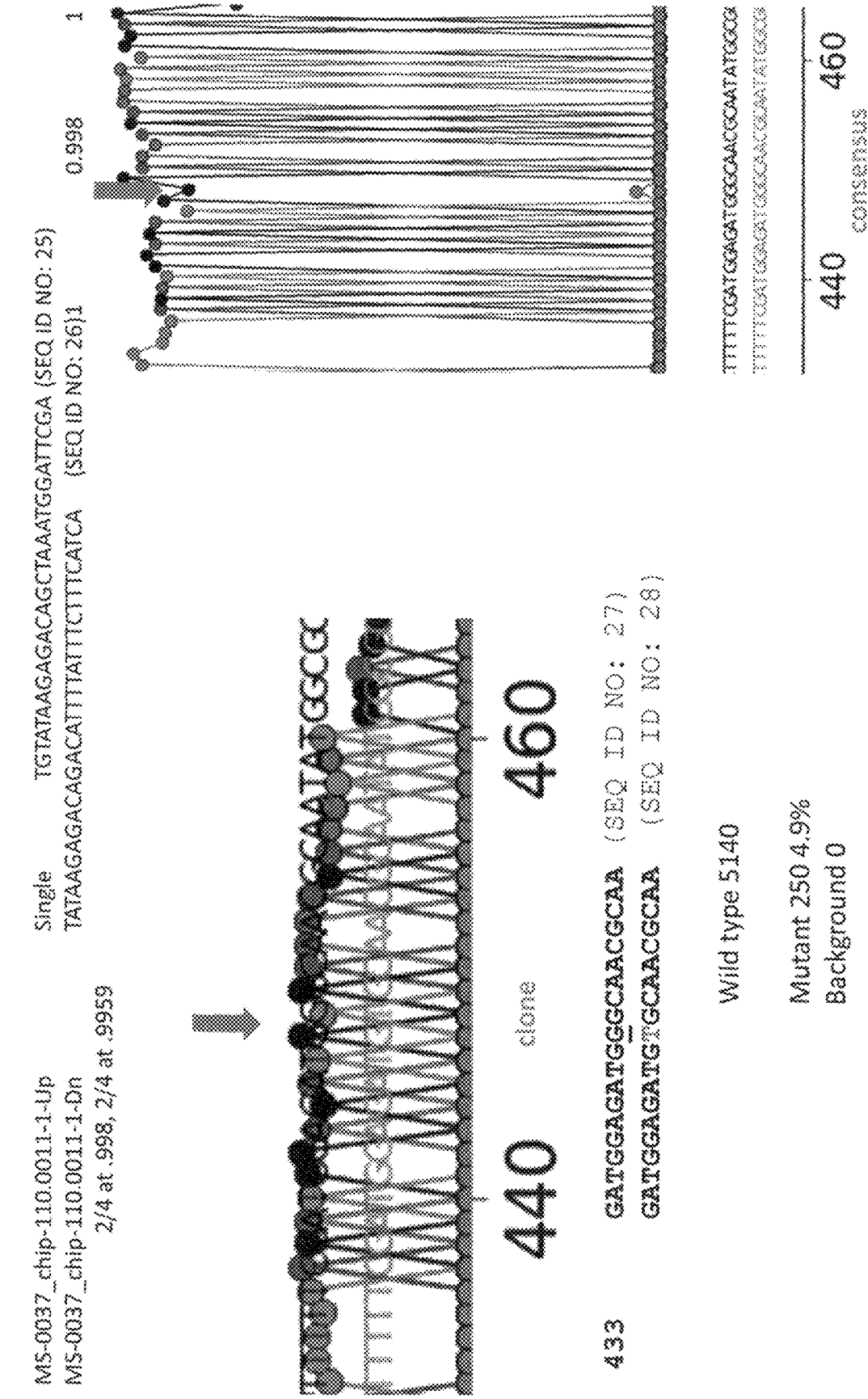
FIG. 7B illustrates non-limiting embodiments of the separation of source molecules.

The foregoing methods of in vitro cloning can be extremely effective at distinguishing individual source molecules. A consensus sequence (from all the source molecules of one construct) can have small competing signals from individual source molecules with errors at a position. In some embodiments, the consensus sequence can be compared with the trace from that individual source molecule with the error. In most of the cases, the source molecule can be cleanly called as an error, with no competing signal from the (large) background of the correct base. FIGS. 7A and 7B illustrate an example of effective source molecule separation. On the right side is a consensus trace of all reads of a particular construct at a certain location. As illustrated in FIGS. 7A-B, where there is a "mutation" or "error" signal, quite small relative to the whole population, that mutation/error stems from a single clone (source molecule). On the left side is a consensus trace of all reads of the same construct but from a particular barcode pair (i.e. clone). The same position is shown, which contains only the "mutation" signal and no signal from the wild-type/reference background. Thus the two signals are completely separable and correspond to individual source molecules which are distinguished.

Example 3

Figure 8:
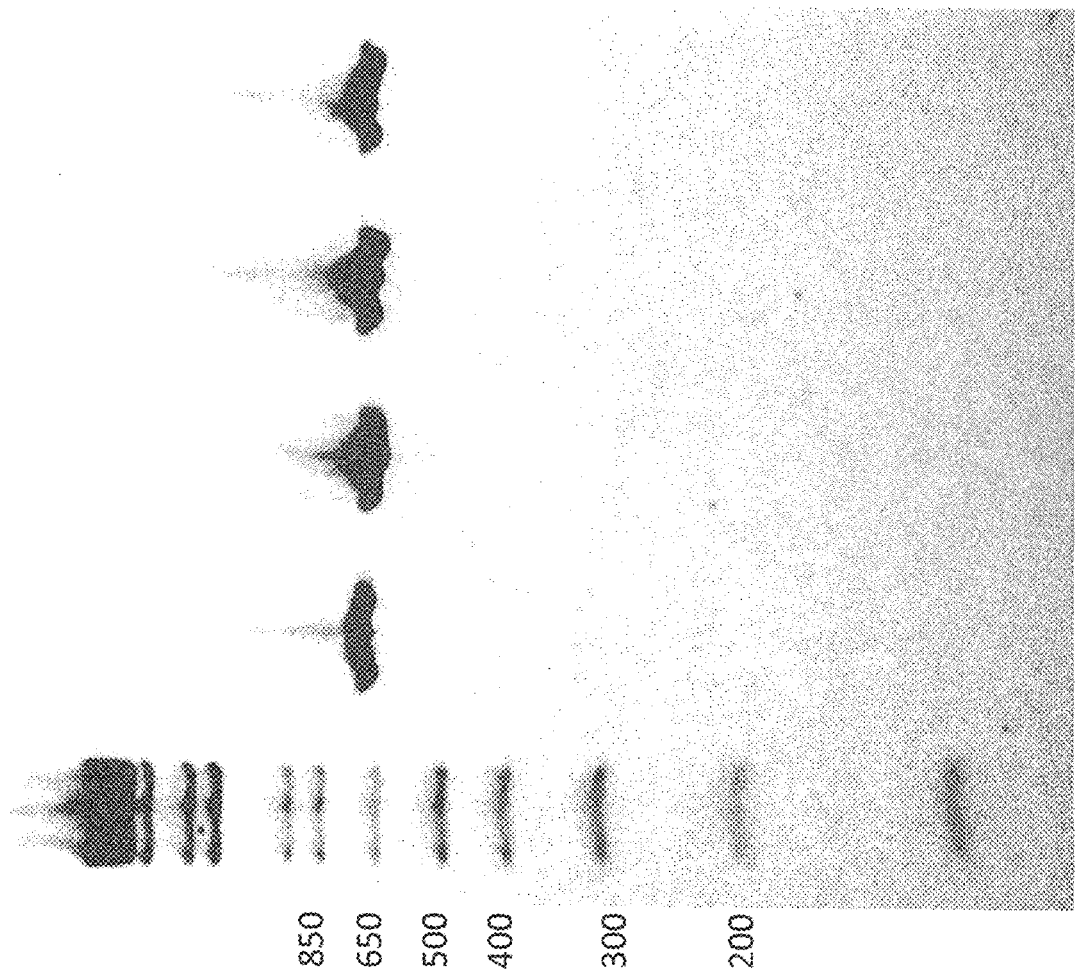
FIG. 8 illustrates a non-limiting exemplary isolation of target nucleic acids using degenerate barcodes.

FIG. 8 illustrates the use of coded barcodes to isolate or fish out nucleic acids having the predetermined sequences. In an exemplary embodiment, the 5' barcode is 14N and the 3' barcode is 20N. Primers (also referred herein as fish-out primers) were used for isolation of targets (chip-110.0001) as illustrated in FIG. 8. Each barcode pair (left barcode is in bold as illustrated below) was used to make primers. Clone A uses primer sequences 1 & 2; clone B uses 3 & 4, etc. . . . . The target molecule was recovered very cleanly using PCR with the fish-out primers.

```
chip-110.0001_
                       (SEQ ID NO: 1, SEQ ID NO: 2)
ACTCACCTCGTTTC_CCTTATAAGCATGTCTCATA 1
                                      (SEQ ID NO: 3)
AGAGACAGACTCACCTCGTTTC 2
                                      (SEQ ID NO: 4)
GAGACAGTATGAGACATGCTTATAAGG chip-110.0001_
                       (SEQ ID No. 5, SEQ ID NO: 6)
GCCGCCGCTGGGGC_CCTCCCCACGCTCTCTAGCC 3
                                      (SEQ ID NO: 7)
GGCCGCCGCTGGGGC 4
                                      (SEQ ID NO: 8)
ACAGGGCTAGAGAGCGTGGGGAGG chip-110.0001_
                      ((SEQ ID NO: 9, SEQ ID NO: 10)
GGAGCGATCACCAT_TAGACGTTCATGGTACATAC 5
                                      (SEQ ID NO: 11)
ACAGGGAGCGATCACCAT 6
                                      (SEQ ID NO: 12)
ACAGGTATGTACCATGAACGTCTA
```

-continued chip-110.0001_
(SEQ ID NO: 13, SEQ ID NO: 14)
CGGAGTGCTGGGAT_CCTTTGTGGTCATGAGTTTG 7
(SEQ ID NO: 15)
AGCGGAGTGCTGGGAT

8
(SEQ ID NO: 16)
AGCAAACTCATGACCACAAAGG

Figure 9:
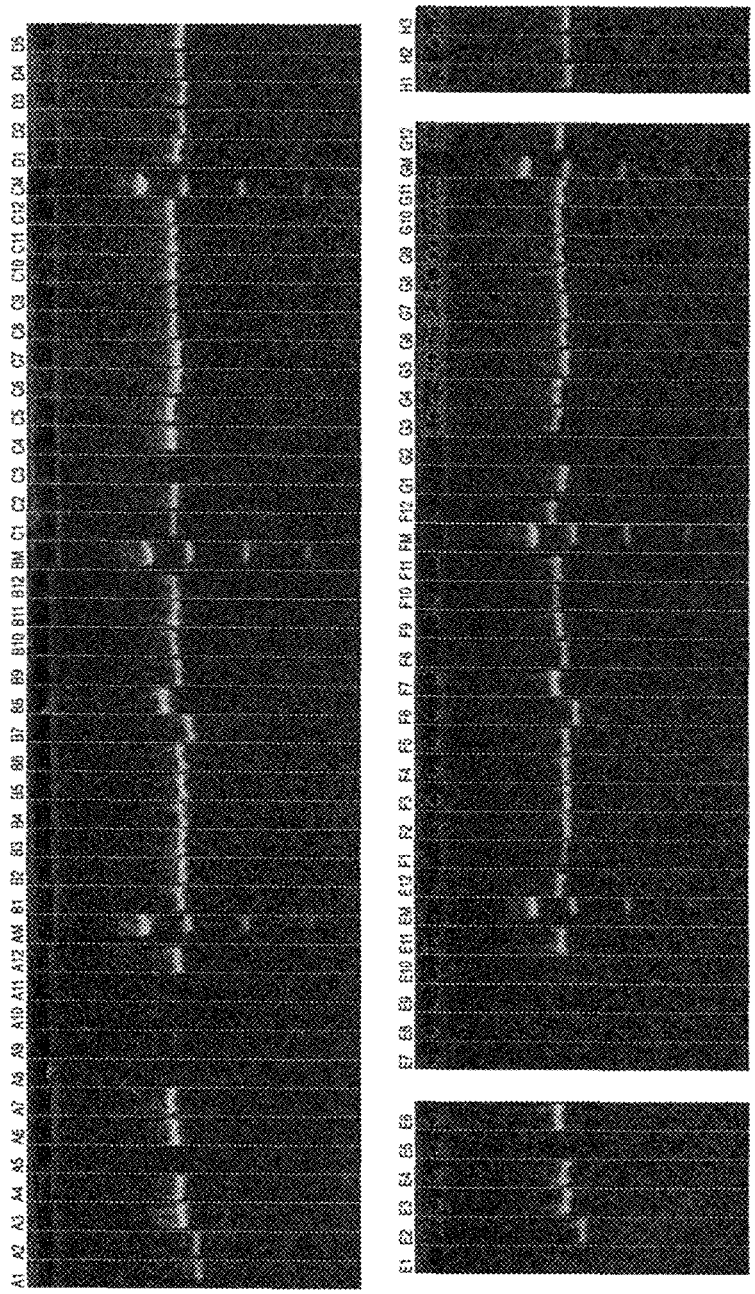
FIG. 9 illustrates a non-limiting exemplary isolation of nucleic acid clones from a pool of constructs using barcodes.

As illustrated in FIG. 9, 54 constructs ranging in size from about 650 to about 1100 bps were normalized and pooled together. The barcodes were attached by polymerase chain reaction using the handle sequences on each construct (5': CATCAACGTTCATGTCGCGC (SEQ ID NO: 17), 3': CCTTGGGTGCTCGCAGTAAA (SEQ ID NO: 18)). The barcoded primers were composed of a common region for Illumina sequencing preparation, a degenerate portion for the barcode, and the handle sequences shown above. The degenerate portion of the 5' barcode was designed to have 14N and the degenerate portion of the 3' barcode was designed to have a 20N. The 5' barcodes primer was composed of the following sequences: TCGTCGGCAGCGTC (SEQ ID NO: 19) AGATGTGTATAAGAGACAG (SEQ ID NO: 20) NNNNNNNNNNNNNN CATCAACGTTCATGTCGCGC (SEQ ID NO: 17). The 3' barcoded primer was composed of the following sequences: GTCTCGTGGGCTCGG (SEQ ID NO: 21) AGATGTGTATAAGAGACAG (SEQ ID NO: 22) NNNNNNNNNNNNNNNNNN CCTTGGGTGCTCG-CAOTAAA (SEQ ID No. 18).

Polymerase chain reaction (PCR) was carried out using KOD polymerase for 5 cycles. The resulting mixture was purified using SPRI beads to remove short products and primers. The pooled sample was then diluted to a factor of 512,000 fold using 8 fold dilutions of a 1000× fold initial dilution. The pooled sample was used as a template in a PCR reaction, using KOD polymerase and using primers corresponding to the 5' common region of the primers for the previous PCR. After 30 cycles, the sample was again purified using SPRI beads to remove short products, primers, and protein. The sample at this stage is called the "fish-out template".

The Nextera™ tagmentation reaction was performed as prescribed in the Illumina manual, but with increased input DNA amount (150 ng). The tagmentation reaction was cleaned with a Zymo purification kit (as recommended in the Illumina manual). The sample was then indexed, also according to the Illumina manual, and SPRI cleaned again.

The resulting DNA library was quantified by qPCR using the KAPA Sybr® Library quantification kit (Kapa Biosystems), as described in its manual. The resulting standard curve and titration curves were used to convert DNA concentrations into nM scale. A 2 nM or 4 nM concentration aliquot of the sample was prepared for MiSeq® sequencing as described in the Illumina manual and loaded on the instrument at about 15 µM.

FIG. 9 illustrates the demonstration for half a plate: 851 called clones, spanning 41 constructs (includes both perfects and called mutations). 80 pairs of primers (about 2 per construct) were generated. 67 of 80 (84%) of clone isolations were successful. Four clones were sent of each for Sanger sequencing. The barcodes used for this demonstration were the coded barcodes as described above.

Informatics Analysis:

The sequencing reads were taken from the MiSeq® instrument and aligned to reference sequences using Smith-Waterman alignment for the handle sequences. Barcodes from aligned reads were read by taking the sequence adjacent to the handle sequence, thus building a correlation of barcodes to reads. Read pairs were determined where the first read contained the 5' barcode and the second read contained the 3' barcode. These associations were thresholded and scored, to make pairs of high confidence. Those were then used to form subset read populations containing all reads which contained either barcode, and then aligned to the reference sequence to call a consensus sequence for that clone. Traces were generated showing the number of reads called for each position (and their base identity).

Barcode pairs which generated a perfect consensus sequence to the reference were then used to make primers, containing as much of the barcode sequence as possible, having suitable melting temperatures and desired other features. The primers were used in a PCR reaction using KOD polymerase with the template being a small dilution amount of the "fish-out template".

Example 4

Figure 10:
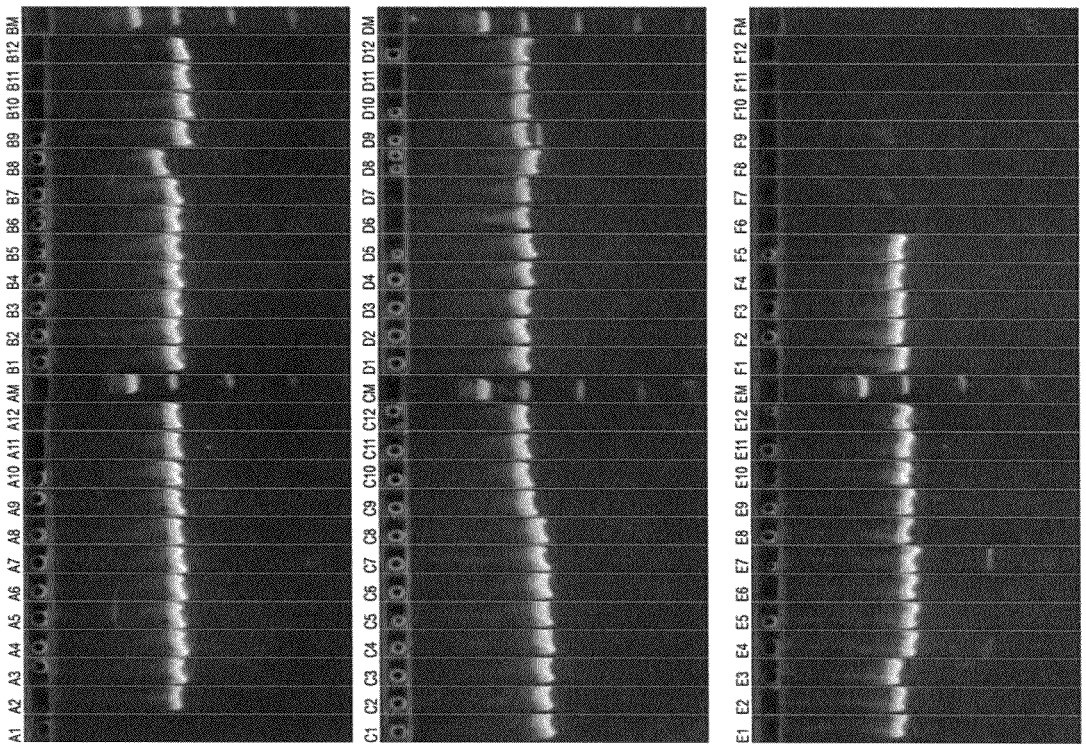
FIG. 10 illustrates a non-limiting exemplary isolation of nucleic acid clones from a pool of constructs using barcodes.

In this full plate example, 87 constructs ranging in size from ~700 to ~1200 bp were pooled together. There were 2052 called clones spanning 71 constructs (82%) with 1387 called perfect (68%). Perfects called spanned 62 constructs (81% of constructs with at least one clone, 71% of constructs within the pool). For 65 constructs, one primer pair corresponding to one clone for each construct was received and used as a barcode and primer to isolate that clone. In total 65 primer pairs were received: 62 perfects, 3 known mutations. FIG. 10 illustrates that the amplification products of 64 of the 65 clones were cleanly detected (A1 missing, see FIG. 10).

EQUIVALENTS

The present invention provides among other things novel methods and devices for high-fidelity gene assembly. While specific embodiments of the subject invention have been discussed, the above specification is illustrative and not restrictive. Many variations of the invention will become apparent to those skilled in the art upon review of this specification. The full scope of the invention should be determined by reference to the claims, along with their full scope of equivalents, and the specification, along with such variations.

INCORPORATION BY REFERENCE

Reference is made to U.S. provisional application Ser. No. 61/851,774, filed Mar. 13, 2013, U.S. provisional application Ser. No. 61/848,961, filed Jan. 16, 2013, U.S. provisional application Ser. No. 61/637,750, filed Apr. 24, 2012, U.S. provisional application Ser. No. 61/638,187, filed Apr. 25, 2012, and International PCT application No. PCT/US2012/042597, filed Jun. 15, 2012. All publications, patents and sequence database entries mentioned herein are hereby incorporated by reference in their entirety as if each individual publication or patent was specifically and individually indicated to be incorporated by reference.

The invention claimed is:

1. A method for isolating error-free nucleic acid molecules having a predefined sequence, the method comprising:
   (a) providing a pool of nucleic acid molecules comprising error-free and error-containing nucleic acid molecules;
   (b) tagging the nucleic acid molecules;
   (c) subjecting at least a subset of the tagged nucleic acid molecules to transposon-mediated fragmentation to form fragmented nucleic acid molecules;
   (d) determining the sequence of the fragmented nucleic acid molecules;
   (e) localizing the error-free and error-containing nucleic acid molecules; and
   (f) isolating the error-free nucleic acid molecules, wherein the error-free nucleic acid molecules have a predefined sequence.

2. The method of claim 1 wherein the step of isolating comprises one or more of
   (a) ablating the error-containing nucleic acid molecules;
   (b) amplifying the error-free nucleic acid molecules;
   (c) immobilizing the error-free nucleic acid molecules onto a surface and separating the error-free nucleic acid molecules from the error-containing nucleic acid molecules.

3. The method of claim 2 wherein in the step of immobilizing, the surface is a bead.

4. The method of claim 3 wherein the pool of nucleic acid molecules comprises at least two populations of nucleic acids and wherein in the step of isolating each population of nucleic acids is onto a distinct population of beads.

5. The method of claim 4 further comprising sorting the distinct populations of beads.

6. The method of claim 1, wherein in the step of providing, the pool of nucleic acid molecules is normalized.

7. The method of claim 1, wherein in the step of providing, each nucleic acid molecule comprises a 5' end common adaptor sequence and 3' end common adaptor sequence.

8. The method of claim 1, wherein in the step of tagging, oligonucleotide tags are ligated to the 5' and 3' end of the nucleic acid molecules.

9. The method of claim 8, wherein the number of tag oligonucleotides in the ligation reaction is greater than the number of nucleic acid molecules in the pool of nucleic acid molecules.

10. The method of claim 8, wherein one or more of the oligonucleotide tags are vectors.

11. The method of claim 8, wherein the oligonucleotide tags comprise a degenerate nucleotide sequence.

12. The method of claim 11, wherein the degenerate nucleotide sequence is CCWSWDHSHDBVHDNNNNMM and/or CCSWSHDSDHVBDHNNNNMM, wherein W represents A or T, S represents G or C, M represents A or C, B represents C, G, or T, D represents A, G, or T, H represents A, C, or T, V represents A, C, or G and N represents any base A, C, G, or T.

13. The method of claim 1, wherein in the step of tagging, oligonucleotide tags are joined to the 5' and 3' end of the nucleic acid molecules by polymerase chain reaction.

14. The method of claim 13, wherein the oligonucleotide tags comprise a degenerate nucleotide sequence.

15. The method of claim 14, wherein the degenerate nucleotide sequence is CCWSWDHSHDBVHDNNNNMM and/or CCSWSHDSDHVBDHNNNNMM, wherein W represents A or T, S represents G or C, M represents A or C, B represents C, G, or T, D represents A, G, or T, H represents A, C, or T, V represents A, C, or G and N represents any base A, C, G, or T.

16. The method of claim 2, wherein in the step of amplifying, the amplification is performed with universal primers.

17. The method of claim 2, wherein in the step of amplifying, the amplification is performed with unique primers.

18. The method of claim 1, further comprising diluting the pool of nucleic acid molecules.

19. The method of claim 1, wherein the step of subjecting comprises controlling the concentration of transposon enzyme, temperature of reaction, and incubation time of reaction.

20. The method of claim 1, wherein the step of subjecting comprises subjecting all the tagged nucleic acid molecules to transposon-mediated fragmentation to form fragmented nucleic acid molecules.

* * * * *

UNITED STATES PATENT AND TRADEMARK OFFICE
CERTIFICATE OF CORRECTION

PATENT NO. : 10,927,369 B2  
APPLICATION NO. : 16/039288  
DATED : February 23, 2021  
INVENTOR(S) : Joseph Jacobson et al.

Page 1 of 1

It is certified that error appears in the above-identified patent and that said Letters Patent is hereby corrected as shown below:

On the Title Page

Item [60], the provisional application number '61/377,750' should be changed to --61/637,750--.

Signed and Sealed this
Twenty-second Day of June, 2021

Drew Hirshfeld
*Performing the Functions and Duties of the*
*Under Secretary of Commerce for Intellectual Property and*
*Director of the United States Patent and Trademark Office*